US007550496B2

(12) United States Patent
Matteucci et al.

(10) Patent No.: US 7,550,496 B2
(45) Date of Patent: Jun. 23, 2009

(54) COMPOSITIONS AND METHODS FOR TREATING CANCER

(75) Inventors: Mark Matteucci, Portola Valley, CA (US); Photon Rao, Foster City, CA (US); Jian-Xin Duan, South San Francisco, CA (US)

(73) Assignee: Threshold Pharmaceuticals, Inc., Redwood City, CA (US)

( * ) Notice: Subject to any disclaimer, the term of this patent is extended or adjusted under 35 U.S.C. 154(b) by 78 days.

(21) Appl. No.: 10/549,545

(22) PCT Filed: Mar. 29, 2004

(86) PCT No.: PCT/US2004/009667

§ 371 (c)(1),
(2), (4) Date: May 26, 2006

(87) PCT Pub. No.: WO2004/087075

PCT Pub. Date: Oct. 14, 2004

(65) Prior Publication Data

US 2006/0258656 A1    Nov. 16, 2006

Related U.S. Application Data

(60) Provisional application No. 60/465,281, filed on Apr. 21, 2003, provisional application No. 60/458,845, filed on Mar. 28, 2003.

(51) Int. Cl.
A61K 31/415     (2006.01)
C07D 233/00     (2006.01)

(52) U.S. Cl. .................. 514/396; 514/397; 514/399; 548/311.1; 548/300.1

(58) Field of Classification Search .............. 548/311.1, 548/300.1; 514/396, 397, 399
See application file for complete search history.

(56) References Cited

U.S. PATENT DOCUMENTS

| 3,652,579 | A | 3/1972 | Hoffer et al. |
| 4,908,356 | A | 3/1990 | Borch et al. |
| 4,921,963 | A | 5/1990 | Skov et al. |
| 4,945,102 | A | 7/1990 | Suzuki et al. |
| 5,190,929 | A | 3/1993 | Borch et al. |
| 5,270,330 | A | 12/1993 | Suzuki et al. |
| 5,306,727 | A | 4/1994 | Borch et al. |
| 5,403,932 | A | 4/1995 | Borch et al. |
| 5,472,956 | A | 12/1995 | Borch et al. |
| 5,622,936 | A | 4/1997 | Wiessler et al. |
| 5,703,080 | A | 12/1997 | Nakakura et al. |
| 5,750,782 | A | 5/1998 | Denny et al. |
| 5,780,585 | A | 7/1998 | Anlezark et al. |
| 5,872,129 | A | 2/1999 | Denny et al. |
| 5,877,158 | A | 3/1999 | Bosslet et al. |
| 5,985,909 | A | 11/1999 | Denny et al. |
| 6,020,315 | A | 2/2000 | Bosslet et al. |
| 6,130,237 | A | 10/2000 | Denny et al. |
| 6,218,519 | B1 | 4/2001 | Kenten et al. |
| 6,240,925 | B1 | 6/2001 | McMillan et al. |
| 6,251,933 | B1 | 6/2001 | Denny et al. |
| 6,506,739 | B1 | 1/2003 | Herr et al. |
| 6,656,926 | B2 | 12/2003 | Borch et al. |
| 6,855,695 | B2 | 2/2005 | Lin et al. |
| 2003/0008850 | A1 | 1/2003 | Borch et al. |
| 2003/0050331 | A1 | 3/2003 | Ng et al. |
| 2003/0096743 | A1 | 5/2003 | Senter et al. |
| 2003/0130189 | A1 | 7/2003 | Senter et al. |
| 2004/0121940 | A1 | 6/2004 | De Groot et al. |
| 2004/0176332 | A1 | 9/2004 | Borch et al. |
| 2004/0254103 | A1 | 12/2004 | Lin et al. |
| 2005/0043244 | A1 | 2/2005 | Lin et al. |

FOREIGN PATENT DOCUMENTS

| DE | 2229223 | | 2/1973 |
| EP | 648 503 | A1 | 4/1995 |
| EP | 312 858 | B1 | 3/1998 |
| WO | WO 97/39007 | A1 | 10/1997 |
| WO | WO 00/64864 | A1 | 11/2000 |
| WO | WO 02/96910 | A1 | 12/2002 |
| WO | WO 04/85361 | A1 | 10/2004 |
| WO | WO 04/85421 | A2 | 10/2004 |

OTHER PUBLICATIONS

Garsky publication, J. Med. Chem., 44(24), 4216-4224, 2001 (Abstarct only).*
Berry et al., "5-Nitrofuran-2-ylmethyl group as a potential bioreductively activated pro-drug system," *J. Chem. Soc. Perkin Trans.*, 1:1147-1156 (1997).
Borch et al., "Synthesis and Evaluation of Nitroheterocyclic Phosphoramidates as Hypoxia-Selective Alkylating Agents," *J. Med. Chem.*, 43:2258-2265 (2000).
Borch et al., "Antitumor Activity and Toxicity of Novel Nitroheterocylic Phosporamidates," *J. Med. Chem.*, 44:74-77 (2001).
De Groot et al., "Anticancer Prodrugs for Application in Monotherapy: Targeting Hypoxia, Tumor-Associated Enzymes, and Receptors," *Current Medical Chemistry*, 8:1093-1122 (2001).
De Jaeger et al., "Relationship of hypoxia to metastatic ability in rodent tumours," *Br. J. Cancer*, 84(9):1280-1285 (2001).
Engle et al., "$^{31}$P NMR Kinetic Studies of the Intra- and Intermolecular Alkylation Chemistry of Phosphoramide Mustard and Cognate N-Phosphorylated Derivatives of $N$,$N$-Bist(2-chlorethyl)amine$^{1,2}$," *J. Med. Chem.*, 25:1347-1357 (1982).
Everett et al., "Modifying rates of reductive elimination of leaving groups from indolequinone prodrugs: a key factor in controlling hypoxia-selective drug release," *Biochemical Pharmacology*, 63:1629-1639 (2002).
Everett et al., "Bioreductively-Activated Prodrugs for Targeting Hypoxic Tissues: Elimination of Aspirin from 2-Nitroimidazole Derivatives," *Biooganic Med. & Chem. Ltrs.*, 9:1267-1272 (1999).

(Continued)

*Primary Examiner*—Rei-tsang Shiao
(74) *Attorney, Agent, or Firm*—Photon Rao; Kevin Kaster; Lance A. Termes

(57) ABSTRACT

Hypoxia-activated prodrugs can be used to treat cancer when administered alone or in combination with one or more antineoplastic agents.

18 Claims, No Drawings

OTHER PUBLICATIONS

Hay et al., "A 2-Nitroimidazole Carbamate Prodrug of 5-Amino-1-(Chloromethyl)-3-[(5,6,7-Trimethoxyindol-2-YL)Carbonyl]-1,2-Dihydro-3*H*[E]Indole (Amino-*Seco*-CBI-TMI) for Use With Adept and Gdept," *Biooganic Med. & Chem. Ltrs.*, 9:2237-2242 (1999).

Hay et al., "Structure-Activity Relationships of 1,2,4-Benzotriazine 1,4-Dioxides as Hypoxia-Selective Analogues of Tirapazamine," *J. Med. Chem.*, 46:169-182 (2003).

Hernick et al., "Design, Synthesis, and Biological Evaluation of Indolequinone Phosphoramidate Prodrugs Targeted to DT-diaphorase," *J. Med. Chem.*, 45:3540-3548 (2002).

Hernick et al., "Studies on the Mechanisms of Activation of Indolequinone Phosphoramidate Prodrugs," *J. Med. Chem.*, 46:148-154 (2003).

Kyle et al., "Direct Assessment of Drug Penetration into Tissue Using a Novel Application of Three-Dimensional Cell Culture," *Cancer Research*, 64:6304-6309 (2004).

Lin et al., "(*o*- and *p*- Nitrobenzyloxycarbobyl)- 5-fluorouracil Derivatives as Potential Conjugated Bioreductive Alkylating Agents," *J. Med. Chem.*, 29:84-89 (1986).

Naylor et al., "Recent Advances in Bioreductive Drug Targeting," *Mini Reviews in Med. Chem.*, 1:17-29 (2001).

Papot et al., "Design of Selectively Activated Anticancer Prodrugs: Elimination and Cyclization Strategies," *Curr. Med. Chem.—Anti-Cancer Agents*, 2:155-185 (2002).

Parveen et al., "2-Nitroimidazol-5-Ylmethyl as a Potential Bioreductively Activated Prodrug System: Reductively Triggered Release of the Parp Inhibitor 5-Bromoisoquinolinone," *Biooganic Med. & Chem. Ltrs.*, 9:2031-2036 (1999).

Rofstad et al., "Hypoxia-induced metastasis of human melanoma cells: involvement of vascular endothelial growth factor-mediated angiogenesis," *Br. J. Cancer*, 80(11):1697-1707 (1999).

Rosen et al., "Phase 1 Study of TLK286 (Telcyta) Administered Weekly in Advanced Malignancies," *Clin. Cancer Res.*, 10:3689-3698 (2004).

Steinberg et al., "Synthesis and Evaluation of Pteroic Acid-Conjugated Nitroheterocyclic Phosphoramidates as Folate Receptor—Targeted Alkylating Agents," *J. Med. Chem.*, 44:69-73 (2001).

Wakselman, M., "1,4- and 1,6- Eliminations from Hydroxy- and Amino-Substituted Benzyl Systems: Chemical and Biochemical Applications," *Nouv. J. Chim.*, 7(7):439-447 (1983).

West et al., "A comparison of adriamycin and mAMSA, II. Studies with V79 and human tumour multicellular spheroids," *Cancer Chemother. Pharmacol.*, 20:109-114 (1987).

Workman et al., "The experimental development of bioreductive drugs and their role in cancer therapy," *Cancer and Metastasis Rev.*, 12:73-82 (1993).

Denny, W. A., "Prodrug strategies in cancer therapy," *Eur. J. Med. Chem.*, 36:577-595 (2001).

Lee et al., "Synthesis and Hypoxia-Selective Cytotoxicity of a 2-Nitroimidazole Mustard," *Bioorganic & Med . Chem. Ltrs.*, 8:1741-1744 (1998).

* cited by examiner

COMPOSITIONS AND METHODS FOR TREATING CANCER

RELATED APPLICATIONS

The present application claims priority benefit of U.S. provisional application 60/465,281, filed Apr. 21, 2003, with title Compositions and Methods for Treating Cancer, and with inventors Mark Matteucci and Photon Rao; and U.S. provisional application 60/458,845, filed Mar. 28, 2003, with title Compositions and Methods for Treating Cancer, and with inventors Mark Matteucci and Photon Rao. The contents of both of these provisional patent applications are included herein in their entirety.

FIELD OF THE INVENTION

The methods described herein provides methods, compounds, and compositions useful in the treatment of cancer.

BACKGROUND

Cancer generally refers to one of a group of more than 100 diseases caused by the uncontrolled growth and spread of abnormal cells that can take the form of solid tumors, lymphomas, and non-solid cancers such as leukemia. Unlike normal cells, which reproduce until maturation is attained and then only as necessary for replacement, cancer cells grow and divide endlessly, crowding out nearby cells and eventually spreading to other parts of the body, unless their progression is stopped. Once cancer cells metastasize by leaving a tumor, they will travel through the bloodstream or lymphatic system to other parts of the body, where the cells begin multiplying and developing into new tumors. This sort of tumor progression makes cancer dangerously fatal. Although there have been great improvements in diagnosis, general patient care, surgical techniques, and local and systemic adjuvant therapies, most deaths from cancer are still due to metastases and other cancers that are resistant to conventional therapies including radiation and chemotherapy.

Radiation therapy is typically only effective for cancer treatment at early and middle stages of cancer, when cancer is localized, and not effective for late stage disease with metastasis. Chemotherapy can be effective at all stages of the disease, but there can be severe side effects, e.g. vomiting, low white blood cells, loss of hair, loss of weight and other toxic effects, to radiation therapy and chemotherapy. Because of such severe side effects, many cancer patients do not or cannot successfully complete a chemotherapy treatment regimen. The side effects of radiation and anticancer drugs can be viewed as resulting from poor target specificity. Anticancer drugs, typically administered intravenously or more rarely orally, circulate through most normal tissues of patients as well as the target tumors. If the drug is toxic to a normal cell, then this circulation will result in the death of normal cells, leading to side effects, and the more toxic the drug to normal cells, the more serious the side effects. Due to these and other problems, some highly cytotoxic chemotherapeutic agents, agents with nanomolar or sub-nanomolar $IC_{50}$ values against cancer cells, have not been successfully developed into approved drugs.

Prodrugs have been investigated as a means to lower the unwanted toxicity or some other negative attribute of a drug without loss of efficacy. A prodrug is a drug that has been chemically modified to render it inactive but that, subsequent to administration, is metabolized or otherwise converted to the active form of the drug in the body. For example, in an effort to improve drug targeting, prodrugs have been developed that are activated under hypoxic conditions. Hypoxia creates a bioreductive environment, and certain anti-cancer agents have been converted into prodrugs that can be activated in such environments. See the reviews by Naylor et al., May 2001, *Mini. Rev. Med.* 1(1):17-29, and Denny, 2001, *Eur. J. Med. Chem.* 36: 577-595. "Hypoxia" is a condition of low oxygen levels; most solid tumors larger than about 1 mm in diameter contain hypoxic regions (see the references Coleman, 1988, *J. Nat. Canc. Inst.* 80: 310; and Vaupel et al., *Cancer Res.* 49: 6449).

As a tumor grows, it requires a blood supply and thus the growth of new vasculature. The new vasculature that supports tumor growth is often highly unordered, leaving significant portions of the tumor under-vascularized and subject to intermittent vascular blockage. The vascular architecture of the tumor can contribute significantly to the cancer's ability to survive drug therapy in at least two different ways. First, if the drug must reach the cancer through the bloodstream, then not as much drug will reach the under-vascularized, hypoxic areas of the tumor. Second, to the extent the drug requires oxygen to be effective, then the drug will be less effective in the hypoxic regions of the tumor.

Conversely, however, the hypoxic environment is conducive to reductive events that can be used to generate reduced derivatives of a variety of chemical groups (see the reference Workman et al., 1993, *Cancer and Metast. Rev.* 12: 73-82), and bioreductive prodrug compounds have been developed to exploit such environments. These prodrugs include the antibiotics Mitomycin C (MMC) and Porfiromycin (POR), N-oxides such as Tirapazamine (TRZ; see the reference Zeeman et al., 1986, *Inst. J. Radiot. Oncol. Biol. Phys.* 12: 1239), quinones such as the indoloquinone E09 (see the reference Bailey et al., 1992, *Int. J. Radiot. Oncol. Biol. Phys.* 22: 649), cyclopropamitosenes (EP-A-0868137), and a tertiary amine-N-oxide analogue of Mitoxantrone (AQ4N) that is activated by cytochrome P450 3A4 (see the references Patterson, 1993, *Cancer Metast. Rev.* 12: 119; and Patterson, 1994, *Biochem. Pharm. Oncol. Res.* 6: 533).

Other bioreductively activated prodrug compounds include the nitroimidazole derivatives that have been reported to be useful in cancer radiotherapy as radio-sensitizing agents (see the patent publications EP312858 and WO91/11440) and potentiatiors of chemotherapeutic agents (see U.S. Pat. No. 4,921,963). Nitroimidazole has also been conjugated to the anti-cancer agent PARP 5-bromoisoquinolinone (see the reference Parveen et al., July 1999, *Bioorg. Med. Chem. Lett.*, 9:2031-36). The nitroimidazole moiety itself is, however, somewhat cytotoxic to normal cells, because it undergoes redox cycling and generates superoxides under oxygenated conditions.

Bioreductively activated prodrug compounds that include a nitroimidazole linked to a variety of anti-neoplastic agents has been described in A 2-NITROIMIDAZOLE CARBAMATE PRODRUG OF 5-AMINO-1-(CHLOROMETHYL)-3-[5,6,7-TRIMETHOXYINDOL-2-YL)CARBONYL]-1,2-DIHYDRO-3H-BENZ[E]INDOLE (AMINO-SECO-CBI-TMI) FOR USE WITH ADEPT AND GDEPT, M. P. Hay et al., Bioorganic & Medicinal Chemistry Letters 9 (1999) 2237-2242, and PCT publication WO 00/64864. In all of the prodrugs described in these documents, the nitroimidazole is directly linked to a carbamate linker and the anti-neoplastic agent is protected at a nitrogen via a carbamate or at a carbon via an ester linkage.

Thus, there remains a need to provide drugs to treat cancer. Such drugs would be especially beneficial if they targeted cancer cells more effectively than current drugs and had fewer, less serious side effects. The present compounds and methods help meet this need.

SUMMARY

Described in the patent are compounds, compositions, and methods for treating cancer.

Provided is a protected anti-neoplastic agent of the formula Hyp-L-N or Hyp-N, where Hyp is a hypoxic activator; N is an anti-neoplastic agent; and L is a linking group of the formula

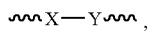

where X is selected from

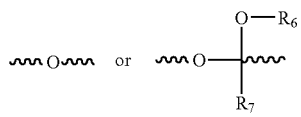

where $R_6$ is unsubstituted alkyl or alkyl substituted with one or more heteroatom containing groups; $R_7$ is hydrogen, unsubstituted alkyl or alkyl substituted with one or more heteroatom containing groups; and Y is a spacer group selected from a substituted or unsubstituted —$(CH_2)_n$— chain with n=1-4; a substituted or unsubstituted —$(CH_2)_n$— chain with n=1-4 in which one of the carbon backbone chain atoms is substituted by a heteroatom containing group; and a delayed release group comprising an aromatic group.

The hypoxic activator may be an electron deficient nitrobenzene moieties, electron deficient nitrobenzoic acid amide moieties, nitroazole moieties, nitroimidazole moieties, nitrothiophene moieties, nitrothiazole moieties, nitrooxazole moieties, nitrofuran moieties, and nitropyrrole moieties. In one version, the hypoxic activator is a substituted or unsubstituted nitroimidazole moiety.

In one version, the hypoxic activator is a moiety of the formula

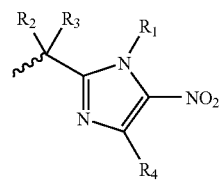

wherein $R_2$ is hydrogen; $R_3$ is hydrogen or $C_1$-$C_6$ alkyl; $R_1$ is an electron withdrawing group, an unsubstituted $C_1$-$C_6$ alkyl, $C_1$-$C_6$ alkyl substituted with one or more heteroatom-containing groups, unsubstituted $C_1$-$C_6$ alkoxy, or $C_1$-$C_6$ alkoxy substituted with one or more heteroatom-containing groups; and $R_4$ is an electron withdrawing group, —H, unsubstituted $C_1$-$C_6$ alkyl, $C_1$-$C_6$ alkyl substituted with one or more heteroatom-containing groups, unsubstituted $C_1$-$C_6$ alkoxy, or $C_1$-$C_6$ alkoxy substituted with one or more heteroatom-containing groups. Specific electron withdrawing groups and substitution for alkyl and alkoxy are described in detail in the Detail Description.

In another version, the hypoxic activator is a moiety of the formula

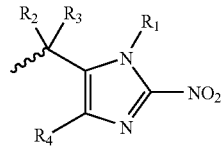

where $R_2$ is hydrogen; $R_3$ is hydrogen or $C_1$-$C_6$ alkyl; $R_1$ is unsubstituted $C_1$-$C_6$ alkyl, $C_1$-$C_6$ alkyl substituted with one or more heteroatom-containing groups, unsubstituted $C_1$-$C_6$ alkoxy, or $C_1$-$C_6$ alkoxy substituted with one or more heteroatom-containing groups; and $R_4$ is —H, unsubstituted $C_1$-$C_6$ alkyl, $C_1$-$C_6$ alkyl substituted with one or more heteroatom-containing groups, unsubstituted $C_1$-$C_6$ alkoxy, or $C_1$-$C_6$ alkoxy substituted with one or more heteroatom-containing groups. Specific substitution for alkyl and alkoxy are described in detail in the Detail Description.

In another version, the hypoxic activator is a nitrobenzene of formula

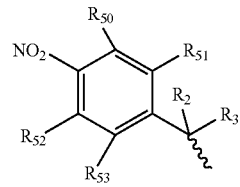

where $R_2$ is hydrogen; $R_3$ is —H, $C_1$-$C_6$ alkyl; and $R_{50}$, $R_{51}$, $R_{52}$, and $R_{53}$ are independently selected from an electron withdrawing group, H, $C_{1-6}$ alkyl or $C_{1-6}$ alkoxy; where the alkyl and alkoxy are optionally independently substituted with one or more groups. Specific electron withdrawing groups and substitution for alkyl and alkoxy are described in detail in the Detail Description.

In one version, the anti-neoplastic agent is bonded to the hypoxic activator (Hyp) or linking group (L) through an hydroxyl oxygen or amine nitrogen in the anti-neoplastic agent. When the anti-neoplastic agent is bonded to the hypoxic activator (Hyp) or linking group (L) by an —O— group, the —O— group may be bonded to an aromatic group in the anti-neoplastic agent, and that aromatic group may be a substituted or unsubstituted phenyl.

Examples of anti-neoplastic agents that may be used include but are not limited to doxorubicin, daunorubicin, duocarmycin, etoposide, duetoposide, Combretastatin A-4, vinblastine, vincristine, camptothecin, topotecan, 5-fluorouracil, AQ4N, hydroxyurea, maytansines, enediyenes, discodermolides, epothilones, taxanes, calicheamicins, tedanolides, bleomycins, calicheamicins, colchicine, cytarabine, dacarbazine, dactinomycin, discodermolides, epirubicin, epirubicin derivatives, fludarabine, hydroxyureapentostatin, 6-mercaptopurine, methotrexate, mitomycin, mitoxantrone, carboplatin, cisplatin, prednisone, procarbazine, taxanes, docetaxel, paclitaxel, tedanolides, teniposide, 6-thioguanine, vinca alkaloids, cyclophosphamides, platinum coordination complexes, anthracenediones, substituted ureas, and methylhydrazine derivatives.

The compound released upon reduction of the hypoxic activator may have an $IC_{50}$ of less than about 100 nM.

In one version, X is the ether group and Y is —(CR$^c$R$^d$)— where R$^c$ and R$^d$ are independently hydrogen, unsubstituted alkyl, or alkyl substituted with one or more of hetero-atom containing groups. In one version, R$^c$ and R$^d$ are hydrogen. In one version, R$^c$ and R$^d$ are hydrogen and Y is attached to the anti-neoplastic agent via an oxygen of a hydroxyl group in the anti-neoplastic agent.

In one version, X is the acetal group and Y is an unsubstituted —(CH$_2$)$_n$— chain with n=3 or 4, or a —(CH$_2$)$_n$— chain with n=3 or 4 substituted with one or more heteroatom containing groups. In one version, X and Y are as in the previous sentence and Y is attached to the anti-neoplastic agent via an nitrogen of an amine group in the anti-neoplastic agent.

In the case that Y is a delayed release group, Y may have the formula

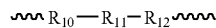

where R$_{10}$ is a bond; R$_{11}$ is an unsubstituted or substituted aryl or heteroaryl group; and R$_{12}$ has the formula —(CR$^{40}$R$^{41}$)—R$^{42}$— or —(CR$^{40}$R$^{41}$)—CR$^{43}$═CR$^{44}$—R$^{42}$—, where R$^{42}$ is a bond or —OC(═O)—, and R$^{40}$, R$^{41}$, R$^{42}$, and R$^{43}$ are independently selected from —H, unsubstituted C$_1$-C$_{10}$ alkyl, and C$_1$-C$_{10}$ alkyl substituted with one or more heteroatom containing groups.

In one version, R$_{11}$ is unsubstituted aryl, substituted aryl, unsubstituted heteroaryl, or substituted heteroaryl, where the substituted aryl or substituted heteroaryl are independently substituted with one or more groups selected from an electron withdrawing group, unsubstituted C$_1$-C$_6$ alkyl, substituted C$_1$-C$_6$ alkyl, unsubstituted C$_1$-C$_6$ alkoxy, and substituted C$_1$-C$_6$ alkoxy; where the substituted alkyl or alkoxy are independently substituted with one or more groups selected from ether (—OR$^{20}$), amino (—NH$_2$), mono-substituted amino (—NR$^{20}$H), di-substituted amino (—NR$^{21}$R$^{22}$), cyclic C$_{1-5}$ alkylamino, imidazolyl, C$_{1-6}$ alkylpiperazinyl, morpholino, thiol (—SH), thioether —(SR$^{20}$), tetrazole, carboxylic acid (—COOH), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(═O)—R$^{20}$), mono-substituted N-connected amide (—NHR$^{21}$—C(═O)—R$^{20}$), disubstituted N-connected amide (—NR$^{21}$R$^{22}$—S(═O)$_2$—R$^{20}$), N-connected sulfonamide (—NH$_2$—S(═O)$_2$—R$^{20}$), mono-substituted N-connected sulfonamide (—NHR$^{21}$—S(═O)$_2$—R$^{20}$), disubstituted N-connected sulfonamide (—NR$^{21}$R$^{22}$—S(═O)$_2$—R$^{20}$), sulphoxy (—S(═O)$_2$OH), sulphonate (S(═O)$_2$OR$^{20}$), sulphonyl (S(═O)$_2$R$^{20}$), sulphixy (S(═O)OH), sulphinate (S(═O)OR$^{20}$), sulphinyl (S(═O)R$^{20}$), phosphonooxy (OP(═O)(OH)$_2$), phosphate (OP(═O)(OR$^{20}$)$_2$), and sulfonamide (—S(═O)$_2$NH$_2$, —S(═O)$_2$NHR$^{21}$, or —S(═O)$_2$NR$^{21}$R$^{22}$), where R$^{20}$, R$^{21}$, and R$^{22}$ are independently selected from a C$_1$-C$_6$ alkyl group; and where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), thiol (—SH), thioether —(SR$^{20}$), carboxylic acid (—COOH), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(═O)—R$^{20}$), mono-substituted N-connected amide (—NHR$^{21}$—C(═O)—R$^{20}$), disubstituted N-connected amide (—NR$^{21}$R$^{22}$—S(═O)$_2$—R$^{20}$), N-connected sulfonamide (—NH$_2$—S(═O)$_2$—R$^{20}$), mono-substituted N-connected sulfonamide (—NHR$^{21}$—S(═O)$_2$—R$^{20}$), disubstituted N-connected sulfonamide (—NR$^{21}$R$^{22}$—S(═O)$_2$—R$^{20}$), sulphoxy (—S(═O)$_2$OH), sulphonate (S(═O)$_2$OR$^{20}$), sulphonyl (S(═O)$_2$R$^{20}$), and sulfonamide (—S(═O)$_2$NH$_2$, —S(═O)$_2$NHR$^{21}$, or —S(═O)$_2$NR$^{21}$R$^{22}$), where R$^{20}$, R$^{21}$, and R$^{22}$ are independently selected from a C$_1$-C$_6$ alkyl group.

In another version, R$_{11}$ is unsubstituted aryl, substituted aryl, unsubstituted heteroaryl, or substituted heteroaryl, where the substituted aryl or substituted heteroaryl are substituted with one or more groups selected from —F, —Cl, —Br, —CN, —OCH$_3$, —NO$_2$, —NH$_2$, —NHR$^{20}$, —NR$^{20}$R$^{21}$, —CH$_3$, —CF$_3$, —CHF$_2$, —CH$_2$F, sulfamide (—S(═O)$_2$NH$_2$, —S(═O)$_2$NHR$^{20}$, or —S(═O)$_2$NR$^{20}$R$^{21}$), carboxamide (—C(═O)NH$_2$, —C(═O)NHR$^{20}$, or —C(═O)NR$^{20}$R$^{21}$); where R$^{20}$, and R$^{21}$ are independently selected from a C$_1$-C$_6$ alkyl group.

In one version, R$_{11}$ is substituted or unsubstituted pyridyl, pyridazinyl, and pyrimidinyl. In another version, R$_{11}$ is substituted or unsubstituted phenyl.

In one version, Y has the formula

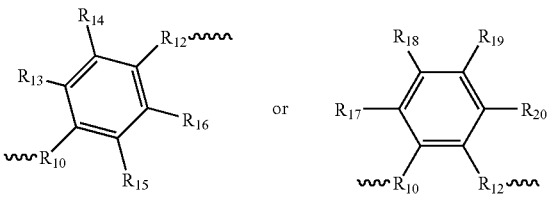

wherein each of R$_{13}$-R$_{20}$ are independently selected from hydrogen, an electron withdrawing group, unsubstituted C$_1$-C$_6$ alkyl, substituted C$_1$-C$_6$ alkyl, unsubstituted C$_1$-C$_6$ alkoxy, and substituted C$_1$-C$_6$ alkoxy; where the substituted alkyl or alkoxy are independently substituted with one or more groups. Specific electron withdrawing groups and substitution for alkyl and alkoxy are described in detail in the Detail Description.

In one version, the linking group L has the formula

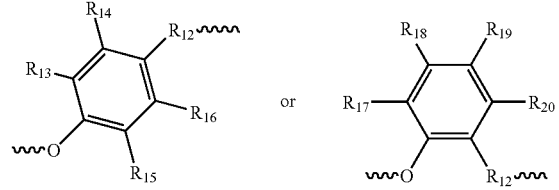

The protected anti-neoplastic agents may be used for treating cancer by administering to a subject a therapeutically effective amount of a protected anti-neoplastic agent. In these methods, the protected anti-neoplastic agent may be administered alone or in combination with an effective amount of one or more chemotherapeutic agents, an effective amount of radiotherapy, a surgery procedure, or any combination of the foregoing. Chemotherapeutic agents that may be used are described in detail in the Detailed Description section.

Cancers that may be treated are described in detail in the Detailed Description section and include lung cancer, non-small cell lung cancer, breast cancer, colon cancer, head and neck cancer, ovarian cancer, pancreatic cancer, and prostate cancer.

DETAILED DESCRIPTION

In this detailed description are first provided definitions useful in understanding the compounds, compositions, and methods described in this patent. A general description of prodrug compounds that may be used for treating cancer is then provided, followed by descriptions of various components in these compounds including (1) hypoxic activator groups, (2) anti-neoplastic agents, and (3) linking groups. A description of methods of treatment using the compounds, including a description of cancers that may be treated, is then included, followed by descriptions of formulations, modes of delivery, dosages, etc that may be used with the compounds and methods described in the patent. Methods of making the compounds are then described, followed by combination therapies, in which the compounds described in this patent are used in combination with other treatments, and finally examples are provided of the compounds, compositions, and methods described in this patent.

Definitions

To facilitate an understanding of the compounds, compositions, and methods described in this patent, the following definitions are provided, and unless defined otherwise, all technical and scientific terms used herein have the meanings ascribed to them by those of skill in the fields to which the compounds and methods described herein belong.

As used herein, "a" or "an" means "at least one" or "one or more."

As used herein "alkyl," unless the context makes clear otherwise, includes any aliphatic group containing carbon and hydrogen including, straight chain, branched chain, cyclic, and carbocycle containing alkyl groups.

As used herein, an "anti-neoplastic agent", "anti-tumor agent", or "anti-cancer agent", refers generally to any agent used in the treatment of cancer. Such agents can be used alone or in combination with other compounds and can alleviate, reduce, ameliorate, prevent, or place or maintain in a state of remission of clinical symptoms or diagnostic markers associated with neoplasm, tumor or cancer. Anti-neoplastic agents include, but are not limited to, anti-angiogenic agents, alkylating agents, antimetabolites, microtubulin polymerization perturbers (for example, Taxol), certain natural products, platinum coordination complexes, anthracenediones, substituted ureas, methylhydrazine derivatives, adrenocortical suppressants, certain hormones and antagonists, anti-cancer polysaccharides and certain herb or other plant extracts.

As used herein, an "anti-neoplastic treatment" "cancer therapy," "cancer treatment," or "treatment of cancer," refers to any approach for ameliorating the symptoms of or delaying the progression of a neoplasm, tumor, or cancer by reducing the number of or growth of cancer cells in the body, typically (but not limited to) by killing or halting the growth and division of cancer cells.

As used herein, a "bioreductive compound" refers to a compound that accepts electrons in an oxidation-reduction reaction.

As used herein, "cancer" refers to one of a group of more than 100 diseases caused by the uncontrolled growth and spread of abnormal cells that can take the form of solid tumors, lymphomas, and non-solid cancers such as leukemia.

As used herein, "malignant" refers to cells that have the capacity of metastasis, with loss of both growth and positional control.

As used herein, "neoplasm" (neoplasia) or "tumor" refers to abnormal new cell or tissue growth, which may be benign or malignant.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity, or improved flavor, for example (see the reference Nogrady, 1985, *Medicinal Chemistry A Biochemical Approach*, Oxford University Press, New York, pages 388-392). Prodrugs can also be prepared using compounds that are not drugs.

Protected Anti-Neoplastic Agents

The particular prodrugs described in this patent that may be used to treat cancer are referred to as "Protected Anti-neoplastic agents". In one version the protected anti-neoplastic agent has the formula Hyp-L-N or Hyp-N, where Hyp is a hypoxic activator; L is a linking group; and N is an anti-neoplastic agent. The various hypoxic activators, linking groups and anti-neoplastic agents that may be used in these protected anti-neoplastic agents are described in the hypoxic activator, linking group, and anti-neoplastic agent sections below.

In another version, the protected anti-neoplastic agent is an anti-neoplastic agent in which one or more hydroxyl and/or amine groups present in the anti-neoplastic agent are protected by a hypoxic activator group, Hyp, which is bonded directly to the amine or hydroxyl group either directly or through a linker group, L. Anti-neoplastic agents, hypoxic activators and linking groups that may be used are described in the anti-neoplastic agents, Hypoxic activator and Linking group sections below. When the amine or hydroxyl group in the anti-neoplastic agent is protected the hydrogen in the hydroxyl group or one or more of the moieties attached to the nitrogen in the amine group are replaced by a bond to the protecting group, i.e., by a bond to the Hyp-group or to the Hyp-L-group. In one version, the amine is a primary amine and one of the hydrogens is replaced by the protecting group.

The following schematic shows the attachment of a hypoxic activator to a hydroxyl oxygen and an amine nitrogen via a linking group, L.

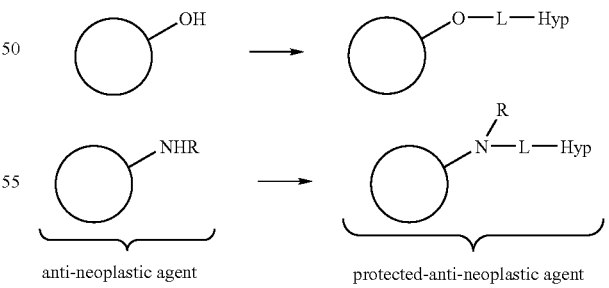

Generally, any number of amine and any number of hydroxyl groups in an anti-neoplastic agent may be protected. In one version, one amine group in an anti-neoplastic agent is protected. In another version, one hydroxyl in an anti-neoplastic agent is protected. If more than one hydroxyl and/or amine group is protected in an anti-neoplastic agent, the protecting groups can be the same or can be different.

In one version, the protected group in the anti-neoplastic agent is a hydroxyl group that is attached to an aromatic or heteroaromatic ring in the anti-neoplastic agent. The aromatic or heteroaromatic ring may be substituted or unsubstituted and may be fused with one or more additional rings, which may be aromatic or nonaromatic and may contain any number of hetero ring atoms. In one version, the protected hydroxyl is attached to a phenyl ring in the anti-neoplastic agent, and the phenyl ring may be substituted or unsubstituted and may be fused with one or more additional rings, which may be aromatic or nonaromatic and may contain any number of hetero ring atoms.

In all of the versions described in this section, the protected amine or protected hydroxyl may be bonded either directly to any hypoxic activator or bonded to any hypoxic activator via any linking group described in the patent.

Nature of groups in anti-neoplastic agent that may be protected: As described above, hydroxyl and amine groups in an anti-neoplastic agent may be protected by attachment to a hypoxic activator, either directly or through a linker. Other groups that may be protected include sulfur based groups, aldehydo groups, and keto groups.

Protected Anti-neoplastic agents can release Anti-neoplastic agent or Modified Anti-neoplastic agent, Including "Super Toxins": Depending on whether the anti-neoplastic agent is bonded directly to the hypoxic activator and depending on the nature of the linking group if the anti-neoplastic agent is bonded via a linking group to the hypoxic activator, the molecule released upon reduction of the hypoxic activator is either the anti-neoplastic agent or a modified anti-neoplastic agent that includes some or all of the linking group attached to the anti-neoplastic agent. As used in this patent, a "modified anti-neoplastic agent" refers to a species that is released from a protected anti-neoplastic agent and that is different from the anti-neoplastic agent itself. For example, a protected anti-neoplastic agent with formula Hyp-L-N may yield a modified anti-neoplastic agent of formula L-N upon reduction of the hypoxic activator. When reduction of the hypoxic activator liberates a modified anti-neoplastic agent, the linking group attached to the anti-neoplastic agent may undergo rearrangement or degradation to yield either the unmodified anti-neoplastic agent or some other modified anti-neoplastic agent.

General examples of this aspect of the protected anti-neoplastic agents is described in the Linking Groups section.

That the molecule released upon reduction of the hypoxic activator may be different from the anti-neoplastic agent being protected will be appreciated by those of skill in the art. This is illustrated in the Examples below, one of which shows that a protected anti-neoplastic agent can be synthesized by linking doxorubicin to a hypoxic activator to form a protected anti-neoplastic agent that releases an iminium-containing doxorubicin derivative that is far more toxic than doxorubicin.

The protected anti-neoplastic agents described in this patent generally exhibit greater efficacy and/or fewer side effects than prior compounds. For example, certain protected anti-neoplastic agents described in this patent are conjugated to, or are activated by hypoxic conditions to release very powerful cytotoxic agents, "super toxins" with $IC_{50}$ values of less than 100 nM against a majority of the cancer cell lines in the NCI tumor cell line panel. Regarding possible toxicity of the protected anti-neoplastic agents, even though the protected anti-neoplastic agents still generate the superoxide that may cause unwanted side effects, those side effects are greatly reduced relative to the effects of prior compounds, because, on a molar basis, much less protected anti-neoplastic agent has to be given due to the highly cytotoxic nature of the anti-cancer agent released by the protected anti-neoplastic agent. Generally (maybe with the exception of compounds described in A 2-NITROIMIDAZOLE CARBAMATE PRODRUG OF 5-AMINO-1-(CHLOROMETHYL)-3-[5,6,7-TRIMETHOXYINDOL-2-YL)CARBONYL]-1,2-DIHYDRO-3H-BENZ[E]INDOLE (AMINO-SECO-CBI-TMI) FOR USE WITH ADEPT AND GDEPT, M. P. Hay et al., Bioorganic & Medicinal Chemistry Letters 9 (1999) 2237-2242, and PCT publication WO 00/64864.) the protected anti-neoplastic agents described in this patent that release "super toxins" can be used in much lower doses than the nitroimidazole prodrugs heretofore known. These lower doses produce less superoxide (see discussion below) in normoxic tissue.

The protected anti-neoplastic agents can be used to release a wide variety of anti-neoplastic agents as is described in the Anti-neoplastic agent section in this patent.

Protected Anti-neoplastic agents may have reduced Toxicity: The protected anti-neoplastic agents, relative to the drugs to which they are converted in vivo, maybe much less (at least ten and up to one million-fold less) toxic. The reduced toxicity results from a modification at the site of attachment of the linker L (as in the case where activation of the protected anti-neoplastic agents releases the same cytotoxic agent that was used in the synthesis of the drug) or from the generation of a moiety required for toxicity by removal of the hypoxic activator (Hyp). In either event, the protected anti-neoplastic agents are converted into the corresponding toxic drug in hypoxic tissues by virtue of the activation of the hypoxic activator moiety, resulting in its removal and the concomitant release or generation of the anti-neoplastic agent or a modified version of the anti-neoplastic agent.

Regardless of the anti-neoplastic agent, N, selected for incorporation in or release by the Protected Anti-neoplastic agents, in one version the linker and hypoxic activator moiety are attached to the anti-neoplastic agent, N, in a manner that masks or reduces the cytotoxic activity of the anti-neoplastic agent. This masking effect can vary and may depend on the cytotoxic activity of the anti-neoplastic agent to be released. Typically, the protected anti-neoplastic agent will show at least about 10 fold less cytotoxic activity than the anti-neoplastic agent, and may show up to about a million fold or more or less cytotoxic activity. In one version, the cytotoxic activity of the protected anti-neoplastic agent is about 100 fold to about 10,000 fold less than the cytotoxic activity of the anti-neoplastic agent. As one example, for an anti-neoplastic agent with an $IC_{50}$ of 1 nM, the corresponding $IC_{50}$ of the protected anti-neoplastic agent can be 1 microM or greater.

In one version, the Protected Anti-neoplastic agents described in this patent include as anti-neoplastic agents, N, any agent that can be linked to a hypoxic activator in a manner that yields a protected anti-neoplastic agent that is at least about 10-fold to about 1,000,000-fold, and typically about 100 to about 10,000-fold, less active as a cytotoxic agent than the anti-neoplastic agent or modified anti-neoplastic agent that is released from the Protected Anti-neoplastic agent under hypoxic conditions.

Possible Mechanism of Action of Protected Anti-Neoplastic Agents: Nitroimidazoles have previously been used to form prodrugs for some putative anti-cancer agents, including a PARP inhibitor (see the reference Parveen et al., 1999, *Bioorganic and Medicinal Letters* 9: 2031-2036) a nitrogen mustard, which was activated, not released, by the nitroimidazole (see the reference Lee et al., 1998, *Bioorganic and Medicinal Letters* 8: 1741-1744) and the agents described in the A 2-NITROIMIDAZOLE CARBAMATE PRODRUG OF 5-AMINO-1-(CHLOROMETHYL)-3-[5,6,7-TRI- METHOXYINDOL-2-YL)CARBONYL]-1,2-DIHYDRO-3H-BENZ[E]INDOLE (AMINO-SECO-CBI-TMI) FOR USE WITH ADEPT AND GDEPT, M. P. Hay et al., Bioorganic & Medicinal Chemistry Letters 9 (1999) 2237-2242, and PCT publication WO 00/64864. The PARP inhibitor was shown to be released chemically, but no cell culture data was provided. The nitrogen mustard was shown to be active in cell culture data, and the selectivity between normoxic and hypoxic toxicity, while not accurately measured, was stated as greater than 7 fold in cells with normal DNA repair mechanisms.

The Protected Anti-neoplastic agents described in this patent differ from such known prodrugs in various ways including but not limited to the nature of the anti-neoplastic agent released, the nature of the linking of the hypoxic activator to the anti-neoplastic agent the better side effect profile, the presence of more than one hypoxic activator moiety, or some combination of these attributes. Without being bound by theory, these advantages of the protected anti-neoplastic agents can be better appreciated with an understanding of the pharmacokinetics of hypoxia-activated prodrugs generally and the protected anti-neoplastic agents described in this patent in particular.

In one version, the protected anti-neoplastic agent includes a nitroimidazole as the hypoxic activator. Nitroimidazole is, in the absence of oxygen, converted to a free radical containing moiety by a cytochrome P450 reductase. If the nitroimidazole is appropriately covalently bound to another moiety, further reduction of the free radical form of nitroimidazole can lead to release of that moiety. However, in the presence of oxygen, the free radical reacts with oxygen to form superoxide and the parent nitroimidazole. Superoxide is a cytotoxin, so the production of superoxide in normoxic tissues is believed to lead to unwanted side effects.

Certain nitroimidazole-containing prodrugs can also be activated regardless of the oxygen tension by DT diaphorase, which can lead to activation in normoxic cells, thus contributing to unwanted side effects. Should this normoxic activation pathway create significant side effects with a particular protected anti-neoplastic agent, however, one can select another protected anti-neoplastic agent that contains more than one hypoxia-activated moiety to reduce or eliminate such side effects.

Without being bound by theory, in the case of protected anti-neoplastic agents in which the hypoxic activator is a nitroimidazole, the hypoxic activator is activated under hypoxic conditions through the nitro group being reduced to a hydroxylamine or an amine with concomitant release of the portion of the molecule to which the hypoxic activator is attached. This activation process is shown in the following scheme. Although the scheme shown illustrates an ether linkage between the hypoxic activator and the remainder of the protected anti-neoplastic agent, similar mechanisms will apply for the acetal groups to which the hypoxic activator is attached. For example, for a protected anti-neoplastic agent containing a nitroimidazole as the hypoxic activator, reduction of the hypoxic activator will release at least initially an aldehyde when the hypoxic activator is attached to an acetal group and will release, at least initially, an alcohol when the hypoxic activator is attached to an ether group. Without being bound by theory, the following scheme presents a mechanism for release from one version of a hypoxic activator.

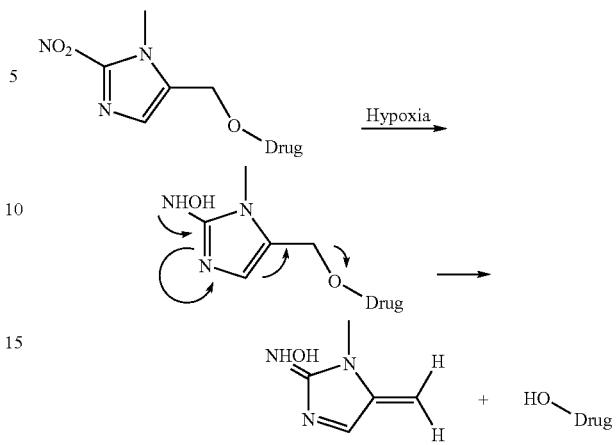

Hypoxic Activators

Generally the hypoxic activator can be any group that is capable of releasing the anti-neoplastic agent or a modified version of the anti-neoplastic agent upon hypoxic reduction of the hypoxic activator. In one version the hypoxic activator is a group that is capable of releasing the anti-neoplastic agent or a modified version of the anti-neoplastic agent upon reduction of the hypoxic activator under hypoxic conditions but that does not release substantially any anti-neoplastic agent or a modified version of the anti-neoplastic agent under normoxic conditions.

Examples of hypoxic activators include but are not limited to moieties based on electron deficient nitrobenzenes, electron deficient nitrobenzoic acid amides, nitroazoles, nitroimidazoles, nitrothiophenes, nitrothiazoles, nitrooxazoles, nitrofurans, and nitropyrroles where each of these classes of moieties may be substituted or unsubstituted. In one version, the hypoxic activator is substituted nitroimidazole. In one version, the hypoxic activator is substituted nitrobenzene. One of skill in the art will understand how to substitute these and other possible groups to provide a redox potential for the group in a range capable of undergoing reduction in the hypoxic conditions described in this patent. For example, and as described in more detail below, one version of the hypoxic activator is a nitroimidazole that may be substituted with a variety of groups. In further examples, the thiophene, furan thiazole, and moieties may be substituted with one or more electron donating groups, including but not limited to methyl or methoxy or amine groups to achieve the desired range of redox potential. In another example, the nitropyrrole moiety may require substitution of electron withdrawing group including but not limited to cyano, carboxamide, —CF3, and sulfonamide groups to achieve the desired range of redox potential. Generally, on of skill in the art will understand how to turn the redox potential of a hypoxic activator by substituting electron withdrawing groups, electron donating groups, or some combination of such groups. As a nonlimiting example, strong electron withdrawing groups such as cyano, sulfone, sulfonamide, carboxamide, or —CF$_3$ may be used, and the redox potential may be fine tuned using milder electron withdrawing groups such as —CH$_2$, —F, —Cl, —Br, or by adding a methylene spacer between the hypoxic activator and the strong electron withdrawing group.

In the case that the hypoxic activator is a nitroimidazole, in one version the hypoxic activator has the formula

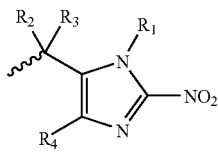

(I)

where the wavy bond indicates the position of attachment of the hypoxic activator to the linking group or anti-neoplastic agent. In another version the hypoxic activator has the formula

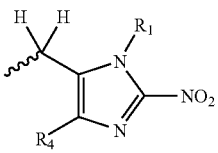

(II)

where the wavy bond indicates the position of attachment of the hypoxic activator to the linking group or anti-neoplastic agent.

In one version of the above hypoxic activators (I & II), $R_2$ is hydrogen; $R_3$ is —H or $C_1$-$C_6$ alkyl; $R_1$ is selected from an $C_1$-$C_6$ alkyl, or $C_1$-$C_6$ alkoxy, where the alkyl or alkoxy is optionally substituted with one or more heteroatom-containing groups; and $R_4$ is selected from —H, $C_1$-$C_6$ alkyl, or $C_1$-$C_6$ alkoxy, where the alkyl or alkoxy is optionally substituted with one or more heteroatom-containing groups.

In one version of the above hypoxic activators (I & II), $R_2$ is hydrogen; $R_3$ is —H or $C_1$-$C_6$ alkyl; $R_1$ is $C_1$-$C_6$ alkyl, where the alkyl is optionally substituted with one or more heteroatom-containing groups; and $R_4$ is selected from —H, or $C_1$-$C_6$ alkyl, where the alkyl is optionally substituted with one or more heteroatom-containing groups.

In one version of the above hypoxic activators (I & II), $R_2$ is hydrogen; $R_3$ is —H or $C_1$-$C_6$ alkyl; and $R_1$ and $R_4$ are each independently —H, or $C_1$-$C_6$ alkyl; where the alkyl is optionally substituted with one or more heteroatom-containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; and with the proviso that $R_1$ is not hydrogen.

In one version, $R_2$ is hydrogen; $R_3$ is —H or $C_1$-$C_6$ alkyl; and $R_1$ and $R_4$ are each independently an H, $C_1$-$C_6$ alkyl or $C_1$-$C_6$ alkoxy, the alkyl or alkoxy being optionally substituted with one or more groups selected from ether (—$OR^{20}$), amino (—$NH_2$), mono-substituted amino (—$NR^{20}H$), di-substituted amino (—$NR^{21}R^{22}$), cyclic $C_{1-5}$ alkylamino, imidazolyl, $C_{1-6}$ alkylpiperazinyl, morpholino, thiol (—SH), thioether —($SR^{20}$), tetrazole, carboxylic acid (—COOH), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), sulphixy (S(=O)OH), sulphinate (S(=O)$OR^{20}$), sulphinyl (S(=O)$R^{20}$), phosphonooxy (OP(=O)(OH)$_2$), phosphate (OP(=O)($OR^{20}$)$_2$), and sulfonamide (—S(=O)$_2$$NH_2$, —S(=O)$_2$$NHR^{21}$, or —S(=O)$_2$$NR^{21}R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group; and with the proviso that $R_1$ is not hydrogen.

In one version of the above hypoxic activators (I & II), $R_2$ is hydrogen; $R_3$ is —H or $C_1$-$C_3$ alkyl; and $R_1$ and $R_4$ are each independently an —H or alkyl selected from methyl, ethyl, n-propyl, n-butyl, n-pentyl, t-butyl, cyclohexyl, cyclopentyl, and isopropyl, where the alkyl is optionally substituted with one or more heteroatom-containing groups; with the proviso that $R_1$ is not hydrogen.

In one version of the above hypoxic activators (I & II), $R_2$ is hydrogen; $R_3$ is —H or $C_1$-$C_3$ alkyl; and $R_1$ and $R_4$ are each independently —H or alkyl selected from methyl, ethyl, n-propyl, n-butyl, n-pentyl, t-butyl, cyclohexyl, cyclopentyl, and isopropyl, where the alkyl is optionally substituted with one or more heteroatom-containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; with the proviso that $R_1$ is not hydrogen.

In one version of the above hypoxic activators (I & II), $R_2$ is hydrogen; $R_3$ is —H or $C_1$-$C_3$ alkyl; and $R_1$ and $R_4$ are each independently —H or alkyl selected from methyl, ethyl, n-propyl, n-butyl, n-pentyl, t-butyl, cyclohexyl, cyclopentyl, and isopropyl, where the alkyl is optionally substituted with one or more heteroatom-containing groups selected from ether (—$OR^{20}$), amino (—$NH_2$), mono-substituted amino (—$NR^{20}H$), di-substituted amino (—$NR^{21}R^{22}$), cyclic $C_{1-5}$ alkylamino, imidazolyl, $C_{1-6}$ alkylpiperazinyl, morpholino, thiol (—SH), thioether —($SR^{20}$), tetrazole, carboxylic acid (—COOH), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), sulphixy (S(=O)OH), sulphinate (S(=O)$OR^{20}$), sulphinyl (S(=O)$R^{20}$), phosphonooxy (OP(=O)(OH)$_2$), phosphate (OP(=O)($OR^{20}$)$_2$), and sulfonamide (—S(=O)$_2$$NH_2$, —S(=O)$_2$$NHR^{21}$, or —S(=O)$_2$$NR^{21}R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group; with the proviso that $R_1$ is not hydrogen.

In one version of the above hypoxic activators (I & II), $R_2$ is hydrogen; $R_3$ is —H or $C_1$-$C_3$ alkyl; and $R_1$ and $R_4$ are each independently selected from methyl, ethyl, n-propyl, or n-butyl, each alkyl optionally substituted by a heteroatom containing group, particularly an amine group a carboxylic acid group, or an amide group.

In one version of the above hypoxic activators (I & II), $R_2$ is hydrogen and $R_1$ and $R_3$ are any of the versions described above and $R_4$ is $C_1$-$C_3$ alkyl optionally substituted with a heteroatom containing group, particularly an amine group a carboxylic acid group, or an amide group.

In one version of the above hypoxic activators (I & II), $R_2$ is hydrogen and $R_1$, $R_3$, and $R_4$ are each independently ethyl, n-propyl, or n-butyl, each optionally substituted by a heteroatom containing group, particularly an amine group a carboxylic acid group, or an amide group In one version of the above hypoxic activators (I & II), $R_2$ is hydrogen; $R_3$ is hydrogen or $C_1$-$C_3$ alkyl; $R_1$ is methyl, methylacetate, or ethyl, n-propyl, or n-butyl, each optionally substituted with an amine group, a carboxylic acid group, or an amide group, and $R_4$ is hydrogen or $C_1$-$C_3$ alkyl.

In one version of the above hypoxic activators (I & II), $R_2$ is hydrogen; $R_3$ is hydrogen or $C_1$-$C_3$ alkyl; $R_1$ is methyl, methylacetate, or ethyl, n-propyl, or n-butyl, each optionally substituted with an amine group, a carboxylic acid group, or an amide group, and $R_4$ is hydrogen.

In one version of the above hypoxic activators (I & II), $R_2$ is hydrogen, $R_1$ is an alkyl group bearing steric hinderance and $R_3$, and $R_4$ are each independently —H or $C_1$-$C_6$ alkyl, optionally substituted with one or more heteroatom-containing groups. In one version, $R_2$ is hydrogen, $R_1$ is methyl and $R_3$, and $R_4$ are each independently —H or $C_1$-$C_6$ alkyl, optionally substituted with one or more heteroatom-containing groups. In one version, $R_2$ is hydrogen, $R_1$ is methylacetate and $R_3$, and $R_4$ are each independently —H or $C_1$-$C_6$ alkyl, optionally substituted with one or more heteroatom-containing groups.

In one version of the above hypoxic activators (I & II), $R_1$, $R_3$, and $R_4$ are any of the versions described above and $R_2$ is selected from —H or $C_{1-6}$ alkyl, optionally substituted with one or more heteroatom containing groups. In one version, $R_1$, $R_3$, and $R_4$ are any of the versions described above and $R_2$ is —H, methyl, n-pentyl, t-butyl, cyclohexyl, cyclopentyl, or isopropyl, all optionally substituted with one or more heteroatom-containing groups selected from hydroxyl, ether, thiol, thioether, sulfuric ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R_1$, $R_3$, and $R_4$ are any of the versions described above and $R_2$ is H, $C_1$-$C_6$ alkyl or $C_1$-$C_6$ alkoxy, the alkyl or alkoxy being optionally substituted with one or more groups selected from ether (—$OR^{20}$), amino (—$NH_2$), mono-substituted amino (—$NR^{20}H$), di-substituted amino (—$NR^{21}R^{22}$), cyclic $C_{1-5}$ alkylamino, imidazolyl, $C_{1-6}$ alkylpiperazinyl, morpholino, thiol (—SH), thioether —($SR^{20}$, tetrazole, carboxylic acid (—COOH), ester (—$COOR^{20}$), amide (—$CONH_2$), mono-substituted amide (—$CONHR^{20}$), disubstituted amide (—$CONR^{21}R^{22}$), N-connected amide (—$NH_2$—C(═O)—$R^{20}$), mono-substituted N-connected amide (—$NHR^{21}$—C(═O)—$R^{20}$), disubstituted N-connected amide (—$NR^{21}R^{22}$—$S$(═O)$_2$—$R^{20}$), N-connected sulfonamide (—$NH_2$—$S$(═O)$_2$—$R^{20}$), mono-substituted N-connected sulfonamide (—$NHR^{21}$—$S$(═O)$_2$—$R^{20}$), disubstituted N-connected sulfonamide (—$NR^{21}R^{22}$—$S$(═O)$_2$—$R^{20}$), sulphoxy (—$S$(═O)$_2$OH), sulphonate ($S$(═O)$_2$$OR^{20}$), sulphonyl ($S$(═O)$_2$$R^{20}$), sulphixy ($S$(═O)OH), sulphinate ($S$(═O)$OR^{20}$), sulphinyl ($S$(═O)$R^{20}$), phosphonooxy (OP(═O)(OH)$_2$), phosphate (OP(═O)($OR^{20}$)$_2$), and sulfonamide (—$S$(═O)$_2$$NH_2$, —$S$(═O)$_2$$NHR^{21}$, or —$S$(═O)$_2$$NR^{21}R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group.

In all of the above versions of the nitroimidazole hypoxic activator, for $R_1$ and $R_4$ the heteroatom substituent on an alkyl group may in one version be on the beta position of the alkyl group. For example, but not limiting, ethyl may be substituted with methoxy at the beta position to give —(CH$_2$)—CH$_2$—O—CH$_3$.

In the case that the hypoxic activator is a nitroimidazole, in another version the hypoxic activator has the formula

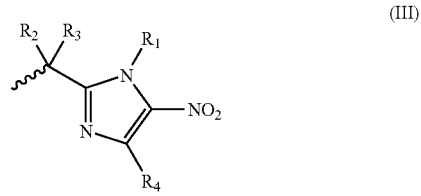

(III)

where the wavy bond indicates the position of attachment of the hypoxic activator to the linking group or anti-neoplastic agent. In another version the hypoxic activator has the formula

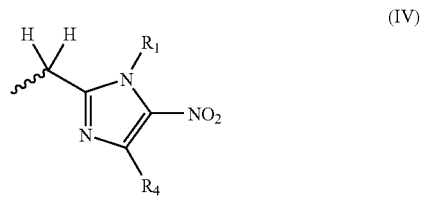

(IV)

where the wavy bond indicates the position of attachment of the hypoxic activator to the linking group or anti-neoplastic agent.

In one version of the above hypoxic activators (III & IV), $R_2$ is hydrogen; $R_3$ is —H or $C_1$-$C_6$ alkyl; $R_1$ is selected from an electron withdrawing group, $C_1$-$C_6$ alkyl, or $C_1$-$C_6$ alkoxy, where the alkyl or alkoxy is optionally substituted with one or more heteroatom-containing groups; and $R_4$ is selected from an electron withdrawing group, —H, $C_1$-$C_6$ alkyl, or $C_1$-$C_6$ alkoxy, where the alkyl or alkoxy is optionally substituted with one or more heteroatom-containing groups. In one version of the hypoxic activator described in this paragraph, at least one of R1 and R4 is an electron withdrawing group.

In one version of the above hypoxic activators (III & IV), $R_2$ is hydrogen; $R_3$ is —H or $C_1$-$C_6$ alkyl; $R_1$ is selected from an electron withdrawing group, or $C_1$-$C_6$ alkyl, where the alkyl is optionally substituted with one or more heteroatom-containing groups; and $R_4$ is selected from an electron withdrawing group, —H, or $C_1$-$C_6$ alkyl, where the alkyl is optionally substituted with one or more heteroatom-containing groups. In one version of the hypoxic activator described in this paragraph, at least one of R1 and R4 is an electron withdrawing group.

In one version of the above hypoxic activators (III & V), $R_2$ is hydrogen; $R_3$ is —H or $C_1$-$C_6$ alkyl; and $R_1$ and $R_4$ are each independently an electron withdrawing group, —H, or $C_1$-$C_6$ alkyl; where the alkyl is optionally substituted with one or more heteroatom-containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; and where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), and sulfonamide (—S(=O)$_2$NH$_2$, —S(=O)NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; with the proviso that R$_1$ is not hydrogen. In one version of the hypoxic activator described in this paragraph, at least one of R1 and R4 is an electron withdrawing group.

In one version of the above hypoxic activators (III & IV), R$_2$ is hydrogen; R$_3$ is —H or C$_1$-C$_6$ alkyl; and R$_1$ and R$_4$ are each independently an electron withdrawing group, H, C$_1$-C$_6$ alkyl or C$_1$-C$_6$ alkoxy, the alkyl or alkoxy being optionally substituted with one or more groups selected from ether (—OR$^{20}$), amino (—NH$_2$), mono-substituted amino (—NR$^{20}$H), di-substituted amino (—NR$^{21}$R$^{22}$), cyclic C$_{1-5}$ alkylamino, imidazolyl, C$_{1-6}$ alkylpiperazinyl, morpholino, thiol (—SH), thioether —(SR$^{20}$), tetrazole, carboxylic acid (—COOH), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), sulphixy (S(=O)OH), sulphinate (S(=O)OR$^{20}$), sulphinyl (S(=O)R$^{20}$), phosphonooxy (OP(=O)(OH)$_2$), phosphate (OP(=O)(OR$^{20}$)$_2$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; with the proviso that R$_1$ is not hydrogen. In one version of the hypoxic activator described in this paragraph, at least one of R1 and R4 is an electron withdrawing group.

In one version of the above hypoxic activators (III & IV), R$_2$ is hydrogen; R$_3$ is —H or C$_1$-C$_3$ alkyl; and R$_1$ and R$_4$ are each independently an electron withdrawing group, —H or alkyl selected from methyl, ethyl, n-propyl, n-butyl, n-pentyl, t-butyl, cyclohexyl, cyclopentyl, and isopropyl, where the alkyl is optionally substituted with one or more heteroatom-containing groups; where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; with the proviso that R$_1$ is not hydrogen. In one version of the hypoxic activator described in this paragraph, at least one of R1 and R4 is an electron withdrawing group.

In one version of the above hypoxic activators (III & IV), R$_2$ is hydrogen; R$_3$ is —H or C$_1$-C$_3$ alkyl; and R$_1$ and R$_4$ are each independently an electron withdrawing group, —H or alkyl selected from methyl, ethyl, n-propyl, n-butyl, n-pentyl, t-butyl, cyclohexyl, cyclopentyl, and isopropyl, where the alkyl is optionally substituted with one or more heteroatom-containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; with the proviso that R$_1$ is not hydrogen. In one version of the hypoxic activator described in this paragraph, at least one of R1 and R4 is an electron withdrawing group.

In one version of the above hypoxic activators (III & IV), $R_2$ is hydrogen; $R_3$ is —H or $C_1$-$C_3$ alkyl; and $R_1$ and $R_4$ are each independently an electron withdrawing group, —H or alkyl selected from methyl, ethyl, n-propyl, n-butyl, n-pentyl, t-butyl, cyclohexyl, cyclopentyl, and isopropyl, where the alkyl is optionally substituted with one or more heteroatom-containing groups selected from ether (—$OR^{20}$), amino (—$NH_2$), mono-substituted amino (—$NR^{20}H$), di-substituted amino (—$NR^{21}R^{22}$), cyclic $C_{1-5}$ alkylamino, imidazolyl, $C_{1-6}$alkylpiperazinyl, morpholino, thiol (—SH), thioether —($SR^{20}$), tetrazole, carboxylic acid (—COOH), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), sulphixy (S(=O)OH), sulphinate (S(=O)$OR^{20}$), sulphinyl (S(=O)$R^{20}$), phosphonooxy (OP(=O)(OH)$_2$), phosphate (OP(=O)($OR^{20}$)$_2$), and sulfonamide (—S(=O)$_2$$NH_2$, —S(=O)$_2$$NHR^{21}$, or —S(=O)$_2$$NR^{21}NR^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group; where the electron withdrawing group is selected from halo, cyano (—CN), haloalkyl, carboxamide, nitro, aldehydo (—CHO), keto (—$COR^{20}$), alkenyl, alkynyl, quaternary amino (—$N^+R^{20}R^{21}R^{22}$), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$, disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), and sulfonamide (—S(=O)$_2$$NH_2$, —S(=O)$_2$$NHR^{21}$, or —S(=O)$_2$$NR^{21}R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group with the proviso that $R_1$ is not hydrogen. In one version of the hypoxic activator described in this paragraph, at least one of R1 and R4 is an electron withdrawing group.

In one version of the above hypoxic activators (III & IV), $R_2$ is hydrogen; $R_3$ is —H or $C_1$-$C_3$ alkyl; and $R_1$ and $R_4$ are each independently selected from cyano, haloalkyl, carboxamide, methyl, ethyl, n-propyl, or n-butyl, each optionally substituted by a heteroatom containing group, particularly an amine group a carboxylic acid group, or an amide group. In one version of the hypoxic activator described in this paragraph, at least one of R1 and R4 is an electron withdrawing group.

In one version of the above hypoxic activators (III & IV), $R_2$ is hydrogen and $R_1$ and $R_3$ are any of the versions described above and $R_4$ is $C_1$-$C_3$ alkyl optionally substituted with a heteroatom containing group, particularly an amine group a carboxylic acid group, or an amide group.

In one version of the above hypoxic activators (III & IV), $R_2$ is hydrogen and $R_1$, $R_3$, and $R_4$ are each independently ethyl, n-propyl, or n-butyl, each optionally substituted by a heteroatom containing group, particularly an amine group a carboxylic acid group, or an amide group In one version of the above hypoxic activators (III & IV), $R_2$ is hydrogen; $R_3$ is hydrogen or $C_1$-$C_3$ alkyl; $R_1$ is methyl, methylacetate, or ethyl, n-propyl, or n-butyl, each optionally substituted with an amine group, a carboxylic acid group, or an amide group, and $R_4$ is hydrogen or $C_1$-$C_3$ alkyl.

In one version of the above hypoxic activators (III & IV), $R_2$ is hydrogen; $R_3$ is hydrogen or $C_1$-$C_3$ alkyl; $R_1$ is methyl, methylacetate, or ethyl, n-propyl, or n-butyl, each optionally substituted with an amine group, a carboxylic acid group, or an amide group, and $R_4$ is hydrogen.

In one version of the above hypoxic activators (III & IV), $R_2$ is hydrogen, $R_1$ is an alkyl group bearing steric hinderance and $R_3$, and $R_4$ are each independently —H or $C_1$-$C_6$ alkyl, optionally substituted with one or more heteroatom-containing groups. In one version, $R_2$ is hydrogen, $R_1$ is methyl and $R_3$, and $R_4$ are each independently —H or $C_1$-$C_6$ alkyl, optionally substituted with one or more heteroatom-containing groups. In one version, $R_2$ is hydrogen, $R_1$ is methylacetate and $R_3$, and $R_4$ are each independently —H or $C_1$-$C_6$ alkyl, optionally substituted with one or more heteroatom-containing groups.

In another version of nitroimidazole hypoxic activators, the hypoxic activator is selected from one of the following

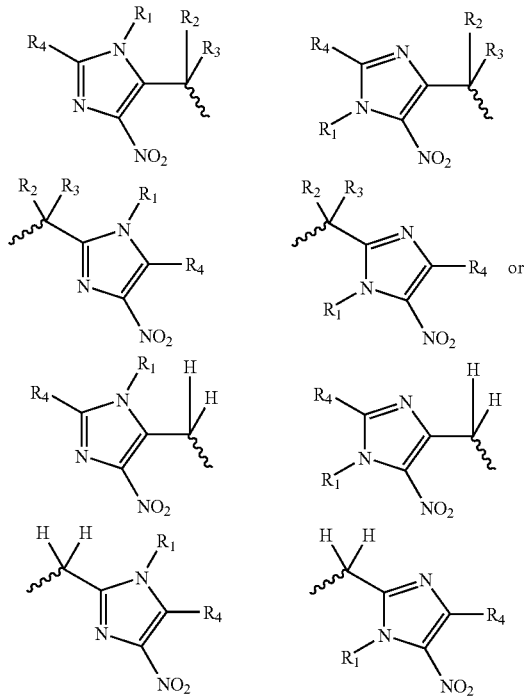

In these versions of the nitroimidazole hypoxic activator, $R_1$, $R_2$, $R_3$, and $R_4$ are as described in any of the versions above.

In one version, $R_1$, $R_3$, and $R_4$ are any of the versions described above for any of the hypoxic activators and $R_2$ is selected from —H or $C_{1-6}$ alkyl, optionally substituted with one or more heteroatom containing groups. In one version, $R_1$, $R_3$, and $R_4$ are any of the versions described above and $R_2$ is —H, methyl, n-pentyl, t-butyl, cyclohexyl, cyclopentyl, or isopropyl, all optionally substituted with one or more heteroatom-containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R_1$, $R_3$, and $R_4$ are any of the versions described above and $R_2$ is H, $C_1$-$C_6$ alkyl or $C_1$-$C_6$ alkoxy, the alkyl or alkoxy being optionally substituted with one or more groups selected from ether (—$OR^{20}$), amino (—$NH_2$), mono-substituted amino (—$NR^{20}H$), disubstituted amino (—$NR^{21}R^{22}$), cyclic $C_{1-5}$ alkylamino, imidazolyl, $C_{1-6}$ alkylpiperazinyl, morpholino, thiol (—SH), thioether —($SR^{20}$), tetrazole, carboxylic acid (—COOH), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$, sulphoxy (—S(=O)$_2$OH), sulphonate (S(=O)$_2$$OR^{20}$), sulphonyl (S(=O)$_2$$R^{20}$), sulphixy (S(=O)OH), sulphinate (S(=O)$OR^{20}$), sulphinyl (S(=O)$R^{20}$), phosphonooxy (OP(=O)(OH)$_2$), phosphate (OP(=O)($OR^{20}$)$_2$), and sulfonamide (—S(=O)$_2$$NH_2$, —S(=O)$_2$$NHR^{21}$, or —S(=O)$_2$$NR^{21}R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group.

In the case that the hypoxic activator is a nitrobenzene, in one version the hypoxic activator has the formula

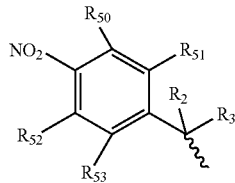

where $R_2$ and $R_3$ are as defined in any of the versions above, and $R_{50}$, $R_{51}$, $R_{52}$, and $R_{53}$ are independently an electron withdrawing group, H, $C_{1-6}$ alkyl or $C_{1-6}$ alkoxy, said alkyl or alkoxy being optionally substituted with one or more groups selected from ether (—$OR^{20}$), amino (—$NH_2$), mono-substituted amino (—$NR^{20}H$), di-substituted amino (—$NR^{21}R^{22}$), cyclic $C_{1-5}$ alkylamino, imidazolyl, $C_{1-6}$ alkylpiperazinyl, morpholino, thiol (—SH), thioether —($SR^{20}$), tetrazole, carboxylic acid (—COOH), ester (—$COOR^{20}$), amide (—$CONH_2$), mono-substituted amide (—$CONHR^{20}$, disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), sulphixy (S(=O)OH), sulphinate (S(=O)$OR^{20}$), sulphinyl (S(=O)$R^{20}$), phosphonooxy (OP(=O)(OH)$_2$), phosphate (OP(=O)($OR^{20}$)$_2$), and sulfonamide (—S(=O)$_2$$NH_2$, —S(=O)$_2$$NHR^{21}$, or —S(=O)$_2$$NR^{21}R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group; where the electron withdrawing group is selected from halo, cyano (—CN), haloalkyl, carboxamide, nitro, aldehydo (—CHO), keto (—$COR^{20}$), alkenyl, alkynyl, quaternary amino (—$N^+R^{20}R^{21}R^{22}$), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), and sulfonamide (—S(=O)$_2$$NH_2$, —S(=O)$_2$$NHR^{21}$, or —S(=O)$_2$$NR^{21}$$R^{22}$), where $R^{20}$, $R^{21}$, and $R^{22}$ are independently selected from a $C_1$-$C_6$ alkyl group, a $C_3$-$C_{20}$ heterocyclic group, or a $C_3$-$C_{20}$ aryl group, preferably a $C_1$-$C_6$ alkyl group.

In one version, at least one of $R_{50}$, $R_{51}$, $R_{52}$, and $R_{53}$ is an electron withdrawing group. In one version, at least one of $R_{50}$ and $R_{52}$ is an electron withdrawing group.

In one version, one or more of the phenyl ring carbons is replaced with a hetero atom. In one version, one of the carbon ring atoms if replaced by a nitrogen to give a pyridyl group.

In another version of nitrobenzene hypoxic activators, the hypoxic activator has the formula

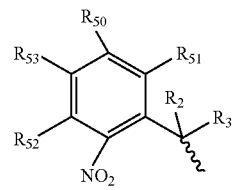

In this version of the nitrobenzene, $R_2$, $R_3$, $R_{50}$, $R_{51}$, $R_{52}$, and $R_{53}$ are as described in any of the versions above. In one version, at least one of $R_{50}$, $R_{51}$, $R_{52}$, and $R_{53}$ is an electron withdrawing group. In one version, $R_{52}$ is an electron withdrawing group. In one version, one or more of the phenyl ring carbons is replaced with a hetero atom. In one version, one of the carbon ring atoms if replaced by a nitrogen to give a pyridyl group.

Linking Group (L)

If present in the protected anti-neoplastic agent, the linking group, L, links the hypoxia activator to the anti-neoplastic agent. That is, the protected anti-neoplastic agent has the formula Hyp-L-N.

Generally, the linking group is a group that is capable of being cleaved from the hypoxic activator upon reduction of the hypoxic activator yielding a modified neoplastic agent that is either itself a neoplastic agent or through rearrangement, degradation, or other chemical modification yields a neoplastic agent. Specific examples are included elsewhere in this patent of such rearrangements and degradations of the modified neoplastic agents resulting from cleavage from the hypoxic activator.

In one version, the linking group is a group of formula

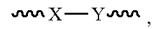

where X is an ether or acetal group and Y is a spacer group as described in more detail below. In the formula

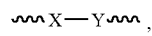

the wavy bond on the X group shows the point of attachment of X to the hypoxic activator and the wavy bond on the Y group shows the point of attachment of the Y group to the anti-neoplastic agent.

X Group:

In one version, X is one of the following ether (X1) or acetal (X2) groups

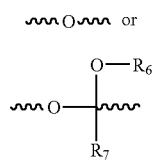

X1

X2 where the wavy line on the left hand side of the X group indicate the point of attachment to the hypoxic activator and the wavy line on the right hand side of the X group indicate the point of attachment to the Y group.

In one version, $R_6$ is unsubstituted alkyl or alkyl substituted with one or more heteroatom containing groups; and $R_7$ is hydrogen, unsubstituted alkyl or alkyl substituted with one or more heteroatom containing groups.

In one version, $R_6$ is unsubstituted $C_1$-$C_{10}$ alkyl or $C_1$-$C_{10}$ alkyl substituted with one or more heteroatom containing groups, and $R_7$ is hydrogen, unsubstituted $C_1$-$C_{10}$ alkyl or $C_1$-$C_{10}$ alkyl substituted with one or more heteroatom containing groups, where for both $R_6$ and $R_7$ the heteroatom containing groups contain one or more of hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R_6$ is unsubstituted $C_1$-$C_{10}$ alkyl.

In one version, $R_6$ is unsubstituted $C_1$-$C_3$ alkyl or $C_1$-$C_3$ alkyl substituted with one or more heteroatom containing groups, and $R_7$ is hydrogen, unsubstituted $C_1$-$C_3$ alkyl or $C_1$-$C_3$ alkyl substituted with one or more heteroatom containing groups, where for both $R_6$ and $R_7$ the heteroatom containing groups contain one or more of hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R_6$ is unsubstituted $C_1$-$C_3$ alkyl.

In one version, $R_7$ is hydrogen, and $R_6$ is unsubstituted $C_1$-$C_3$ alkyl or $C_1$-$C_3$ alkyl substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano.

In one version, $R_6$ is unsubstituted $C_1$-$C_{10}$ alkyl and $R_7$ is hydrogen or unsubstituted $C_1$-$C_{10}$ alkyl.

In one version, $R_6$ is unsubstituted $C_1$-$C_3$ alkyl and $R_7$ is hydrogen or unsubstituted $C_1$-$C_3$ alkyl.

In one version, $R_6$ is methyl and $R_7$ is hydrogen.

Y Group: Generally Y may be any group such that upon reduction of the hypoxic activator the modified anti-neoplastic agent released is cytotoxic or the released modified anti-neoplastic agent undergoes rearrangement, degradation or other chemical transformation to yield a cytotoxic agent.

In one version Y is an unsubstituted —$(CH_2)_n$— chain with n=1-4, or a —$(CH_2)_n$— chain with n=1-4 substituted with one or more heteroatom containing groups. In one version Y is an unsubstituted —$(CH_2)_n$— chain with n=1-4, or a —$(CH_2)_n$— chain with n=1-4 substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano.

In one version, X is the ether group X1 and Y is —($CR^c R^d$)— where $R^c$ and $R^d$ are independently hydrogen, unsubstituted $C_1$-$C_3$ alkyl, or $C_1$-$C_3$ alkyl substituted with one or more of hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, X and Y are as described in the prior sentence and Y is attached to the anti-neoplastic agent via the oxygen of a hydroxyl group in the anti-neoplastic agent; i.e., the protected anti-neoplastic agent includes a formacetal group and has the formula Hyp-O—($CH_2$)—O—N', where the anti-neoplastic agent N is N'—OH.

In one version, X is the ether group X1 and Y is —($CH_2$)—.

In one version, X is the ether group X1, Y is —($CH_2$)—, and Y is attached to the anti-neoplastic agent via the oxygen of a hydroxyl group in the anti-neoplastic agent; i.e., the protected anti-neoplastic agent includes a formacetal group and has the formula Hyp-O—($CH_2$)—O—N', where the anti-neoplastic agent N is N'—OH.

In one version, X is the acetal group X2 and Y is an unsubstituted $C_3$-$C_4$ alkylene chain or a $C_3$-$C_4$ alkylene chain substituted with one or more heteroatom containing groups. In one version, X is the acetal group X2 and Y is an unsubstituted $C_3$-$C_4$ alkylene chain or a $C_3$-$C_4$ alkylene chain substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, X is the acetal group X2, Y is as described in any of the previous sentences, and Y is attached to the anti-neoplastic agent via the nitrogen of an amine group in the anti-neoplastic agent; i.e., the protected anti-neoplastic agent includes has the formula Hyp-O-(substituted or unsubstituted $C_3$-$C_4$ alkylene)-NR—N', where the anti-neoplastic agent N is N'—NRR'.

Y is $C_3$ alkylene: In one version, X is the acetal group X2 and Y is —($CR^e R^f$)—($CR^g R^h$)—($CH_2$)—, where $R^e$, $R^f$, $R^g$, and $R^h$ are independently hydrogen, unsubstituted $C_1$-$C_3$ alkyl, or $C_1$-$C_3$ alkyl substituted with one or more of hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R^e$ and $R^f$ taken together can form an =O group; i.e., —($CR^eR^f$)— is —C(O)—. In one version, $R^g$ and $R^h$ taken together can form an =O group; i.e., —($CR^gR^h$)— is —C(O)—. In one version, $R^e$ and $R^f$ are independently selected from —H and —O—$R^i$, where $R^i$ is unsubstituted $C_1$-$C_5$ alkyl. In one version, $R^g$ and $R^h$ are independently selected from —H and —O—$R^i$, where $R^i$ is unsubstituted $C_1$-$C_5$ alkyl. In one version, X is the acetal group X2, Y is as in any of the versions described in the previous sentences in the paragraph, and Y is attached to the anti-neoplastic agent via the nitrogen of an amine group in the anti-neoplastic agent; i.e., the protected anti-neoplastic agent includes has the formula Hyp-O-(substituted or unsubstituted $C_3$-$C_4$ alkylene)-NR—N', where the anti-neoplastic agent N is N'—NRR'.

Y is $C_4$ alkylene: In one version, X is the acetal group X2 and Y is —($CR^eR^f$)—($CR^gR^h$)—($CR^jR^k$)—($CH_2$)—, where $R^e$, $R^f$, $R^g$, $R^h$, $R^j$, and $R^k$ are independently hydrogen, unsubstituted $C_1$-$C_3$ alkyl, or $C_1$-$C_3$ alkyl substituted with one or more of hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R^e$ and $R^f$ taken together can form an =O group; i.e., —($CR^eR^f$)— is —C(O)—. In one version, $R^g$ and $R^h$ taken together can form an =O group; i.e., —($CR^gR^h$)— is —C(O)—. In one version, $R^j$ and $R^k$ taken together can form an =O group; i.e., —($CR^jR^k$)— is —C(O)—. In one version, $R^e$ and $R^f$ are independently selected from —H and —O—$R^i$, where $R^i$ is —H or unsubstituted $C_1$-$C_5$ alkyl. In one version, $R^g$ and $R^h$ are independently selected from —H and —O—$R^i$, where $R^i$ is —H or unsubstituted $C_1$-$C_5$ alkyl. In one version, $R^j$ and $R^k$ are independently selected from —H and —O—$R^i$, where $R^i$ is —H or unsubstituted $C_1$-$C_5$ alkyl. In one version, X is the acetal group X2, Y is as in any of the versions described in the previous sentences in the paragraph, and Y is attached to the anti-neoplastic agent via the nitrogen of an amine group in the anti-neoplastic agent; i.e., the protected anti-neoplastic agent has the formula Hyp-O-(substituted or unsubstituted $C_3$-$C_4$ alkylene)-NR—N', where the anti-neoplastic agent N is N'—NRR'.

Y is $C_4$ alkylene substituted with one chain hetero group: In one version, X is the acetal group X2 and Y is —($CR^eR^f$)—$R^m$—($CR^jR^k$)—($CH_2$)—, where $R^e$, $R^f$, $R^g$, $R^h$, $R^j$, and $R^k$ are as previously defined above and $R^m$ is selected from —O—, —S—, —S($=$O)$_2$—, —S($=$O)O—, and —NR$^{30}$—, where $R_{30}$ is selected from —C($=$O)R$^{31}$, —C($=$O)NR$^{31}$R$^{32}$, —H, $C_1$-$C_{10}$ alkyl or $C_1$-$C_{10}$ alkyl substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. Where $R^{31}$ and $R^{32}$ are independently selected from $C_1$-$C_{10}$ alkyl or $C_1$-$C_{10}$ alkyl substituted with one or more heteroatom containing groups, selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano.

Y contains a delayed release group: In one version, the Y group is chosen such that the modified anti-neoplastic agent released upon reduction of the hypoxic activator is converted after release into the anti-neoplastic agent or some active derivative of the anti-neoplastic agent. In one version, this degradation occurs by a unimolecular degradation with a half life of unimolecular segregation of between about 0.01 seconds and about 30 seconds. In one version, this degradation occurs by a unimolecular degradation with a half life of unimolecular segregation of between about 0.5 seconds and about 5 seconds.

In this delayed release version of Y, the anti-neoplastic agent or some active derivative of the anti-neoplastic agent is delivered not only at the site of hypoxic reduction of the protected anti-neoplastic agent, but also in surrounding tissue. This occurs because the modified anti-neoplastic agent released upon reduction of the hypoxic activator has time to diffuse to surrounding tissue before it degrades to release the anti-neoplastic agent or active derivative of the anti-neoplastic agent.

In one delayed release version, Y has the formula

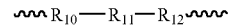

where $R_{11}$ is an unsubstituted or substituted aryl or heteroaryl group, $R_{10}$ is a bond or group attaching the $R_{11}$ group to the X group in the linker, and $R_{12}$ is a bond or group attaching the $R_{11}$ group to the anti-neoplastic agent.

In one version, X is the ether group and Y has the formula

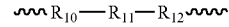

with $R_{10}$, $R_{11}$, and $R_{12}$ as described in any of the versions in this section.

Generally, $R_{11}$ can be any unsubstituted or substituted aryl or heteroaryl group, and the aryl or heteroaryl group may be a monocyclic group or may be a fused ring system.

Examples of fused ring systems that may be used include but are not limited to naphthyl, quinoline or isoquinoline.

In one version, the aryl or heteroaryl group is not a monocyclic or fused ring 5 membered aromatic ring system.

In one version, the point of attachment of the aryl or heteroaryl group to the $R_{10}$ and $R_{12}$ groups may generally be at any ring atom to which a substituent group may be attached and that will allow elimination of the $R_{10}$ and $R_{12}$ groups. In one version, the aryl or heteroaryl group is any group that will allow 1,6 or 1,4 elimination.

In one version, the substituted aryl or heteroaryl group is substituted with one or more groups selected from an electron withdrawing group, substituted or unsubstituted and substituted or unsubstituted alkoxy.

In one version, the substituted aryl or heteroaryl group is substituted with one or more groups selected from an electron withdrawing group, unsubstituted $C_1$-$C_6$ alkyl, substituted $C_1$-$C_6$ alkyl, unsubstituted $C_1$-$C_6$ alkoxy, and substituted $C_1$-$C_6$ alkoxy; where the substituted alkyl or alkoxy are substituted with one or more groups selected from ether (—OR$^{20}$), amino (—NH$_2$), mono-substituted amino (—NR$^{20}$H), di-substituted amino (—NR$^{21}$R$^{22}$), cyclic $C_{1-5}$ alkylamino, imidazolyl, $C_{1-6}$ alkylpiperazinyl, morpholino, thiol (—SH), thioether —(SR$^{20}$), tetrazole, carboxylic acid (—COOH), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$, disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), sulphixy (S(=O)OH), sulphinate (S(=O)OR$^{20}$), sulphinyl (S(=O)R$^{20}$), phosphonooxy (OP(=O)(OH)$_2$), phosphate (OP(=O)(OR$^{20}$)$_2$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; and where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), and sulfonamide (—S(=O)$_2$NH$_2$, —S(=O)$_2$NHR$^{21}$, or —S(=O)$_2$NR$^{21}$NR$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group.

In one version, the substituted aryl or heteroaryl group is substituted with one or more groups selected from —F, —Cl, —Br, —CN, —OCH$_3$, —NO$_2$, —NH$_2$, —NHR$^{20}$, —NR$^{20}$R$^{21}$, —CH$_3$, —CF$_3$, —CHF$_2$, —CH$_2$F, sulfamide (—S(=O)$_2$NH$_2$, —S(=O)$_2$NHR$^{20}$, or —S(=O)$_2$NR$^{20}$R$^{21}$), carboxamide (—C(=O)NH$_2$, —C(=O)NHR$^{20}$, or —C(=O)NR$^{20}$R$^{21}$); where R$^{20}$, and R$^{21}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group.

Examples of monocyclic heteroaryl groups that may be used include but are not limited to pyridyl, pyridazinyl, and pyrimidinyl. In all monocyclic heteroaryl groups, the point of attachment of the heteroaryl group to the R$_{10}$ and R$_{12}$ groups may generally be at any ring atom to which a substituent group may be attached and that will allow elimination of the R$_{10}$ and R$_{12}$ groups.

In one version, R$_{11}$ is an unsubstituted or substituted aryl, particularly an unsubstituted or substituted phenyl. In one version, R$_{11}$ is an unsubstituted or substituted phenyl in which the R$_{10}$ and R$_{12}$ groups are in ortho or para to each other; i.e., Y has the formula

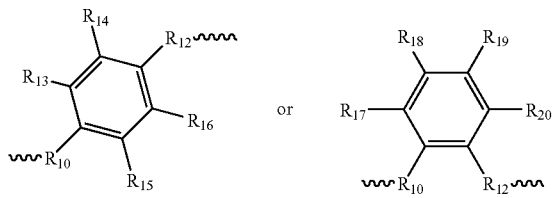

In one version, R$_{13}$-R$_{20}$ are independently selected from an electron withdrawing group, unsubstituted C$_1$-C$_6$ alkyl, substituted C$_1$-C$_6$ alkyl, unsubstituted C$_1$-C$_6$ alkoxy, and substituted C$_1$-C$_6$ alkoxy; where the substituted alkyl or alkoxy are substituted with one or more groups selected from ether (—OR$^{20}$), amino (—NH$_2$), mono-substituted amino (—NR$^{20}$H), di-substituted amino (—NR$^{21}$R$^{22}$), cyclic C$_{1-5}$ alkylamino, imidazolyl, C$_{1-6}$ alkylpiperazinyl, morpholino, thiol (—SH), thioether —(SR$^{20}$), tetrazole, carboxylic acid (—COOH), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), sulphixy (S(=O)OH), sulphinate (S(=O)OR$^{20}$), sulphinyl (S(=O)R$^{20}$), phosphonooxy (OP(=O)(OH)$_2$), phosphate (OP(=O)(OR$^{20}$)$_2$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; and where the electron withdrawing group is selected from halo, cyano (—CN), haloalkyl, carboxamide, nitro, aldehydo (—CHO), keto (—COR$^{20}$), alkenyl, alkynyl, quaternary amino (—N$^+$R$^{20}$R$^{21}$R$^{22}$), ester (—COOR$^{20}$), amide (—CONH$_2$), mono-substituted amide (—CONHR$^{20}$), disubstituted amide (—CONR$^{21}$R$^{22}$), N-connected amide (—NH$_2$—C(=O)—R$^{20}$), mono-substituted N-connected amide (—NHR$^{21}$—C(=O)—R$^{20}$), disubstituted N-connected amide (—NR$^{21}$R$^{22}$—S(=O)$_2$—R$^{20}$), N-connected sulfonamide (—NH$_2$—S(=O)$_2$—R$^{20}$), mono-substituted N-connected sulfonamide (—NHR$^{21}$—S(=O)$_2$—R$^{20}$), disubstituted N-connected sulfonamide (—NR$^{21}$R$^{22}$—S(=O)$_2$—R$^{20}$), sulphoxy (—S(=O)$_2$OH), sulphonate (S(=O)$_2$OR$^{20}$), sulphonyl (S(=O)$_2$R$^{20}$), and sulfonamide (—S(=O)$_2$NH$_2$, —S(=O)$_2$NHR$^{21}$, or —S(=O)$_2$NR$^{21}$R$^{22}$), where R$^{20}$, R$^{21}$, and R$^{22}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group.

In one version, R$_{13}$-R$_{20}$ are independently selected from —F, —Cl, —Br, —CN, —OCH$_3$, —NO$_2$, —NH$_2$, —NHR$^{20}$, —NR$^{20}$R$^{21}$, —CH$_3$, —CF$_3$, —CHF$_2$, —CH$_2$F, sulfamide (—S(=O)$_2$NH$_2$, —S(=O)$_2$NHR$^{20}$, or —S(=O)$_2$NR$^{20}$R$^{21}$), carboxamide (—C(=O)NH$_2$, —C(=O)NHR$^{20}$, or —C(=O)NR$^{20}$R$^{21}$); where R$^{20}$, and R$^{21}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group.

In one version, R$_{13}$-R$_{20}$ are independently selected from —F, —Cl, —Br, —CN, —OCH$_3$, —NO$_2$, —NH$_2$, —NHR$^{20}$, —NR$^{20}$R$^{21}$, —CH$_3$, —CF$_3$, —CHF$_2$, —CH$_2$F, sulfamide (—S(=O)$_2$NH$_2$, —S(=O)$_2$NHR$^{20}$, or —S(=O)$_2$NR$^{20}$R$^{21}$), carboxamide (—C(=O)NH$_2$, —C(=O)NHR$^{20}$, or —C(=O)NR$^{20}$R$^{21}$); where R$^{20}$, and R$^{21}$ are independently selected from a C$_1$-C$_6$ alkyl group, a C$_3$-C$_{20}$ heterocyclic group, or a C$_3$-C$_{20}$ aryl group, preferably a C$_1$-C$_6$ alkyl group; and C$_1$-C$_{10}$ alkyl or C$_1$-C$_{10}$ alkyl substituted with one or more heteroatom containing groups, selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano.

In one version, the R$_{10}$ group is a bond and the R$_{11}$ group is attached directly to the X linker group. In one version, the X group is the ether X1, $R_{10}$ group is a bond, and $R_{11}$ is an unsubstituted or substituted phenyl in which the $R_{10}$ and $R_{12}$ groups are ortho or para to each other; i.e., the linking group L has the formula

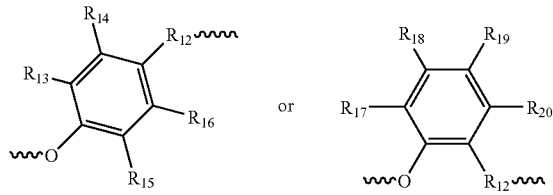

and where $R_{13}$-$R_{20}$ are as described in any version above.

R12 Group: $R_{12}$ is generally any group capable of linking the aryl or heteroaryl group $R_{11}$ to a protectable group in the anti-neoplastic agent and which will yield the anti-neoplastic agent or a cytotoxic derivative of the anti-neoplastic agent upon degradation of the modified anti-neoplastic agent that was released upon reduction of the hypoxic activator.

In one version, $R_{12}$ has the formula —$(CR^{40}R^{41})$—$R^{42}$— where $R^{40}$ and $R^{41}$ are independently selected from —H, $C_1$-$C_{10}$ alkyl or $C_1$-$C_{10}$ alkyl substituted with one or more heteroatom containing groups, selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; and $R^{42}$ is a bond, or —OC(=O)—. In one version, $R_{12}$ has the formula —$(CR^{40}R^{41})$—$R^{42}$— where $R^{40}$ is —H and $R^{41}$ is selected from $C_1$-$C_{10}$ alkyl or $C_1$-$C_{10}$ alkyl substituted with one or more heteroatom containing groups, selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano; and $R^{42}$ is a bond, or —OC(=O)—. In one version, $R^{40}$, $R^{41}$, and $R^{42}$ are as described in any of the prior sentences in this paragraph, which the proviso that $R^{42}$ is —OC(=O)— only when the anti-neoplastic agent is linked to the linking group through the nitrogen of an amine in the anti-neoplastic agent. In one version, $R^{40}$ and $R^{41}$ are hydrogen.

In one version, $R_{12}$ is —$CH_2$— and $R_{12}$ is attached to a hydroxyl group oxygen in the neoplastic agent. In one version, $R_{12}$ is —$CH_2$— and $R_{12}$ is attached to an amine group nitrogen in the neoplastic agent. In one version, $R_{12}$ is —$CH_2$—O—C(=O)— and $R_{12}$ is attached to an amine group nitrogen in the neoplastic agent.

In one version, $R_{12}$ has the formula —$(CR^{40}R^{41})$—$CR^{43}$=$CR^{44}$—$R^{42}$— where $R^{40}$, $R^{41}$ and $R^{42}$ are as described above and $R^{43}$ and $R^{44}$ are independently selected from —H, $C_1$-$C_{10}$ alkyl or $C_1$-$C_{10}$ alkyl substituted with one or more heteroatom containing groups, selected from hydroxyl, ether, thiol, thioether, sulfuric ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; preferably hydroxyl, ether, thiol, thioether, carboxylic acid, carboxylic acid salt, ester, amide, aldehydo, keto, amino, halo, and cyano. In one version, $R_{12}$ has the formula —$(CR^{40}R^{41})$—$CR^{43}$=$CR^{44}$—$R^{42}$— where $R^{40}$, $R^{41}$ and $R^{42}$ are as described above and $R^{43}$ and $R^{44}$ are —H.

Anti-Neoplastic Agents (N)

Generally, the anti-neoplastic agent, N, may be any agent capable of being protected using the hypoxic activator and linking groups described above and that generates a cytotoxic anti-neoplastic agent or modified anti-neoplastic agent upon release after reduction of the hypoxic activator.

In one version, N is a cytotoxic agent having an $IC_{50}$ less than 100 microM, and optionally less than 1 microM, as defined by the NCI screening assay as an $LC_{50}$ after a 24 hr drug treatment of a sensitive cell line. In one version, the cytotoxic agent has an $IC_{50}$ less than 10 nanomolar. In one version, N is doxorubicin. In one version N is doxorubicin linked to the hypoxic activator via a linking group which is such that reduction of the hypoxic activator releases modified doxorubicin having an $IC_{50}$ in the low nanomolar range.

In one version, N is selected from the group consisting of maytansines, enediynes, discodermolides, epothilones, taxanes, calicheamicins, and tedanolides. In another version, N is selected from the group consisting of etoposide, vinblastine, vincristine, topotecan, 5-fluorouracil, AQ4N, and hydroxyurea.

Other anti-neoplastic agents that can incorporated in or released from the protected anti-neoplastic agents include but are not limited to bleomycins, calicheamicins, colchicine, cyclophosphamide, cytarabine, dacarbazine, dactinomycin, daunorubicin, discodermolides, doxorubicin and doxorubicin-like compounds such as epirubicin and derivatives, enediynes, epothilones, etoposide, Combretastatin A-4, fludarabine, 5-fluorouracil or prodrugs thereof such as Xeloda marketed by Roche, hydroxyurea, hydroxyureapentostatin, maytansines, 6-mercaptopurine, methotrexate, mitomycin, mitoxantrone, platinum-containing agents including but not limited to carboplatin and cisplatin, prednisone, procarbazine, taxanes including but not limited docetaxel and paclitaxel, tedanolides, teniposide, 6-thioguanine, topotecan, and vinca alkaloids including but not limited to vinblastine and vincristine.

Other anti-neoplastic agents that can incorporated in or released from the protected anti-neoplastic agents include but are not limited to anti-angiogenic agents, alkylating agents, antimetabolite, microtubulin polymerization perturbers (for example, Taxol), certain natural products, platinum coordination complexes, anthracenediones, substituted ureas, methylhydrazine derivatives, adrenocortical suppressants, certain hormones and antagonists, anti-cancer polysaccharides and certain herb or other plant extracts.

In one version, the anti-neoplastic agents that may be protected using the hypoxic activators and linking groups described herein are the class of cytotoxic antibiotics known as anthracyclines. Anthracyclines include but are not limited to Aclarubicin, Daunorubicin, Doxorubicin, Epirubicin, Idarubicin, Mitoxantrone, Pirarubicin, and Valrubicin, and any analogs of the foregoing. Anthracycline analogs are well known in the art and are included in the class of anthracyclines that may be protected using the hypoxic activators and linking groups described herein.

Other anti-neoplastic agents that can incorporated in or released from the protected anti-neoplastic agents include analogs of any of the forgoing agents described in this section. With their knowledge of the art and the teachings in this patent, one of skill in the art will understand how to identify and synthesize analogs of the foregoing and how to protect analogs of the foregoing to produce a protected anti-neoplastic agent as described in this patent.

Attachment of the anti-neoplastic agent to the Linking group or Hypoxic Activator: The anti-neoplastic agent is attached to the hypoxic activator (Hyp) either directly or through a linking group (L); i.e., the structure of the protected anti-neoplastic agent is Hyp-N or Hyp-L-N. Generally, the hypoxic activator or linking group may be attached to any moiety in the anti-neoplastic agent capable of attachment and that provides a prodrug of the anti-neoplastic agent.

In one version, the hypoxic activator or linking group is attached to a hydroxyl or amine group in the anti-neoplastic agent. In one version, the hydrogen on the hydroxyl group and one or more of the substituents on the amine group are replaced with a bond to a moiety in the hypoxic activator or linking group. In this manner the anti-neoplastic agent may be attached to the hypoxic activator or linking group through a variety of groups including but not limited to ethers, carbamates, carbonates esters, acetals, amides and amines. In one version, the hypoxic activator or linking group is attached to the anti-neoplastic agent through an ether, amine or carbamate.

The anti-neoplastic agent N may be represented as N'-Z, where Z is —OH or —$NR^aR^b$ and N' represents the remainder of the anti-neoplastic agent. $R^a$ and $R^b$ are such that the —$NR^aR^b$ is a primary, secondary or tertiary amine group. Generally, —$NR^aR^b$ is any amine type group capable of bonding to the hypoxic activator or linking group by replacement of one or both of $R^a$ and $R^b$. In one version, Z is —$NH_2$. In one version, Z in —$NHR^a$.

In one version, Z is a hydroxyl and the hydroxyl is bonded to an aromatic group in the anti-neoplastic agent. In one version the aromatic group to which the hydroxyl is bonded is a phenyl or substituted phenyl. The substituted phenyl may be part of a fused ring system.

In one version, upon protection by the hypoxic activator or linking group, the anti-neoplastic agent is attached to the hypoxic activator or linking group in one of the following ways

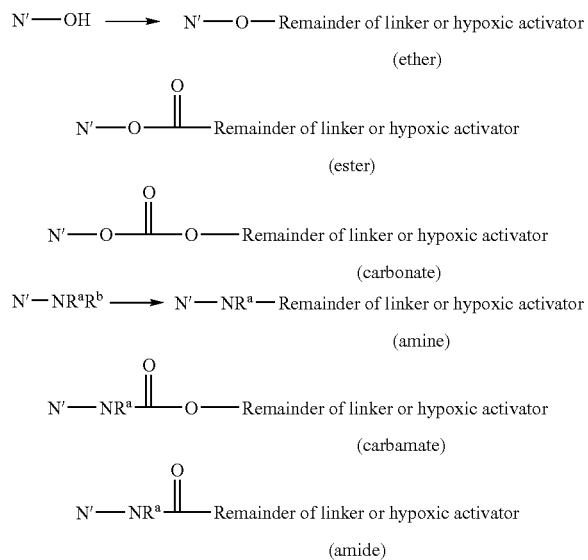

In one version, upon protection by the hypoxic activator or linking group, the anti-neoplastic agent is attached to the hypoxic activator or linking group via either the ether or the carbamate linker as shown above.

In addition to amine nitrogens, other nitrogens in the anti-neoplastic agents may be protected using the hypoxic activators and linking groups described in this patent. Examples of nitrogen groups that may be protected include but are not limited to amide groups, heterocyclic amines (including but not limited to indoles, imidazoles, and benzimidazoles), and the nitrogen of an isoquinoline. In the case of amides, in one version the group directly attached to the anti-neoplastic agent nitrogen is not a carbamate.

In one version, the anti-neoplastic agent

Methods of Treatment Using the Protected Anti-Neoplastic Agents

The protected anti-neoplastic agents may be used in methods for treating cancer. In such methods, an effective amount of a protected anti-neoplastic agent is administered to the subject. Generally, the subject may be any human or non-human mammal. The preferred subject is a human subject. Other particular subjects-include but are not limited to non-human primates dogs, cats, farm animals, horses, In one version, the protected anti-neoplastic agent is administered alone. In one version the protected anti-neoplastic agent is administered in combination with one or more additional anti-cancer agents. In one version the protected anti-neoplastic agent is administered in conjunction with a therapeutic cancer treatment, including but not limited to surgery and radiation. The protected anti-neoplastic agent will typically be administered in a pharmaceutical composition. Various pharmaceutical compositions that may be used are described in the Formulations section of this patent.

The protected anti-neoplastic agents and their pharmaceutical compositions can be used to treat any type of cancer in a subject, particularly in a human subject. Cancers that may be treated include but are not limited to leukemia, breast cancer, skin cancer, bone cancer, liver cancer, brain cancer, cancer of the larynx, gallbladder, pancreas, rectum, parathyroid, thyroid, adrenal, neural tissue, head and neck, stomach, bronchi, kidneys, basal cell carcinoma, squamous cell carcinoma of both ulcerating and papillary type, metastatic skin carcinoma, osteosarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas.

The protected anti-neoplastic agents may particularly be used in the treatment of cancers containing significant areas of hypoxic tissue. Such cancers include but are not limited to lung cancer, especially non-small cell lung cancer, breast cancer, colon cancer, head and neck cancer, ovarian cancer, pancreatic cancer, and prostate cancer. Several of these cancers are discussed for illustrative purposes below. Those of skill in the art will appreciate that cancer chemotherapy often involves the simultaneous or successive administration of a variety of anti-cancer agents, and as discussed further below, the protected anti-neoplastic agents can be used in combination therapies as provided by the methods described herein. Thus, in the description of illustrative cancers containing hypoxic regions amenable to treatment with the protected anti-neoplastic agents, illustrative combination therapies are also described.

Lung cancer affects more than 100,000 males and 50,000 females in the United States, most of whom die within 1 year of diagnosis, making it the leading cause of cancer death. Current protocols for the treatment of lung cancer involve the integration of chemotherapy with or without radiotherapy or surgery. The protected anti-neoplastic agents, including those that release chemotherapeutic agents presently used to treat various forms of lung cancer, can be used to treat lung cancer, for example, by replacing a non-hypoxia-activated form in the combination, and other protected anti-neoplastic agents can be used in existing combination therapies. A variety of combination chemotherapy regimens have been reported for small cell lung cancer, including the combinations consisting of cyclophosphamide, doxorubicin and vincristine (CAV); etoposide and cisplatin (VP-16); and cyclophosphamide, doxorubicin and VP-16 (CAVP-16). Modest survival benefits from combination chemotherapy (etoposide plus cisplatin) treatment have been reported for non-small cell lung cancer. The protected anti-neoplastic agents described in this patent may be based on each of the chemotherapeutic agents listed above.

Likewise, several different cytotoxic drugs have produced at least temporary regression of ovarian cancer. The most active drugs in the treatment of ovarian have been alkylating agents, including cyclophosphamide, ifosfamide, melphalan, chlorambucil, thiotepa, cisplatin, and carboplatin. Current combination therapies for ovarian cancer includes cisplatin or carboplatin in combination with cyclophosphamide at 3- to 4-week intervals for six to eight cycles. The compounds and methods described herein provide prodrug forms of each of these agents, and methods for treating ovarian cancer in which a protected anti-neoplastic agent as described herein is used in such combinations, either to replace an agent or in addition to the agent(s) currently used.

Cancer of the prostate is the most common malignancy in men in the United States and is the second most common cause of cancer death in men above age 55, and this cancer has been reported to consist primarily of hypoxic tissue. Several chemotherapy protocols have been reported for use in late stage disease following relapse after hormonal treatment. Agents for the treatment of prostate cancer include estramustine phosphate, prednimustine, and cisplatin, and prodrug forms of each of these agents is provided by the compounds and methods described herein, as well as methods for treating prostate cancer using such agents. Combination chemotherapy is also used to treat prostate cancer, including treatment with estramustine phosphate plus prednimustine and cisplatin, and 5-fluorouracil, melphalan, and hydroxyurea. The compounds and methods described herein provide prodrug forms of each of these agents, and methods for treating prostate cancer in which a protected anti-neoplastic agent is used in such combinations, either to replace an agent or in addition to the agent(s) currently used.

Cancer of the large bowel is the second most common cause of cancer death in the United States and is likewise a cancer characterized by hypoxic regions. While chemotherapy in patients with advanced colorectal cancer has proven to be of only marginal benefit, 5-fluorouracil is the most effective treatment for this disease. 5-Fluorouracil is useful alone or in combination with other drugs, but is associated with only a 15 to 20 percent likelihood of reducing measurable tumor masses by 50 percent or more. Thus, the hypoxia-activated prodrug form of 5-FU using the compounds and methods described herein, and the methods for treating colon cancer using that prodrug, offer significant therapeutic benefit and potential for meeting the unmet need for better treatment methods for this disease.

In one version of the treatment methods, the protected anti-neoplastic agents may be used in various known approaches to cancer therapy including but not limited to "anti-body-directed enzyme prodrug therapy" (ADEPT), "virus-directed enzyme prodrug therapy (VDEPT), "gene-directed enzyme prodrug therapy" (GDEPT), and "bacteria-directed enzyme prodrug therapy" (BDEPT). The general uses of the protected anti-neoplastic agents are not limited to the foregoing treatment methods.

Formulations, Modes of Administration, Dosages, etc

The protected anti-neoplastic agents will typically be formulated as pharmaceutical formulations for administration to a subject. Described in this section are modes of administration, formulations, and dosages that may be used when treating cancers using the protected anti-neoplastic agents described in this patent.

Administration of the protected anti-neoplastic agents for the treatment of cancer can be effected by any method that enables delivery of the prodrugs to the site of action, the hypoxic region of a tumor. Many cancer drugs are administered by intravenous injection, and the protected anti-neoplastic agent may be formulated for such administration, including not only ready-for-injection formulations but also lyophilized or concentrated formulations that must be rehydrated or diluted, respectively, prior to injection. In addition to these formulations, the protected anti-neoplastic agent may be formulated for administration by oral routes, intraduodenal routes, parenteral injection (including intravenous, subcutaneous, intramuscular, intravascular or infusion), topical, and rectal routes. Those of skill in the art will recognize that the protected anti-neoplastic agent can be activated by bacteria in the gut. If such activation is not desired, then the practitioner may employ a route of administration or a formulation that results in absorption of the protected anti-neoplastic agent prior to its entry into the large intestine or colon. The actual route of administration and corresponding formulation of the protected anti-neoplastic agents will depend on the type of cancer being treated, the protected anti-neoplastic agent selected for administration, the severity of the cancer, and the age, weight, and condition of the patient, among other factors.

In similar fashion, the amount of the protected anti-neoplastic agent administered, and thus the amount of the protected anti-neoplastic agent contained in the dose administered and the product comprising that dose, will be dependent on the subject being treated, the severity of the cancer, localization of the cancer, the rate of administration, the disposition of the prodrug (e.g., solubility and cytotoxicity), the cytotoxic agent released by the protected anti-neoplastic agent, and the discretion of the prescribing physician. However, an effective dosage is typically in the range of about 0.001 to about 100 mg per kg body weight, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect; larger doses can also be divided into several small doses for administration throughout the day.

A formulation of a protected anti-neoplastic agent may, for example, be in a form suitable for oral administration as a tablet, capsule, pill powder, sustained release formulation, solution, and suspension; for parenteral injection as a sterile solution, suspension or emulsion; for topical administration as an ointment or cream; and for rectal administration as a suppository. A formulation of a protected anti-neoplastic agent may be in unit dosage forms suitable for single administration of precise dosages and will typically include a conventional pharmaceutical carrier or excipient.

Suitable pharmaceutical carriers include inert diluents or fillers, water and various organic solvents. The pharmaceutical compositions may, if desired, contain additional ingredients such as flavorings, binders, excipients, and the like. Thus for oral administration, tablets containing various excipients, such as citric acid may be employed together with various disintegrants, such as starch, alginic acid, and certain complex silicates, and with binding agents such as sucrose, gelatin and acacia. Additionally, lubricating agents such as magnesium stearate, sodium lauryl sulfate, and talc can be used to prepare the tablet forms of formulations of the protected anti-neoplastic agents described herein. Solid compositions of a similar type can be employed in soft and hard filled gelatin capsules. Preferred materials, therefore, include lactose or milk sugar and high molecular weight polyethylene glycols. When aqueous suspensions or elixirs are desired for oral administration, the prodrug therein may be combined with various sweetening or flavoring agents, coloring matters or dyes and, if desired, emulsifying agents or suspending agents, together with diluents such as water, ethanol, propylene glycol, glycerin, or combinations thereof.

Exemplary parenteral administration forms include solutions or suspensions of the hypoxia-activated prodrug in sterile aqueous solutions, for example, aqueous propylene glycol or dextrose solutions. Such dosage forms can be suitably buffered, if desired.

Methods of preparing various pharmaceutical compositions with a specific amount of active drug are known, or will be apparent, to those skilled in this art in view of this disclosure. For examples, see Remington's Pharmaceutical Sciences, Mack Publishing Company, Philadelphia, Pa., 17$^{th}$ Edition (1984).

Methods of Making the Protected Anti-Neoplastic Agents

The protected anti-neoplastic agents described in this patent may be made by a variety of methods. Given the synthesis methods described in the examples below and their knowledge of synthetic medicinal chemistry, one of skill in the art will be able to synthesize the protected anti-neoplastic agents in a straightforward manner.

Combination Therapies

In one version of the method of treating cancer using the protected anti-neoplastic agents, a protected anti-neoplastic agent is administered in combination with an effective amount of one or more chemotherapeutic agents, an effective amount of radiotherapy, an appropriate surgery procedure, or any combination of such additional therapies.

When a protected anti-neoplastic agent is used in combination with one or more of the additional therapies, the protected anti-neoplastic agent and additional therapy may be administered at the same time or may be administered separately. For example, if a protected anti-neoplastic agent is administered with an additional chemotherapeutic agent, the two agents may be administered simultaneously or may be administered sequentially with some time between administrations. One of skill in the art will understand methods of administering the agents simultaneously and sequentially and possible time periods between administration.

The agents may be administered as the same or different formulations and may be administered via the same or different routes.

Chemotherapeutic agents that may be used in combination with the protected anti-neoplastic agents described in this patent include but are not limited to busulfan, improsulfan, piposulfan, benzodepa, carboquone, 2-deoxy-D-glucose, lonidamine, meturedepa, uredepa, altretamine, imatinib, triethylenemelamine, triethylenephosphoramide, triethylenethiophosphoramide, trimethylolomelamine, chlorambucil, chlornaphazine, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, mycophenolic acid, nogalamycin, olivomycin, peplomycin, plicamycin, porfiromycin, puromycin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, 5-fluorouracil, tegafur, L-asparaginase, pulmozyme, aceglatone, aldophosphamide glycoside, aminolevulinic acid, amasacrine, bestrabucil, bisantrene, carboplatin, defofamide, demecolcine, diaziquone, elformithine, elliptinium acetate, etoglucid, flutamide, gallium nitrate, hydroxyurea, interferon-alpha, interferon-beta, interferon-gamma, interleukin-2, lentinan, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, cyclophosphamide, and vincristine. Other chemotherapeutic agents that may be used include platinum derivatives, including but not limited to cis platinum, carboplatin, and oxoplatin.

In one version, the protected anti-neoplastic agents described in this patent may be used in combination with an antiangeogenisis inhibitor including but not limited to Avastin and similar therapeutics. In one version of the combination treatment methods, a subject is treated with an antiangeogenisis inhibitor and subsequently treated with a protected anti-neoplastic agent. In one version of the combination treatment methods, a subject is treated with an antiangeogenisis inhibitor and subsequently treated with a protected anti-neoplastic agent with another chemotherapeutic agent, including but not limited to C is platinum. In one version of these combination methods of treatment using an antiangeogenisis inhibitor, the method is used to treat breast cancer.

In another version, a protected anti-neoplastic agent is administered with an anti-cancer agent that acts, either directly or indirectly, to inhibit hypoxia-inducible factor 1 alpha (HIF1a) or to inhibit a protein or enzyme, such as a glucose transporter or VEGF, whose expression or activity is increased upon increased HIF1a levels. HIF1a inhibitors suitable for use in this version of the methods and compositions described herein include P13 kinase inhibitors; LY294002; rapamycin; histone deacetylase inhibitors such as [(E)-(1S, 4S,10S,21R)-7-[(Z)-ethylidene]-4,21-diisopropyl-2-oxa-12, 13-dithia-5,8,20,23-tetraazabicyclo-[8,7,6]-tricos-16-ene-3, 6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-1) inhibitors such as PD98059 (2'-amino-3'-methoxyflavone); PX-12 (1-methylpropyl 2-imidazolyl disulfide); pleurotin PX-478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; camptothecins; and YC-1, a compound described in *Biochem. Pharmacol.*, 15 Apr. 2001, 61(8):947-954, incorporated herein by reference, and its derivatives.

In another version, a protected anti-neoplastic agent is administered with an anti-angiogenic agent, including but not limited to anti-angiogenic agents selected from the group consisting of angiostatin, an agent that inhibits or otherwise antagonizes the action of VEGF, batimastat, captopril, cartilage derived inhibitor, genistein, endostatin, interleukin, lavendustin A, medroxypregesterone acetate, recombinant human platelet factor 4, Taxol, tecogalan, thalidomide, thrombospondin, TNP-470, and Avastin. Other useful angiogenesis inhibitors for purposes of the combination therapies provided by the present methods and compositions described herein include Cox-2 inhibitors like celecoxib (Celebrex), diclofenac (Voltaren), etodolac (Lodine), fenoprofen (Nalfon), indomethacin (Indocin), ketoprofen (Orudis, Oruvail), ketoralac (Toradol), oxaprozin (Daypro), nabumetone (Relafen), sulindac (Clinoril), tolmetin (Tolectin), rofecoxib (Vioxx), ibuprofen (Advil), naproxen (Aleve, Naprosyn), aspirin, and acetaminophen (Tylenol). In addition, because pyruvic acid plays an important role in angiogenesis, pyruvate mimics and glycolytic inhibitors like halopyrnvates, including bromopyruvate, can be used in combination with an anti-angiogenic compound and a protected anti-neoplastic agent to treat cancer. In another version, a protected anti-neoplastic agent is administered with an anti-angiogenic agent and another anti-cancer agent, including but not limited to a cytotoxic agent selected from the group consisting of alkylators, Cisplatin, Carboplatin, and inhibitors of microtubule assembly, to treat cancer.

In addition to the combination of a protected anti-neoplastic agent with the agents described above, the present methods and compositions described herein provides a variety of synergistic combinations of a protected anti-neoplastic agent and other anti-cancer drugs. Those of skill in the art can readily determine the anti-cancer drugs that act "synergistically" with a protected anti-neoplastic agent as described herein. For example, the reference Vendetti, "Relevance of Transplantable Animal-Tumor Systems to the Selection of New Agents for Clinical Trial," Pharmacological Basis of Cancer Chemotherapy, Williams and Wilkins, Baltimore, 1975, and Simpson Herren et al., 1985, "Evaluation of In Vivo Tumor Models for Predicting Clinical Activity for Anticancer Drugs," *Proc. Am. Assoc. Cancer Res.* 26: 330, each of which is incorporated herein by reference, describe methods to aid in the determination of whether two drugs act synergistically. While synergy is not required for therapeutic benefit in accordance with the methods of described herein, synergy can improve therapeutic outcome. Two drugs can be said to possess therapeutic synergy if a combination dose regimen of the two drugs produces a significantly better tumor cell kill than the sum of the single agents at optimal or maximum tolerated doses. The "degree of synergy" can be defined as net log of tumor cell kill by the optimum combination regimen minus net log of tumor cell kill by the optimal dose of the most active single agent. Differences in cell kill of greater than ten-fold (one log) are considered conclusively indicative of therapeutic synergy.

When a protected anti-neoplastic agent is used with another anti-cancer agent, a protected anti-neoplastic agent will, at least in some versions, be administered prior to the initiation of therapy with the other drug or drugs and administration will typically be continued throughout the course of treatment with the other drug or drugs. In some versions, the drug co-administered with a protected anti-neoplastic agent will be delivered at a lower dose, and optionally for longer periods, than would be the case in the absence of a protected anti-neoplastic agent administration. Such "low dose" therapies can involve, for example, administering an anti-cancer drug, including but not limited to paclitaxel, docetaxel, doxorubicin, cisplatin, or carboplatin, at a lower than approved dose and for a longer period of time together with a protected anti-neoplastic agent administered in accordance with the methods described herein. These methods can be used to improve patient outcomes over currently practiced therapies by more effectively killing cancer cells or stopping cancer cell growth as well as diminishing unwanted side effects of the other therapy. In other versions, the other anti-cancer agent or agents will be administered at the same dose levels used when a protected anti-neoplastic agent is not co-administered. Thus, when employed in combination with a protected anti-neoplastic agent, the additional anti-cancer agent(s) are dosed using either the standard dosages employed for those agents when used without a protected anti-neoplastic agent or are less than those standard dosages. The administration of a protected anti-neoplastic agent in accordance with the methods described herein can therefore allow the physician to treat cancer with existing (or later approved) drugs at lower doses (than currently used), thus ameliorating some or all of the toxic side effects of such drugs. The exact dosage for a given patient varies from patient to patient, depending on a number of factors including the drug combination employed, the particular disease being treated, and the condition and prior history of the patient, but can be determined using only the skill of the ordinarily skilled artisan in view of the teachings herein.

Specific dose regimens for known and approved antineoplastic agents (i.e., the recommended effective dose) are known to physicians and are given, for example, in the product descriptions found in the Physician's Desk Reference 2003, (Physicians' Desk Reference, 57th Ed) Medical Economics Company, Inc., Oradell, N.J. and/or are available from the Federal Drug Administration. Illustrative dosage regimens for certain anti-cancer drugs are also provided below.

Cancer drugs can be classified generally as alkylators, anthracyclines, antibiotics, aromatase inhibitors, bisphosphonates, cyclo-oxygenase inhibitors, estrogen receptor modulators, folate antagonists, inorganic aresenates, microtubule inhibitors, modifiers, nitrosoureas, nucleoside analogs, osteoclast inhibitors, platinum containing compounds, retinoids, topoisomerase 1 inhibitors, topoisomerase 2 inhibitors, and tyrosine kinase inhibitors. In accordance with the methods described herein, a protected anti-neoplastic agent can be co-administered with any anti-cancer drug from any of these classes or can be administered prior to or after treatment with any such drug or combination of such drugs. In addition, a protected anti-neoplastic agent can be administered in combination with a biologic therapy (e.g., treatment with interferons, interleukins, colony stimulating factors and monoclonal antibodies). Biologics used for treatment of cancer are known in the art and include, for example, trastuzumab (Herceptin), tositumomab and $^{131}$I Tositumomab (Bexxar), rituximab (Rituxan). In one version, however, the anti-cancer drug co-administered with a protected anti-neoplastic agent is not a topoisomerase inhibitor.

Alkylators useful in the practice of the methods described herein include but are not limited to busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), and temozolamide (Temodar). In accordance with the methods described herein a protected anti-neoplastic agent is co-administered with an alkylator to treat cancer. In one version, the cancer is chronic myelogenous leukemia, multiple myeloma, or anaplastic astrocytoma. As one example, the compound 2-bis[(2-chloroethyl)amino]tetrahydro-2H-1,3,2-oxazaphosphorine, 2-oxide, also commonly known as cyclophosphamide, is an alkylator used in the treatment of Stages III and IV malignant lymphomas, multiple myeloma, leukemia, mycosis fungoides, neuroblastoma, ovarian adenocarcinoma, retinoblastoma, and carcinoma of the breast. Cyclophosphamide is administered for induction therapy in doses of 1500-1800 mg/m$^2$ that are administered intravenously in divided doses over a period of three to five days; for maintenance therapy, 350-550 mg/m$^2$ are administered every 7-10 days, or 110-185 mg/m$^2$ are administered intravenously twice weekly. In accordance with the methods described herein, a protected anti-neoplastic agent is co-administered with cyclosphosphamide administered at such doses or at lower doses and/or for a longer duration than normal for administration of cyclosphosphamide alone.

Anthracyclines useful in the practice of the methods described herein, include but are not limited to doxorubicin (Adriamycin, Doxil, Rubex), mitoxantrone Novantrone), idarubicin (Idamycin), valrubicin (Valstar), and epirubicin (Ellence). In accordance with the methods described herein a protected anti-neoplastic agent is co-administered with an anthracycline to treat cancer. In one version, the cancer is acute nonlymphocytic leukemia, Kaposi's sarcoma, prostate cancer, bladder cancer, metastatic carcinoma of the ovary, and breast cancer. As one example the compound (8S,10S)-10-[(3-Amino-2,3,6-trideoxy-.alpha.-L-lyxo-hexopyranosyl) oxy]-8-glycoloyl-7,8,9,10-tetrahydro-6,8,11-trihydroxy-1-methoxy-5,12-naphthacenedione, more commonly known as doxorubicin, is a cytotoxic anthracycline antibiotic isolated from cultures of *Streptomyces peucetius* var. *caesius*. Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma. Doxorubicin is typically administered in a dose in the range of 30-75 mg/m$^2$ as a single intravenous injection administered at 21-day intervals; weekly intravenous injection at doses of 20 mg/m$^2$; or 30 mg/m$^2$ doses on each of three successive days repeated every four weeks. In accordance with the methods of the methods described herein, a protected anti-neoplastic agent is co-administered starting prior to and continuing after the administration of doxorubicin at such doses (or at lower doses).

Antibiotics useful in the practice of the methods described herein include but are not limited to dactinomycin, actinomycin D (Cosmegen), bleomycin (Blenoxane), daunorubicin, and daunomycin (Cerubidine, DanuoXome). In accordance with the methods described herein a protected anti-neoplastic agent is co-administered with an antibiotic to treat cancer. In one version, the cancer is a cancer selected from the group consisting of acute lymphocytic leukemia, other leukemias, and Kaposi's sarcoma.

Aromatase inhibitors useful in the practice of the methods described herein include but are not limited to anastrozole (Arimidex) and letroazole (Femara). In accordance with the methods described herein a protected anti-neoplastic agent is co-administered with an aromatase inhibitor to treat cancer. In one version, the cancer is breast cancer.

Bisphosphonate inhibitors useful in the practice of the methods described herein include but are not limited to zoledronate (Zometa). In accordance with the methods described herein a protected anti-neoplastic agent is co-administered with a biphosphonate inhibitor to treat cancer. In one version, the cancer is a cancer selected from the group consisting of multiple myeloma, bone metastases from solid tumors, or prostate cancer.

Cyclo-oxygenase inhibitors useful in the practice of the methods described herein include but are not limited to celecoxib (Celebrex). In accordance with the methods described herein a protected anti-neoplastic agent is co-administered with a cyclo-oxygenase inhibitor to treat cancer. In one version, the cancer is colon cancer or a pre-cancerous condition known as familial adenomatous polyposis.

Estrogen receptor modulators useful in the practice of the methods described herein include but are not limited to tamoxifen (Nolvadex) and fulvestrant (Faslodex). In accordance with the methods described herein a protected anti-neoplastic agent is co-administered with an estrogen receptor modulator to treat cancer. In one version, the cancer is breast cancer or the treatment is administered to prevent the occurrence or reoccurrence of breast cancer.

Folate antagonists useful in the practice of the methods described herein include but are not limited to methotrexate and tremetrexate. In accordance with the methods described herein a protected anti-neoplastic agent is co-administered with a folate antagonist to treat cancer. In one version, the cancer is osteosarcoma. As one example, the compound N-[4-[[(2,4-diamino-6-pteridinyl)methyl methylamino]benzoyl]-L-glutamic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides. Methotrexate is administered as follows. For choriocarcinoma, intramuscular injections of doses of 15 to 30 mg are administered daily for a five-day course, such courses repeated as needed with rest period of one or more weeks interposed between courses of therapy. For leukemias, twice weekly intramuscular injections are administered in doses of 30 mg/m$^2$. For mycosis fungoides, weekly intramuscular injections of doses of 50 mg or, alternatively, of 25 mg are administered twice weekly. In accordance with the methods described herein, a protected anti-neoplastic agent is co-administered with methotrexate administered at such doses (or at lower doses). 5-Methyl-6-[[(3,4,5-trimethoxyphenyl)-amino]methyl]-2,4-quinazolinediamine (commonly known as trimetrexate) is another antifolate drug that can be co-administered with a protected anti-neoplastic agent.

Inorganic arsenates useful in the practice of the methods described herein include but are not limited to arsenic trioxide (Trisenox). In accordance with the methods described herein a protected anti-neoplastic agent is co-administered with an inorganic arsenate to treat cancer. In one version, the cancer is refractory acute promyelocytic leukemia (APL).

Microtubule inhibitors (as used herein, a "microtubule inhibitor" is any agent that interferes with the assembly or disassembly of microtubules) useful in the practice of the methods described herein include but are not limited to vincristine (Oncovin), vinblastine (Velban), paclitaxel (Taxol, Paxene), vinorelbine (Navelbine), docetaxel (Taxotere), epothilone B or D or a derivative of either, and discodermolide or its derivatives. In accordance with the methods described herein a protected anti-neoplastic agent is co-administered with a microtubule inhibitor to treat cancer. In one version, the cancer is ovarian cancer, breast cancer, non-small cell lung cancer, Kaposi's sarcoma, and metastatic cancer of breast or ovary origin. As one example, the compound 22-oxo-vincaleukoblastine, also commonly known as vincristine, is an alkaloid obtained from the common periwinkle plant (*Vinca rosea*, Linn.) and is useful in the treatment of acute leukemia. It has also been shown to be useful in combination with other oncolytic agents in the treatment of Hodgkin's disease, lymphosarcoma, reticulum-cell sarcoma, rhabdomyosarcoma, neuroblastoma, and Wilm's tumor. Vincristine is administered in weekly intravenous doses of 2 $mg/m^2$ for children and 1.4 $mg/m^2$ for adults. In accordance with the methods described herein, a protected anti-neoplastic agent is co-administered with vincristine administered at such doses. In one version, a protected anti-neoplastic agent is not administered prior to treatment with a microtubule inhibitor, such as a taxane, but rather, administration of a protected anti-neoplastic agent is administered simultaneously with or within a few days to a week after initiation of treatment with a microtubule inhibitor.

Modifiers useful in the practice of the methods described herein include but are not limited to Leucovorin (Wellcovorin), which is used with other drugs such as 5-fluorouracil to treat colorectal cancer. In accordance with the methods described herein a protected anti-neoplastic agent is co-administered with a modifier and another anti-cancer agent to treat cancer. In one version, the cancer is colon cancer. In one version, the modifier is a compound that increases the ability of a cell to take up glucose, including but not limited to the compound N-hydroxyurea. N-hydroxyurea has been reported to enhance the ability of a cell to take up 2-deoxyglucose (see the reference Smith et al., 1999, Cancer Letters 141: 85, incorporated herein by reference), and administration of N-hydroxyurea at levels reported to increase a protected anti-neoplastic agent uptake or to treat leukemia together with administration of a protected anti-neoplastic agent as described herein is one version of the therapeutic methods provided herein. In another such version, a protected anti-neoplastic agent is co-administered with nitric oxide or a nitric oxide precursor, such as an organic nitrite or a spermineNONOate, to treat cancer, as the latter compounds stimulate the uptake of glucose and so stimulate the uptake of a protected anti-neoplastic agent.

Nitrosoureas useful in the practice of the methods described herein include but are not limited to procarbazine (Matulane), lomustine, CCNU (CeeBU), carmustine (BCNU, BiCNU, Gliadel Wafer), and estramustine (Emcyt). In accordance with the methods described herein a protected anti-neoplastic agent is co-administered with a nitrosourea to treat cancer. In one version, the cancer is prostate cancer or glioblastoma, including recurrent glioblastoma multiforme.

Nucleoside analogs useful in the practice of the methods described herein include but are not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), pentostatin (Nipent), cladribine (Leustatin, 2-CdA), gemcitabine (Gemzar), and capecitabine (Xeloda). In accordance with the methods described herein a protected anti-neoplastic agent is co-administered with a nucleoside analog to treat cancer. In one version, the cancer is B-cell lymphocytic leukemia (CLL), hairy cell leukemia, adenocarcinoma of the pancreas, metastatic breast cancer, non-small cell lung cancer, or metastatic colorectal carcinoma. As one example, the compound 5-fluoro-2,4(1H,3H)-pyrimidinedione, also commonly known as 5-fluorouracil, is an antimetabolite nucleoside analog effective in the palliative management of carcinoma of the colon, rectum, breast, stomach, and pancreas in patients who are considered incurable by surgical or other means. 5-Fluorouracil is administered in initial therapy in doses of 12 $mg/m^2$ given intravenously once daily for 4 successive days with the daily dose not exceeding 800 mg. If no toxicity is observed at any time during the course of the therapy, 6 mg/kg are given intravenously on the 6th, 8th, 10th, and 12th days. No therapy is given on the 5th, 7th, 9th, or 11th days. In poor risk patients or those who are not in an adequate nutritional state, a daily dose of 6 mg/kg is administered for three days, with the daily dose not exceeding 400 mg. If no toxicity is observed at any time during the treatment, 3 mg/kg may be given on the 5th, 7th, and 9th days. No therapy is given on the 4th, 6th, or 8th days. A sequence of injections on either schedule constitutes a course of therapy. In accordance with the methods described herein, a protected anti-neoplastic agent is co-administered with 5-FU administered at such doses or with the prodrug form Xeloda with correspondingly adjusted doses. As another example, the compound 2-amino-1,7-dihydro-6H-purine-6-thione, also commonly known as 6-thioguanine, is a nucleoside analog effective in the therapy of acute non-pymphocytic leukemias. 6-Thioguanine is orally administered in doses of about 2 mg/kg of body weight per day. The total daily dose may be given at one time. If after four weeks of dosage at this level there is no improvement, the dosage may be cautiously increased to 3 mg/kg/day. In accordance with the methods described herein, a protected anti-neoplastic agent is co-administered with 6-TG administered at such doses (or at lower doses).

Osteoclast inhibitors useful in the practice of the methods described herein include but are not limited to pamidronate (Aredia). In accordance with the methods described herein a protected anti-neoplastic agent is co-administered with an osteoclast inhibitor to treat cancer. In one version, the cancer is osteolytic bone metastases of breast cancer, and one or more additional anti-cancer agents are also co-administered with a protected anti-neoplastic agent.

Platinum compounds useful in the practice of the methods described herein include but are not limited to cisplatin (Platinol) and carboplatin (Paraplatin). In accordance with the methods described herein a protected anti-neoplastic agent is co-administered with a platinum compound to treat cancer. In one version, the cancer is metastatic testicular cancer, metastatic ovarian cancer, ovarian carcinoma, and transitional cell bladder cancer. As one example, the compound cis-Diaminedichloroplatinum (II), commonly known as cisplatin, is useful in the palliative treatment of metastatic testicular and ovarian tumors, and for the treatment of transitional cell bladder cancer which is not amenable to surgery or radiotherapy. Cisplatin, when used for advanced bladder cancer, is administered in intravenous injections of doses of 50-70 $mg/m^2$ once every three to four weeks. In accordance with the methods described herein, a protected anti-neoplastic agent is co-administered with cisplatin administered at these doses (or at lower doses). One or more additional anti-cancer agents can be co-administered with the platinum compound and a protected anti-neoplastic agent. As one example, Platinol, Blenoxane, and Velbam may be co-administered with a protected anti-neoplastic agent. As another example, Platinol and Adriamycin may be co-administered with a protected anti-neoplastic agent.

Retinoids useful in the practice of the methods described herein include but are not limited to tretinoin, ATRA (Vesanoid), alitretinoin (Panretin), and bexarotene (Targretin). In accordance with the methods described herein a protected anti-neoplastic agent is co-administered with a retinoid to treat cancer. In one version, the cancer is a cancer selected from the group consisting of APL, Kaposi's sarcoma, and T-cell lymphoma.

Topoisomerase 1 inhibitors useful in the practice of the methods described herein include but are not limited to topotecan (Hycamtin) and irinotecan (Camptostar). In accordance with the methods described herein a protected anti-neoplastic agent is co-administered with a topoisomerase 1 inhibitor to treat cancer. In one version, the cancer is metastatic carcinoma of the ovary, colon, or rectum, or small cell lung cancer. As noted above, however, in one version of the methods described herein, administration of a protected anti-neoplastic agent either precedes or follows, or both, administration of a topoisomerase 1 inhibitor but is not administered concurrently therewith.

Topoisomerase 2 inhibitors useful in the practice of the methods described herein include but are not limited to etoposide, VP-16 (Vepesid), teniposide, VM-26 (Vumon), and etoposide phosphate (Etopophos). In accordance with the methods described herein a protected anti-neoplastic agent is co-administered with a topoisomerase 2 inhibitor to treat cancer. In one version, the cancer is a cancer selected from the group consisting of refractory testicular tumors, refractory acute lymphoblastic leukemia (ALL), and small cell lung cancer. As noted above, however, in one version of the methods described herein, administration of a protected anti-neoplastic agent either precedes or follows, or both, administration of a topoisomerase 2 inhibitor but is not administered concurrently therewith.

Tyrosine kinase inhibitors useful in the practice of the methods described herein include but are not limited to imatinib (Gleevec). In accordance with the methods described herein a protected anti-neoplastic agent is co-administered with a tyrosine kinase inhibitor to treat cancer. In one version, the cancer is CML or a metastatic or unresectable malignant gastrointestinal stromal tumor.

Thus, drscribed herein are methods of treating cancer in which a protected anti-neoplastic agent or a pharmaceutically acceptable salt thereof and one or more additional anti-cancer agents are administered to a patient. Specific versions of such other anti-cancer agents include without limitation 5-methyl-6-[[(3,4,5-trimethoxyphenyl)amino]-methyl]-2,4-quinazolinediamine or a pharmaceutically acceptable salt thereof, (8S,10S)-10-(3-amino-2,3,6-trideoxy-alpha-L-lyxo-hexopyranosyl)oxy]-8-glycoloyl-7,8,9,10-tetrahydro-6,8,11-trihydroxy-1-methoxy-5,12-naphthacenedione or a pharmaceutically acceptable salt thereof; 5-fluoro-2,4(1H,3H)-pyrimidinedione or a pharmaceutically acceptable salt thereof; 2-amino-1,7-dihydro-6H-purine-6-thione or a pharmaceutically acceptable salt thereof; 22-oxo-vincaleukoblastine or a pharmaceutically acceptable salt thereof; 2-bis[(2-chloroethyl)amino]tetrahydro-2H-1,3,2-oxazaphosphorine, 2-oxide, or a pharmaceutically acceptable salt thereof; N-[4-[[(2,4-diaminno-6-pteridinyl)methyl]-methylamino]benzoyl]-L-glutamic acid, or a pharmaceutically acceptable salt thereof; or cis-diamminedichloroplatinum (II). The methods described herein are generally applicable to all cancers but have particularly significant therapeutic benefit in the treatment of solid tumors, which are characterized by extensive regions of hypoxic tissue. Particular cancers that can be treated with the methods described herein are discussed in the following section.

EXAMPLES

The following examples illustrate various aspects of the compounds, compositions and methods described in this patent. These examples are in no way intended to limit the scope of the claims.

Example 1

Synthesis of Nitroimidazole-Based Hypoxia Activator Moieties

This example illustrates methods for the synthesis of nitroimidazole-based, hypoxic activator moiety intermediates useful in methods described herein for synthesizing protected anti-neoplastic agents. Additional synthesis methods are given in Example 7. In part A, an illustrative method for the synthesis of

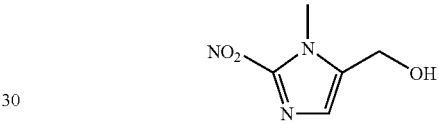

N-1-methyl-2-nitro-5-hydroxymethyl imidazole from ethyl sarcosine hydrochloride is provided. (3-Methyl-2-nitro-3H-imidazol-4-yl)-methanol is an example of what is refered to in this patent as a "nitroimidazole primary alcohol." Because protected anti-neoplastic agents containing this hypoxic activator may in some cells be activated even under normoxic conditions due to the attack on the primary carbon of the alcohol by glutathione-S-transferase or via a similar mechanism, and because further substitution of this carbon may reduce or eliminate such unwanted activation, also described in this patent are secondary alcohol versions which are referred to as "the nitroimidazole secondary alcohols". Synthesis of such nitroimidazole secondary alcohols is presented in part B of this example.

Part A. Synthesis of a Nitroimidazole Primary Alcohol. The following scheme provides a method for the synthesis of the nitroimidazole primary alcohol (compound 2 in the scheme) from ethyl sarcosine. In this scheme, ethylsarcosine hydrochloride is first converted to ethyl-N-formyl-C-formyl sarcosine hydrochloride; a suitable method for such conversion is described in the reference Jones, 1949, *J. Am. Chem. Soc.* 71: 644, incorporated herein by reference. The latter compound is then converted to a compound referred to in this scheme as "the nitroimidazole ester" (compound 1 in the scheme); a suitable method for such conversion is described in the reference Asato et al., 1972, *J. Med. Chem.* 15: 1086, incorporated herein by reference. Then, the nitroimidazole ester is converted to the nitroimidazole primary alcohol; a suitable method for such conversion is described in Parveen et al., 1999, *Bioorg. Med. Chem. Lett.* 9: 2031, incorporated herein by reference.

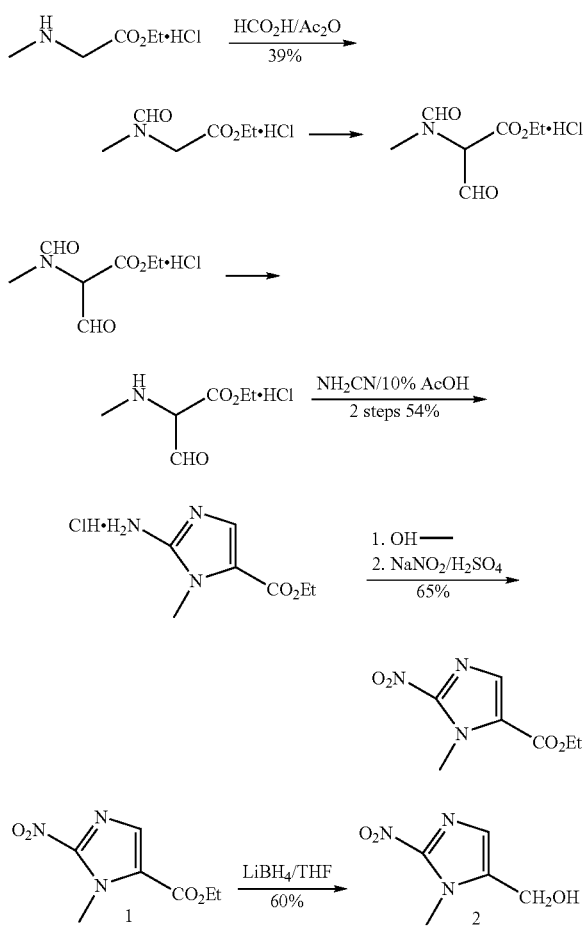

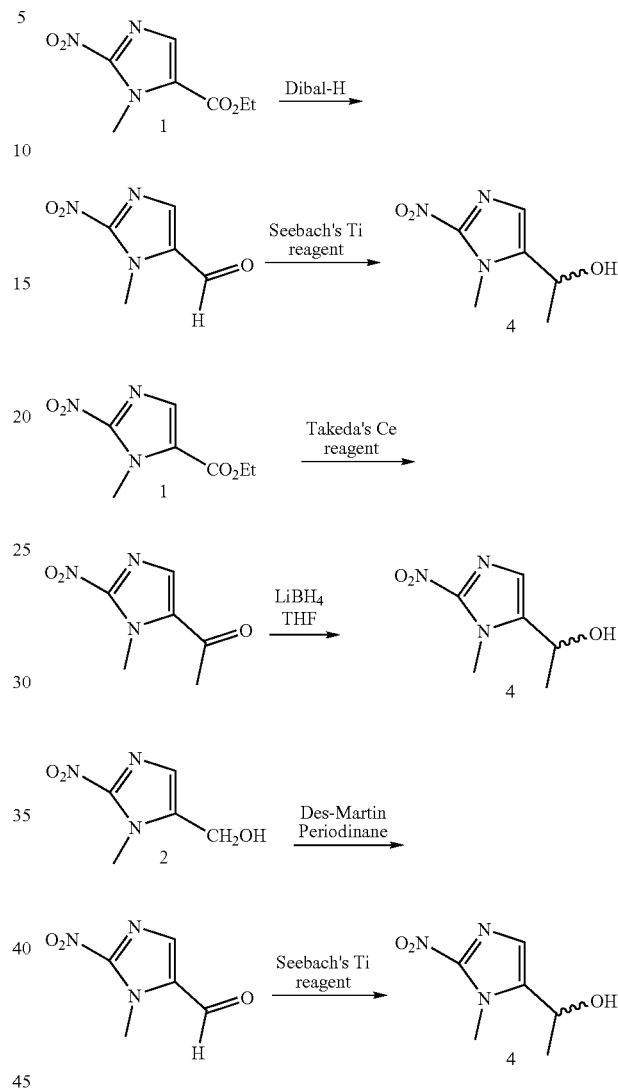

theses, Volume CV 8, page 495 et seq., and the references cited therein, incorporated herein by reference).

All the examples shown below have the nitroimidazole moiety bearing a methyl group at the 1 position. This methyl group can alternatively be an alkyl group bearing steric hinderance or other groups as described in this patent. Such analogs would be useful in reducing the reactivity of the 2 nitro group toward two electron reduction in vivo by oxygen insensitive enzymes such as DT diaphorase. By reducing the ability of the protected anti-neoplastic agents to be activated by oxygen insensitive enzymes, the selectivity to hypoxic tumors will be enhanced. Such hindered analogs can be synthesized by using the scheme above and substituting the N methylglycine ester with a hindered N alkyl glycine ester such as N neopentyl glycine ester. Other hindered groups can be envisioned including but not limited to t-butyl, cyclohexyl, cyclopentyl, isopropyl or any heteroatom substituted variant.

Part B. Synthesis of a Nitroimidazole Secondary Alcohol. As noted above, described in this section are the nitroimidazole secondary alcohols, and methods for its synthesis. In three different illustrative methods, as shown in the schemes below, either the nitroimidazole ester (compound 1 in the scheme in part A and in the schemes below) or the nitroimidazole primary alcohol (compound 2 in the scheme in part A and in the schemes below) is converted to the nitroimidazole secondary alcohol using either Cerium reagents (second scheme below; see Takeda et al., *Organic Syntheses*, Volume 76, page 228 et seq. and the references cited therein, incorporated herein by reference) or Titanium reagents (first and third schemes below (see Imwinkelried et al. *Organic Syn-*

The nitroimidazole primary and secondary alcohols (compound A, below) may in turn be converted to the chloroformate (compound B, below), and the chloromethyl ether (compound C, below) compounds described herein, shown below.

R=H or Me

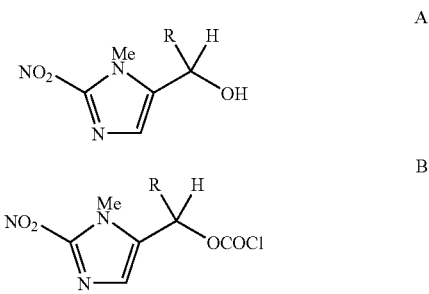

-continued

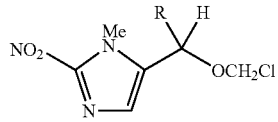
C

Compounds A, B, and C, above, are useful as intermediates in the synthesis of the hypoxia-activated protected anti-neoplastic agents, where they serve to block hydroxy, amino, and other groups in the protected anti-neoplastic agent.

Example 2

Etoposide

The following is a prophetic example of an anti-neoplastic agent containing a phenolic group.

The etoposide antitumor drug can be specifically alkylated at its phenolic position using the 1-methyl-2-nitro-5-bromomethyl-imidazole reagent described in Example 1 under mild condition of a moderate base such as potassium carbonate in an anhydrous solvent such as DMF. Alternatively, the above alkylation can be effected under Mitsunobu conditions between the methyl-2-nitro-5-hydroxymethyl-imidazole and etoposide using triphenyl phosphine and isopropyl azodicarboxylate in DMF. An analogous reaction and experimentals are provided in Toki, et. al., Journal of Organic Chemistry, 2002, 67, 1866-1872 in Example 1. The following structural formula presents a nonlimiting example of such a structure.

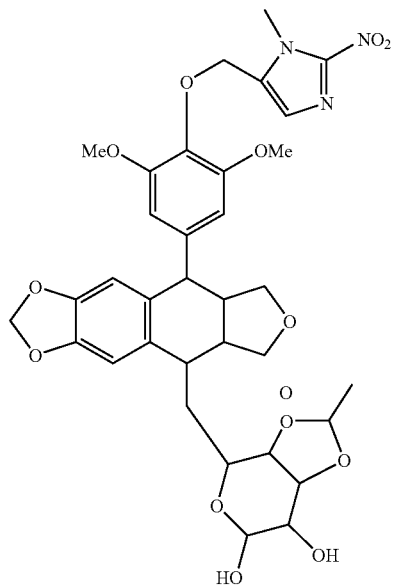

A nitroimidazole alkyl phenolic ether bearing a para or ortho benzyl alcohol can be used to form a ether connection with the phenolic group of etoposide analogous to the description above. A nitroimidazole alkyl phenolic ether bearing a para or ortho benzyl alcohol can be coupled to form an ether to the phenol of etoposide by first converting the benzyl alcohol to a bromide and then reacting under the standard alkylating conditions described above to effect the desired ether linkage with etoposide. Alternatively, the Mitsunobu conditions described above can be applied to form the desired ether. The following structural formula presents a nonlimiting example of such a structure.

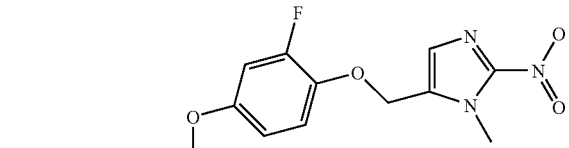

Example 3

Combretastatin A-4 and Analogs

The following is a prophetic example of an anti-neoplastic agent containing a phenolic group.

Combretastatin A-4 is a potent inhibitor of microtubules and possesses a single phenolic group that is thought to be essential for compound cytotoxic activity. There is a Combretastatin A-4 analog which differs only by the substitution of the phenolic group with an amino group and is incrementally more potent than Combretastatin A-4. Both of these compounds be modified and rendered inactive and then hypoxically released using the protected anti-neoplastic agents described in this patent. (For a review of the collection of Combretastatin analogs, see: Nam, N, Current Medicinal Chemistry, 2003, 10, 1697-1722). Many of these active analog can be protected as described below in an analogous fashion.

The structures of Combretastatin A-4 and its amino analog are shown below (A-4: X=O, $R_1$=H and amino analog: X=NH and $R_1$=H)

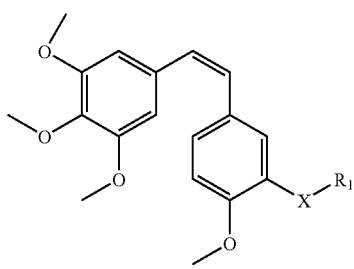

The following protecting groups may be used to protect the hydroxyl or amine groups in the Combretastatin A-4 and analogs, where the * indicates the point of attachment.

Prodrugs when X is O or NH

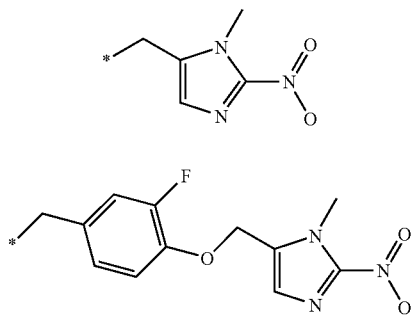

Prodrug when X is O or NH

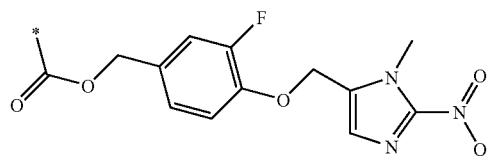

The connection of the third nitroimidazole construct to the parent Combretastatin A-4 is less optimum as the resulting carbonate may be unstable in vivo due to general esterases. The starting Combretastatin A-4 is commercially available. The amino analog can be synthesized as reported in Ohsumi, K, J. Med. Chem., 41 (16), 3022-3032, 1998. Synthesis of other analog can be found in the references described in Nam, N, Current Medicinal Chemistry, 2003, 10, 1697-1722.

Example 4

The Duocarmycin Family

The following is a prophetic example of an anti-neoplastic agent containing a phenolic group.

The hypoxically activated technology described in this patent can also be applied to the Duocarmycin family. A simple alkyl connection is described elsewhere in this patent and may be straightforwardly synthesized by methods described above for etoposide. The lower linker connection to the phenol of a duocarmycin may be straightforwardly synthesized as described above for etoposide. Many Duocarmycin analogs have been synthesized and one of skill in the art will understand that the free phenol in the position denoted as O—R may be protected using the protected anti-neoplastic agent technology described in this patent. (see references for analog options: Denny, W, A, Current Medicinal Chemistry, 2001, 533-44 and Searcey, M, Current Pharm. Discovery, 2002, 8, 1375-89.)

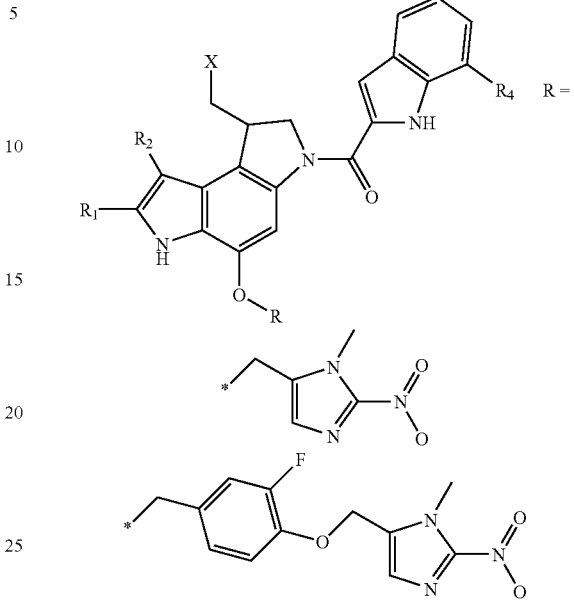

X may be a variety of groups, including but not limited to halo and sulfonolate, and particularly —Cl. Using the reagents described above for etoposide, the hypoxically activated prodrugs shown can be straightforwardly synthesized where the asterisk is the connection to the phenol or amine of the Duocarmycin.

Example 5

Barminomycin and Related Analogs

The following is a prophetic example of an anti-neoplastic agent containing a hemiaminal group.

Barminomycin is a natural product related to daunorubicin. It serves as a pre activated alkylating analog of daunorubicin by bearing an hemiaminal functionality which is in equilibrium upon elimination of water to form the active imine (Moufarij, M. A., et. al., Chemico-Biological Interactions, 138, 2001, 137-153). This added functionality results in cytotoxicity which is about 1000 fold increased relative to daunorubicin or doxorubicin

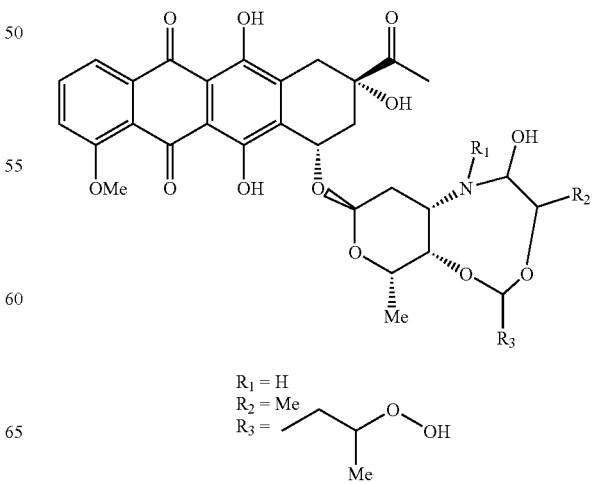

This toxin has been the subject of a patent application, JP4187096, which combines it in a vaguely described manner with an antibody which has dual recognition of barminomycin and a specific antigen Barminomycin may be regiospecifically modified on the nitrogen of the hemiaminal function with the nitrophenyl carbonate derived from 1-methyl-2-nitro-5-hydroxymethyl imidazole to produce the product shown above where the $R_1$ is shown below (left hand structure) with the asterisk being the connection to the nitrogen. Alternatively, the nitrogen of the hemiaminal of barminomycin can be reacted with the nitrophenyl carbonates of the nitroimidazole alkyl phenolic ether bearing a para or ortho benzyl alcohol as describe previously to produce the barminomycin analog where and example of R1 is shown below (right hand structure) with the asterisk being the connection to the nitrogen.

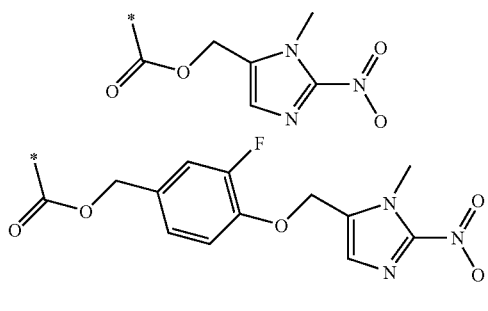

Example 6

Anthramycin and Related Analogs

The following is a prophetic example of an anti-neoplastic agent containing a hemiaminal group.

Anthramycin is an antitumor natural product for which many natural relatives have been identified such as tomaymcycin, sibiromycin, chicamycin A, neothramycin A and B and DC-81, among others. Many synthetic analogs have been synthesized based on these natural products and their methods of synthesis have been well reviewed in Kamal A., et. al., Current Medicinal Chemistry-Anti-Cancer Agents, 2002, 2, 215-254. These anticancer agents share a common important feature of existing in an aqueous solvent as a hemiaminal ($R_1$=H and $R_2$=H in the structure shown below for the anthramycin structure). It is this hemiaminal moiety which equilibrates with the imine form which is capable of crosslinking to the $N_2$ of a guanine in DNA upon drug binding in the minor groove of the DNA. This crosslinking event is responsible for the toxicity of these compounds and their anticancer activity.

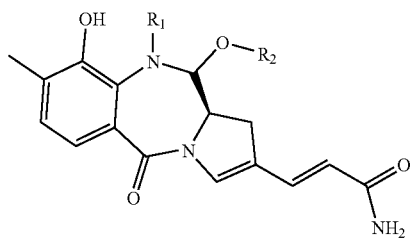

The N of the hemiaminal has been protected in prodrug form as a para nitrophenyl carbamate by Thurston in an attempt to make a prodrug version which is triggered by an *E Coli* nitroreductase enzyme. This enzyme was ultimately to be delivered in a tumor specific manner by conjugating it to a tumor specific antibody. This approach is known generally as ADEPT. A nitrobenzyl group is not capable of being reduced by mammalian enzymes given its low reduction potential. No mention is made in either the journal paper (Sagnou, M. J., Bioorganic and Medicinal Letters, 2000, 10, 2082) or U.S. Pat. No. 6,608,192 B1 and related filings as to the targeting of the hypoxic zones of tumors using a hypoxic specific release mechanism. We envision prodrugging the anthramycin series using the same reagents as described above for barminomycin. These reactions will produce anthramycin prodrugs where $R_2$ is H or an alkyl group such a methyl depending on the solvent pretreatment (water, methanol or another alcohol) of the anthramycin and where $R_1$ is shown below in analogous fashion to the barminomycin example with the asterisk being the attachment to the nitrogen of the hemiaminal.

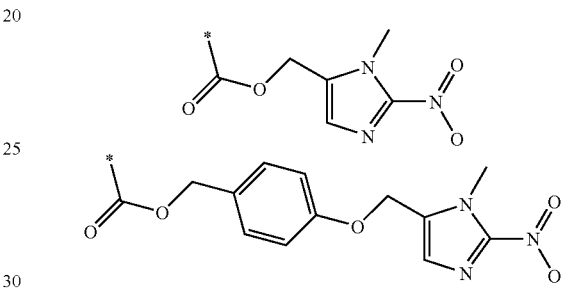

Example 7

Syntheses of the N-1-methyl-2-nitro-5-hydroxymethyl-imidazole

The following synthetic procedures were carried out to synthesize N-1-methyl-2-nitro-5-hydroxymethyl-imidazole.

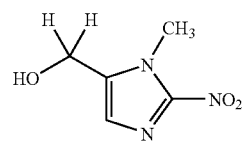

The Ester: N-1-Methyl-2-nitro-5-carboethoxyimidazole was synthesized according to the method described in the reference, Asato G; Berkelhammer, G., J. Med. Chem. 1972, 15, 1086. In the step involving a C-formylation, the prescribed base, KO$^t$BU was replaced with NaH. Product was characterized by H1 NMR The alcohol: The reduction of the ester functionality to a primary alcohol was performed following a hydrolysis of the ester to the acid. To a mixture of the acid (49 mmol) in THF (1500 mL) and triethylamine (71 mmol), chilled to −10 C was added dropwise isobutyl chloroformate (71 mmol) and stirred for 30 m. The temperature was raised to −5 C and stirred for 30 m. Upon disappearance of the starting material, NaBH$_4$ (263 mmol) was added slowly to the reaction mixture followed by addition of water (200 mL) over 30 m. After an additional 30 m the reaction mixture was filtered upon a pad of anhyd Na$_2$SO$_4$, volatiles removed in a rotary evaporator, and the residue purified on silica-gel column chromotograph using ethyl acetate to yield an essentially pure solid which was recrystalized from EtOAc-hexanes to yield the pure product. The product was characterized by LC-MS showing one significant peak at the appropriate molecule weight and by H1 NMR Synthesis of the
N-1-methyl-5-nitro-2-hydroxymethyl-imidazole

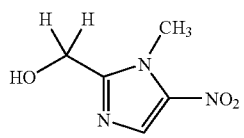

To a mixture of the ester (commercially available) (2 g, 10 mmol), THF (100 mL) was added dropwise LiBH4 (2 M in THF, 2 mL) at room temperature. After the addition of LiBH4 solution, the mixture was further stirred for 20 hr. Upon the disappearance of the starting material, saturated K2CO3 aqueous solution (1 mL) was added to the reaction mixture, after stirred the mixture for 1 hr, methanol (10 mL) was added to the reaction mixture. Filtration and flash column purification (eluent EtOAc:Hexane=1:1 (v/v)) gave pure alcohol as a white solid (1 g, 65%). The product was characterized by H1 NMR Example 8

Syntheses of the Bromides

The bromides can be easily prepared from the corresponding alcohols prepared according to Examples 7 and 1 by way of several methods known in literature. In one such method, a solution of N-1-methyl-2-nitro-5-hydroxymethyl-imidazole (1 eq, 1.8 Molar) and diisopropylethylamine (2 eq) in anhyd $CH_2Cl_2$ was added to a solution of $PPh_3$-$Br_2$ complex (commercial or in soln prepared in situ, 3.5 Molar) while maintaining 0 C and the reaction mixture stirred at 0 C until TLC analysis showed complete disappearance of starting material. Volatiles were removed in vacuo and the residue was purified by silica gel chromotograph to yield the desired bromide, reagent B. The product were characterized by H1 NMR.

The corresponding 5-nitroimidazole derivative was synthesized similarly from N-1-ethyl-5-nitro-2-hydroxymethyl-nitroimidazole Retrosynthetic General Schemes for Synthesis of Examples 9, 10, and 11 Daunorubicin Protected by a Hypoxic Activator Linked Via Various Delayed Release Groups These examples provide synthetic schemes for synthesis of three versions of compound H in the following scheme.

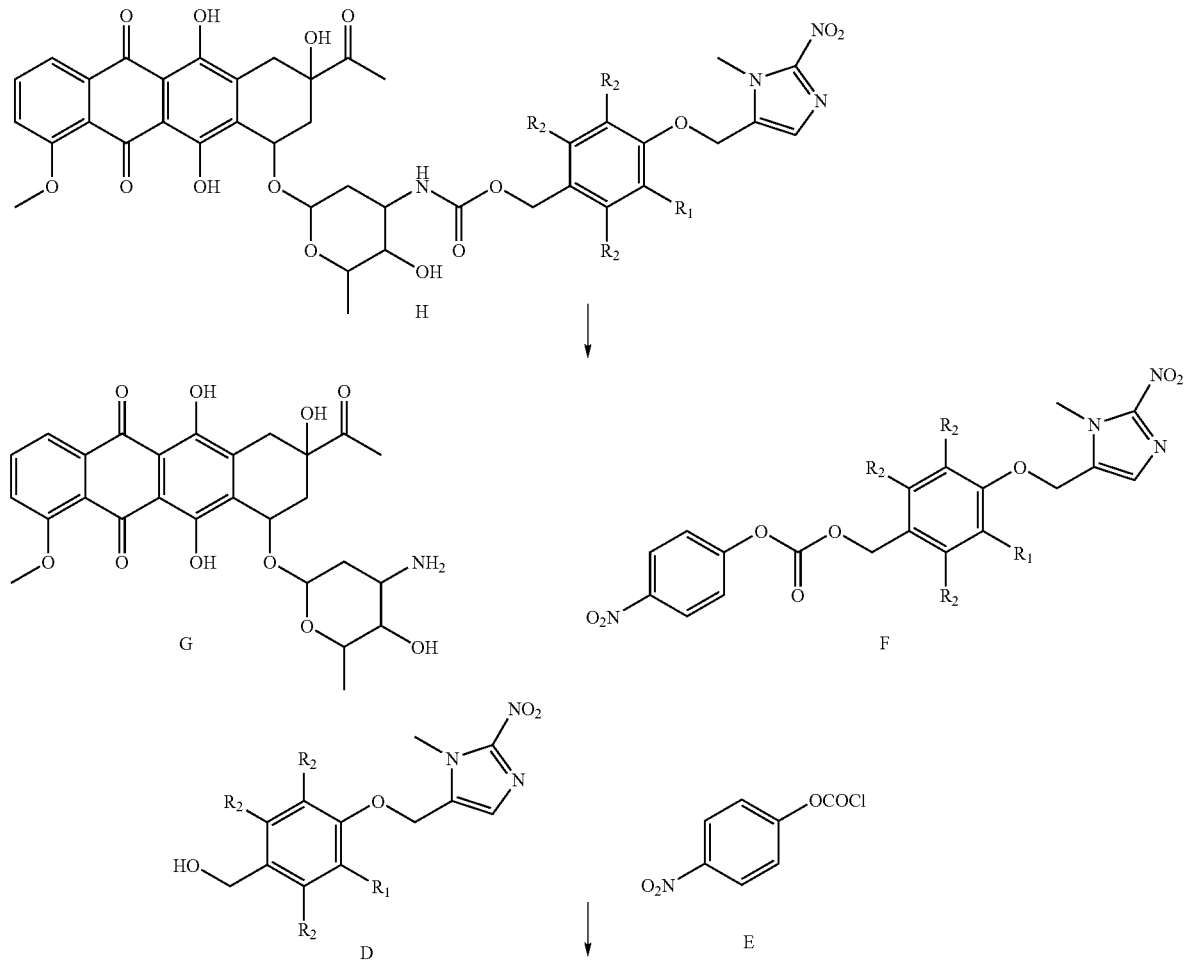

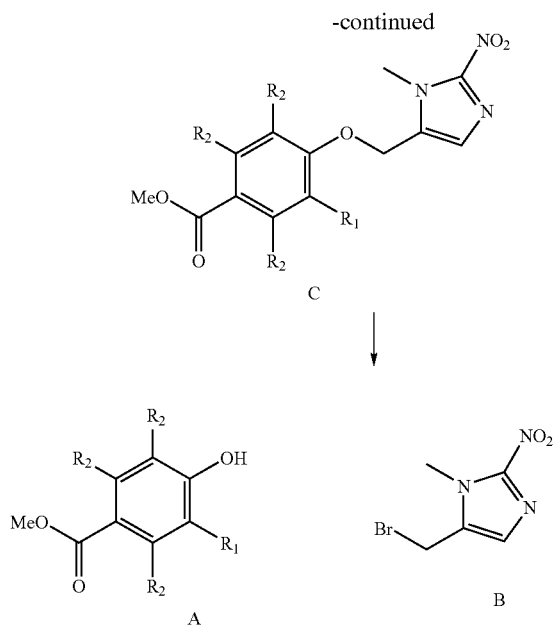

Example 9

Synthesis of Compound H with $R_1$ is Nitro, $R_2$ is Hydrogen in Scheme Above 1: Synthesis of Intermediate C, $R_1$ is Nitro, $R_2$ is Hydrogen Into a 100 mL round-bottomed flask was added a mixture of A, $R_1$ is nitro, $R_2$ is hydrogen, commercially available reagent, (100 mg), B (110 mg), $K_2CO_3$ (200 mg) and Acetone (anhydrous, 1 mL). The mixture was heated to reflux for 4 hr. After the reaction was finished, the solids were removed by filtration through the filter paper and pure product C (145 mg) was obtained after flash chromatograph (eluent EtOAc:Hexane (50:50(v/v))).

2: Reduction of C: Synthesis of Intermediate D, $R_1$ is Nitro, $R_2$ is Hydrogen:

Into a 100 mL round-bottomed flask was added a mixture of C (145 mg), LiBH4 (2M in THF, 1 mL) and anhydrous THF (5 mL). The solution was then stirred at room temperature for 24 hr. After the reaction finished, flash chromatography purification gave pure alcohol D (87 mg).

3: Synthesis Carbonate Intermediate F, $R_1$ is Nitro, $R_2$ is Hydrogen

Into a 10 mL round-bottomed flask was added a mixture of C, $R_1$ is nitro, $R_2$ is hydrogen (87 mg), THF (2 mL), pyridine (0.1 mL) and p-nitrophenol chloroformate (87 mg). The mixture was stirred at room temperature for 5 hr. Flash chromatography gave pure product (120 mg).

4: Synthesis of Compound H, $R_1$ is Nitro, $R_2$ is Hydrogen

Into a 25 mL round-bottomed flask was added a mixture F (20 mg), DMF (1 mL), daunorubicin HCl salt (25 mg) and DIEA (Diisopropylethylamine) (0.1 mL). The mixture was stirred at room temperature for 4 hr. After the reaction was finished, the mixture was poured into 10 mL dichloromethane and washed with brine (3×5 mL). Flash chromatography gave pure product (30 mg).

Clonogenic Assay

Example 10

Synthesis of Compound H with $R_1$ is Fluoro, $R_2$ is Fluoro

1: Synthesis of Intermediate C $R_1$ is Fluoro, $R_2$ is Fluoro

Into a 100 mL round-bottomed flask was added a mixture of A, $R_1$ is fluoro, $R_2$ is fluoro (120 mg), B (100 mg), $K_2CO_3$ (310 mg) and acetone (anhydrous, 2 mL). The mixture was heated to reflux for 4 hr. After the reaction was finished, the reaction mixture was diluted with EtOAc (20 mL) and the solids were removed by filtration through the filter paper and the organic solution was washed with 5% K2CO3 (3×10 mL). Evaporation gave C, $R_1$ is fluoro, $R_2$ is fluoro as white solid.

2: Reduction of C $R_1$ is Fluoro, $R_2$ is Fluoro: Synthesis of Intermediate D $R_1$ is Fluoro, $R_2$ is Fluoro:

Into a 100 mL round-bottomed flask was added a mixture of C—$R_1$ is fluoro, $R_2$ is fluoro (from the above reaction), LiBH4 (2M in THF, 0.2 mL) and anhydrous THF (10 mL). The solution was then stirred at room temperature for 24 hr. After the reaction finished, flash chromatography purification gave pure alcohol D, $R_1$ is fluoro, $R_2$ is fluoro.

3: Synthesis Carbonate Intermediate F, $R_1$ is Fluoro, $R_2$ is Fluoro:

Into a 10 mL round-bottomed flask was added a mixture of C, $R_1$ is fluoro, $R_2$ is fluoro (0.45 mmol), THF (2 mL), pyridine (0.1 mL) and p-nitrophenol chloroformate (0.54 mg). The mixture was stirred at room temperature for 5 hr. Flash chromatography gave pure product.

4: Synthesis of Compound H where $R_1$ is Fluoro and $R_2$ is Fluoro

Into a 25 mL round-bottomed flask was added a mixture F, $R_1$ is fluoro, $R_2$ is fluoro (8.8 mg), DMF (1 mL), daunorubicin HCl salt (10 mg) and DIEA (0.1 mL). The mixture was stirred at room temperature for 4 hr. After the reaction was finished, the mixture was poured into 10 mL dichloromethane and washed with brine (3×5 mL). Flash chromatography gave pure product (6.6 mg).

Example 11

Synthesis of Compound H, $R_1$ is Fluoro, $R_2$ is Hydrogen

1: Synthesis of Intermediate C, $R_1$ is Fluoro, $R_2$ is Hydrogen

Into a 100 mL round-bottomed was added 4-hydroxyl-2-fluorobenzoic acid (1 g), methanol (10 mL), and concentrated sulfuric acid (98%, 0.1 mL). The mixture was heated to reflux for 10 hr. After the reaction finished, the mixture was poured into 100 mL ice water and filtration gave pure product A, $R_1$ is fluoro, $R_2$ is hydrogen, (1 g) as white solid.

Into a 100 mL round-bottomed flask was added a mixture of A, $R_1$ is fluoro, $R_2$ is hydrogen (100 mg), B (100 mg), $K_2CO_3$ (200 mg) and Acetone (anhydrous, 1 mL). The mixture was heated to reflux for 4 hr. After the reaction was finished, the reaction mixture was poured into water (10 mL) and extracted with EtOAc (3×15 mL). The combined organic solution was then washed with 5% K2CO3 (aq., 3×10 mL) to remove the excess A and then dried over Na2SO4. Evaporation gave C, $R_1$ is fluoro, $R_2$ is hydrogen (130 mg) as a light yellow solid.

2: Reduction of C, $R_1$ is Fluoro, $R_2$ is Hydrogen: Synthesis of Intermediate D, $R_1$ is Fluoro, $R_2$ is Hydrogen:

Into a 100 mL round-bottomed flask was added a mixture of C, $R_1$ is fluoro, $R_2$ is hydrogen (100 mg), LiBH4 (2M in THF, 1 mL) and anhydrous THF (5 mL). The solution was then stirred at room temperature for 24 hr. After the reaction finished, flash chromatography purification gave pure alcohol D, $R_1$ is fluoro, $R_2$ is hydrogen (60 mg).

3: Synthesis Carbonate Intermediate F, $R_1$ is Fluoro, $R_2$ is Hydrogen:

Into a 10 mL round-bottomed flask was added a mixture of C, $R_1$ is fluoro, $R_2$ is hydrogen (10 mg), THF (2 mL), pyridine (0.1 mL) and p-nitrophenol chloroformate (10 mg). The mixture was stirred at room temperature for 5 hr. Flash chromatography gave pure product (14 mg).

4: Synthesis of Compound H where $R_1$ is Fluoro and $R_2$ is Hydrogen:

Into a 25 mL round-bottomed flask was added a mixture F, $R_1$ is fluoro, $R_2$ is hydrogen (8.5 mg), DMF (1 mL), daunorubicin HCl salt (10.7 mg) and DIEA (0.1 mL). The mixture was stirred at room temperature for 2 hr. After the reaction was finished, the mixture was poured into 10 mL dichloromethane and washed with brine (3×5 mL). Flash chromatography gave pure product.

The products synthesized in Examples 9, 10, and 11 were characterized by LC-MS with a major peak of the appropriate molecular weight Example 12

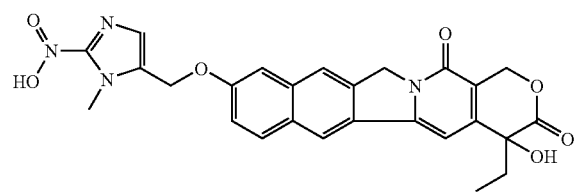

Alkylation of 10-hydroxycamptothecin with N-1-methyl-2-nitro-5-(bromomethyl)-imidazole The alkylation of the phenolic hydroxyl group of 10-Hydroxycamptothecin was performed under standard conditions used myriad times in the literature to alkylate. The phenolic moiety of 10-hydroxycamptothecin: A mixture of 10-Hydroxycamptothecin (2 eq, 0.1 milliMolar) in anhyd, degassed DMF, anhyd $K_2CO_3$ (3 eq), and the relevant nitroimidazole bromide (1 eq) was stirred at rt for ca 16 h and volatiles were removed in a rotary evaporator. The residue was purified by silica gel chromotograph to yield the desired ethers provided in this Example 12 (5-nitro). Compound were characterized by LC-MS showing major peak of appropriate molecular weight Example 13

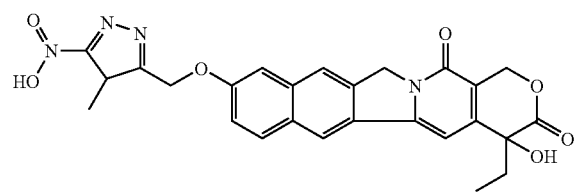

Alkylation of 10-hydroxycamptothecin with N-1-methyl-5-nitro-2-(bromomethyl)-imidazole The alkylation, purification and characterization was performed in analogous fashion to the methods described in Example 12 above Example 14

Biological Testing

The following biological assays were used to characterize various of the protected anti-neoplastic agents.

A) Clonogenic Toxicity Assay

Introduction

To determine if a drug is an effective anticancer agent we use the clonogenic assay as a stringent test for cell survival. The clonogenic assay measures the reproductive ability of a surviving cell by specifically determining if a cell can grow to form a colony of greater than 50 cells. Briefly, cells are treated with a drug for an acute exposure and then the drug is removed. Cells are trypinized to form single cell suspensions and known numbers of cells are plated and incubated until colonies form. Colonies are counted and the cell survival is calculated based on number of colonies formed in the treated groups compared to number of colonies formed in the untreated controls. In order to determine if a drug is selectively toxic under anoxic conditions cells are exposed to the drug either with air (normoxic) or completely without oxygen (anoxia). The terms aerobic and normoxic are used interchangeably.

Experimental Methods

Exponentially growing human H460 cells (obtained from ATCC) were seeded into 60 mm notched glass plates between 2.5 and $5 \times 10^5$ cells per plate and grown in RPMI medium supplemented with 10% fetal bovine serum for 2 days prior to initiating treatment. On the day of the experiment drug stocks of known concentrations were prepared in complete medium and 2 ml added to each plate. Glass plates were sealed into airtight aluminum vessels equipped with a valve to control gas flow. To achieve complete equilibration between the gas phase and the liquid phase a series of gas exchanges were performed on each vessel while shaking. Vessels were evacuated and gassed with either a certified anoxic gas mixture (95% nitrogen and 5% carbon dioxide) or with aerobic gas mixture (95% air and 5% carbon dioxide). Specifically, each vessel was evacuated to minus 26 inches of mercury and held for 15 seconds before gassing at 20 psi and again holding for 15 seconds. After a series of five evacuations and gassings the vessels were held an additional 5 minutes before a final evacuation and refilling of each vessel with the desired gas mixture at 0.5 psi above atmospheric pressure. Cells were incubated for 2 hours at 37° C. At the end of treatment, plates were removed from each vessel and the drug promptly removed from the cells. Plates were washed with phosphate buffered saline and a solution of trypsin-EDTA and then trypsinized for 5 minutes at 37° C. Detached cells were neutralized with medium plus serum and spun for 5 min at 100×g. Cells were resuspended at approximately $1 \times 10^6$ cells/ml and diluted 10 fold to yield stock concentrations for plating. The exact concentration of each stock was determined by counting with a Coulter Z2 particle counter. Known numbers of cells were plated and placed undisturbed in an incubator for between 7 and 10 days. Colonies were fixed and stained with a solution of 95% ethanol with 0.25% crystal violet stain. Colonies of greater than 50 cells were counted and the surviving fraction determined.

Result

The daunorubicin control showed no significant toxicity difference in the above clonogenic assay (2 hr compound exposure) between normoxic (air) and anoxic conditions. The IC 90 (90% inhibition of colony formation) was 0.5 micromolar with data ranges of 0.2 micromolar to 1 micromolar over multiple experiments The compound of Example 9 showed under the same hypoxic conditions an IC 90 of 4 micromolar with data ranges of 2 micromolar to 5 micromolar over multiple experiments. The normoxic data was very dramatic with no toxicity being seen at the highest concentration of 20 micromolar, the limit of solubility in cell media for this assay. The compound of Example 9 showed a marked lack of toxicity under normal air conditions, implying the Example 9 compound is a very selective compound.

The compound of Example 10 showed under the same hypoxic conditions an IC 90 of 1 micromolar with data ranges of 0.5 micromolar to 2 micromolar over multiple experiments. The normoxic data was very dramatic with no toxicity being seen at the highest concentration of 10 micromolar, the limit of solubility in cell media for this assay. The compound of Example 10 showed a marked lack of toxicity under normal air conditions, implying the Example 10 compound is a very selective compound.

The compound of Example 11 showed under the same hypoxic conditions an IC 90 of 1 micromolar in one experiment. Under normoxic conditions the IC50 was approximately 5 micromolar in one experiment. The compound of Example 11 thus demonstrates good selectivity between anoxic and normoxic conditions.

Intracellular Activation of Hypoxia Activated Prodrugs

Biological Assay

Introduction

To determine if a prodrug compound can be reduced by cellular reductases and therefore lead to the release of the active drug, we have assayed for drug metabolism in the medium of cells exposed to the prodrug under aerobic or anoxic conditions.

Experimental Methods 10 hydroxy camptothecin and the compound described in Example 12 (2 nitroimidazole 10 hydroxy camptothecin) stocks were diluted to 30 uM in RPMI medium without phenol red and supplemented with 10 mM HEPES and 10% fetal bovine serum. Exponentially growing H460 cells were harvested and $1 \times 10^7$ cells were resuspended directly in 1 ml medium with drug. Drug only stocks and cells with drug were placed in 60 mm notched glass plates and exposed to anoxia or aerobic gases as previously described. All groups were incubated for 3 hours at 37° C. To end treatment and extract drug from medium, all groups were transferred to microfuge tubes and spun 3 min at 15000×g to pellet cells. The supernatant was removed and acidified with glacial acetic acid (10% final concentration). Drug was extracted from RPMI medium by the addition of an equal volume of ethyl acetate, mixing, centrifuging, and removing the upper organic phase. All samples were evaporated to dryness in a rotary speed vacuum system. Dried samples were stored at −20° C.

| # | Group | Medium | Exposure |
|---|---|---|---|
| 1 | No drug | RPMI medium + 10% FBS | Anoxic |
| 2 | ~30 uM 10-OH Camptothecin | RPMI medium + 10% FBS | Anoxic |
| 3 | ~30 uM compound of Example 12 | RPMI medium + 10% FBS | Anoxic |
| 4 | ~30 uM compound of Example 12 with cells | RPMI medium + 10% FBS | Anoxic |
| 5 | No drug | RPMI medium + 10% FBS | Aerobic |
| 6 | ~30 uM10-OH Camptothecin | RPMI medium + 10% FBS | Aerobic |
| 7 | ~30 uM compound of Example 12 | RPMI medium + 10% FBS | Aerobic |
| 8 | ~30 uM compound of Example 12 with cells | RPMI medium + 10% FBS | Aerobic |

Interpretation

As can be seen by the analytical report below the compound of Example 12 is triggered to release the parent 10 hydroxy-camptothecin only under anoxic conditions and in the presents of H460 cells. The degree of release (trial 4) is significant as over half of the compound of Example 12 was cleanly converted. The LC-MS analysis showed no other significant peaks in the LC trace at the 10 hydroxycamptothecin selective wavelength of 370 nm other than the ones quantitated below. All other control reactions showed no detectable release of 10 hydroxycamptothecin including the aerobic incubation with H460 cells with the compound of Example 12. These results demonstrate a highly selective (anoxic versus hypoxic) release mechanism for the compound of Example 12.

Analytical Report for Example 12 Compound Cellular Assay

| Sample ID | 10-Hydroxy Campothecin UV peak area (370 nm) | Example 12 compound UV peak area (370 nm) | Ratio 10-Hydroxy Campothecin/ Example 12 compound |
|---|---|---|---|
| No drug, anoxic | 0 | 0 | — |
| 10-OH Camptothecin anoxic (~30 µM) | 1280 | 0 | — |
| Example 12 compound anoxic (~30 µM) | ~0 | 938.3 | ~0% |
| Example 12 compound with cells anoxic (~30 µM) | 733.3 | 829.8 | 88% |
| No drug Aerobic | 0 | 0 | — |
| 10-OH Camptothecin Aerobic (~30 µM) | 820.4 | 0 | — |
| Example 12 compound Aerobic (~30 µM) | ~0 | 272.0 | ~0% |
| Example 12 compound with cells Aerobic (~30 µM) | ~0 | 634.4 | ~0% |

Example 15

Prodrugs of Doxorubicin and Related Compounds

The following is a prophetic example of protected anti-neoplastic agents as described in this patent:

This Example describes illustrative protected anti-neoplastic agents that release highly cytotoxic derivatives of doxorubicin. Those of skill in the art will appreciate that doxorubicin, epirubicin, and daunomycin, and the numerous analogs and derivatives of those compounds that have been and continue to be synthesized represent a class of compounds that can be readily converted into protected anti-neoplastic agents based on the teachings herein. This example illustrates such protected anti-neoplastic agents that release highly cytotoxic compounds under hypoxic conditions. Highly cytotoxic daunomycin derivatives are described in the reference Bakina and Farquhar, 1999, Anti-cancer Drug Design 14: 507, incorporated herein by reference. Part A of this Example illustrates a protected anti-neoplastic agents that releases such a highly cytotoxic derivative, referred to herein as a doxorubicin derivative, and that comprises one hypoxia-activated moiety. Part B of this Example illustrates such a prodrug that comprises more than one such moiety. Part C of this Example illustrates such a prodrug that releases a novel dicationic derivative.

Part A. Hypoxia-activated Doxorubicin Derivative Prodrug. The single free amino group of doxorubicin, daunomycin, epirubicin, and derivatives thereof having only this single free amino group can be readily modified with a hypoxic activator as described herein to yield protected anti-neoplastic agents having the following structure (DOX is doxorubicin or one of the related compounds previously mentioned other than the free amino group):

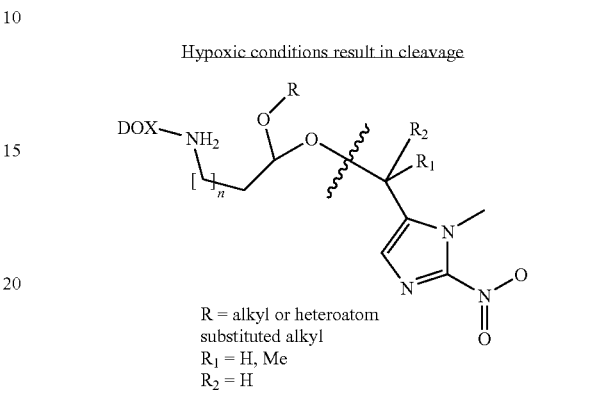

R = alkyl or heteroatom substituted alkyl
$R_1$ = H, Me
$R_2$ = H

Under hypoxic conditions, the hypoxia-activated moiety is removed, releasing the following highly cytotoxic compound shown as iminium DOX (or Super Dox), below.

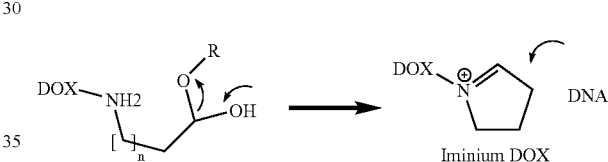

A scheme for another illustrative prodrug of a "super DOX" analog of the protected anti-neoplastic agents described herein is shown below.

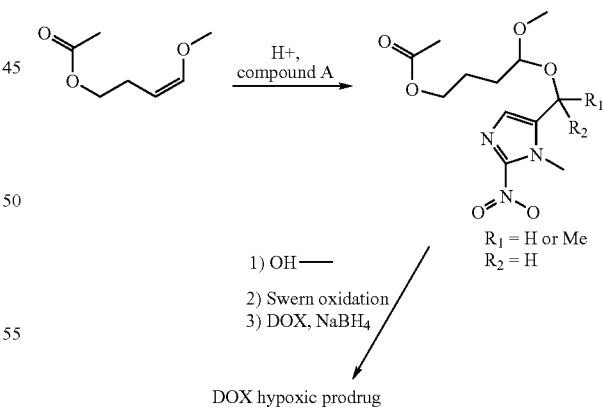

$R_1$ = H or Me
$R_2$ = H

1) OH—
2) Swern oxidation
3) DOX, NaBH$_4$

DOX hypoxic prodrug

Part B. Hypoxia-activated Doxorubicin Derivative Prodrug that Requires Removal of Multiple Hypoxia-activated Moieties. The methodology described in part A of this example can be used to generate protected anti-neoplastic agents that have two or more hypoxia-activated moieties. One illustrative protected anti-neoplastic agent having three such moieties is shown below (X is defined in part C).

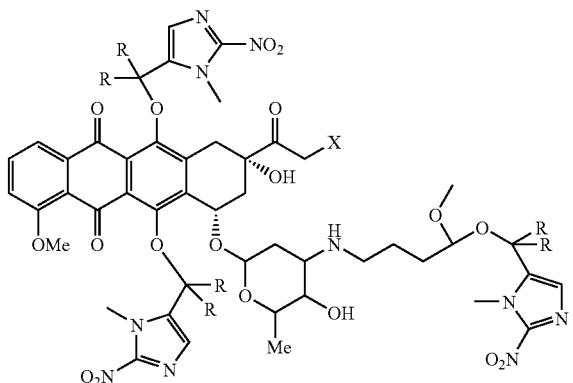

R = H, Me (with the proviso that at least on R is H)

Part C. Hypoxia-activated Doxorubicin Diamine Derivative Prodrug. Doxorubicin can be derivatized in accordance with a synthetic method as described herein with an aminoethyl moiety to generate a dicationic doxorubicin derivative that is highly cytotoxic and binds more tightly to DNA than doxorubicin. One example of a protected anti-neoplastic agent has the following structure (in the structure below, X represents any of the diverse moieties present in doxorubicin, daunomycin, epirubicin, and their naturally occurring and synthetic derivatives):

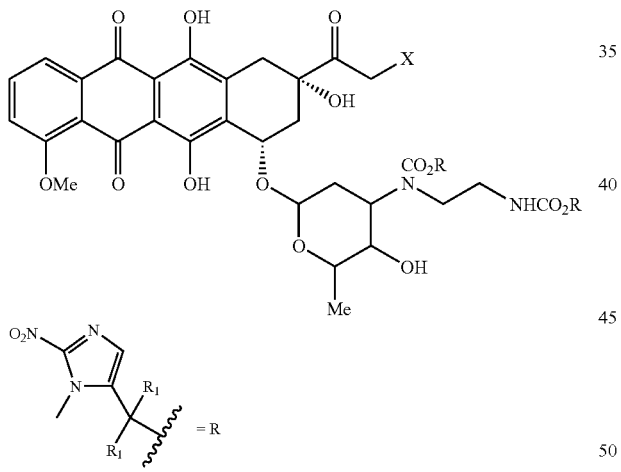

$R_1$ = H, Me, with proviso that at least one $R_1$ is H

Upon hypoxia-activated release, the compound is protonated to convert the carboxamates to the corresponding amines. The prodrug is formed by reacting doxorubicin or a doxorubicin derivative with $HC(O)CH_2NHCO_2R$, where R is defined as above, first in the presence of $NaB(OAc)_3H$ and then in the presence of $R'CO_2Cl$, where R' is $C_{1-6}$ lower alkyl, and base.

Example 16

Prodrugs of Etoposide

The following is a prophetic example of protected anti-neoplastic agents as described in this patent.

Etoposide is a potent non-intercalating DNA topoisomerase II inhibitor. In accordance with the synthetic methods described herein, one can readily form protected anti-neoplastic agents that release etoposide under hypoxic conditions as follows. The hypoxia-activated moiety is attached to the etoposide at the phenolic hydroxy positions via an ether linker.

These linkers can be provided by other useful intermediate reagents as described herein, shown below. These reagents can be readily prepared from the corresponding alcohol

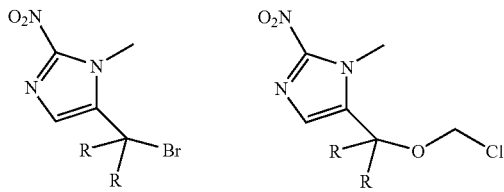

R = H, Me (with proviso that at least one R is H)

Two illustrative prodrugs, labeled A and B below, and a scheme for forming them from etoposide are shown below.

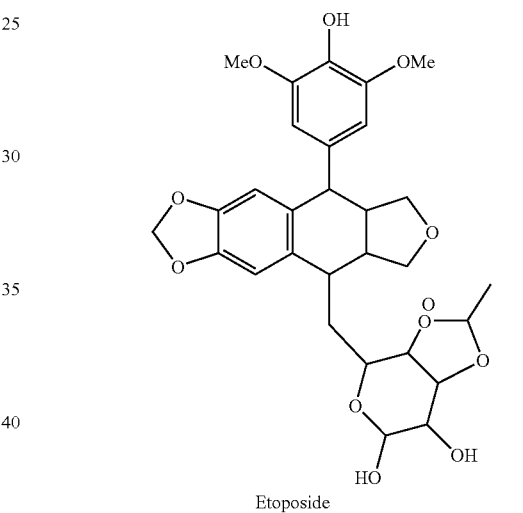

Etoposide

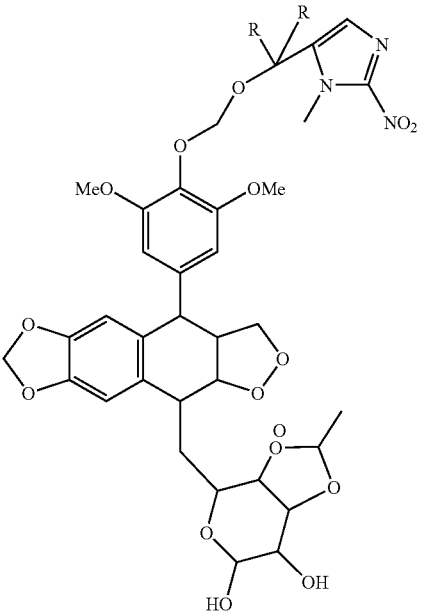

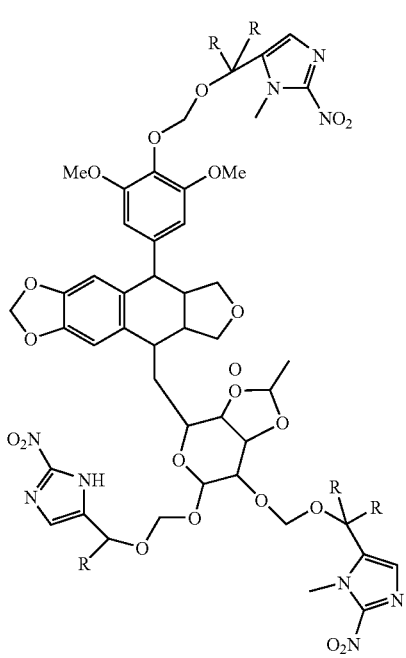

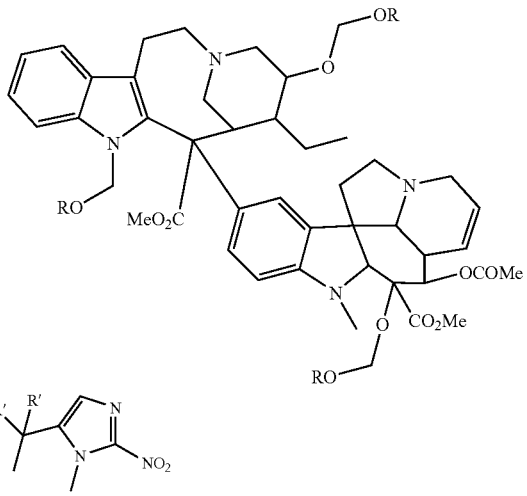

R' = H, Me (with the proviso that at least one R' is H

Vincristine-releasing protected anti-neoplastic agents are prepared in an analogous manner, starting with vincristine.

Example 18

Prodrugs of Topotecan

The following is a prophetic example of protected anti-neoplastic agents as described in this patent.

Protected anti-neoplastic agents that release topotecan can be prepared from topotecan as shown in the scheme below using synthetic methodology substantially similar to that described in Example 16.

Example 17

Prodrugs of Vinca Alkaloids

The following is a prophetic example of protected anti-neoplastic agents as described in this patent.

Protected anti-neoplastic agents that release vinblastine (or another vinca alkaloid) can be prepared from vinblastine (or another vinca alkaloid) as shown in the scheme below (the indole NH can be attached to the hypoxia-activated moiety selectively over attachment at the hydroxyls) using synthetic methodology substantially similar to that described in Example 16

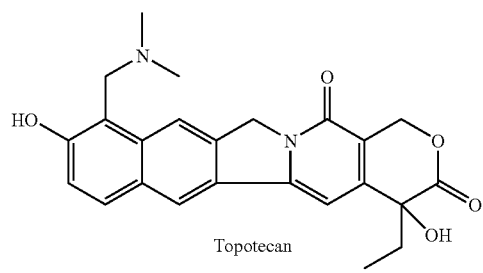

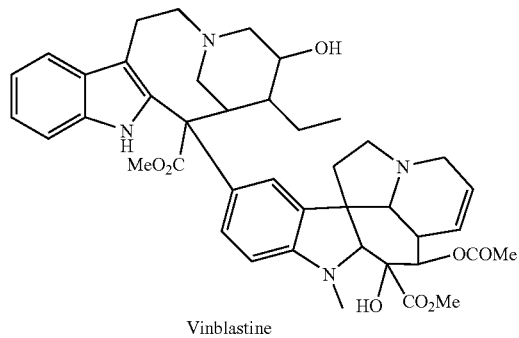

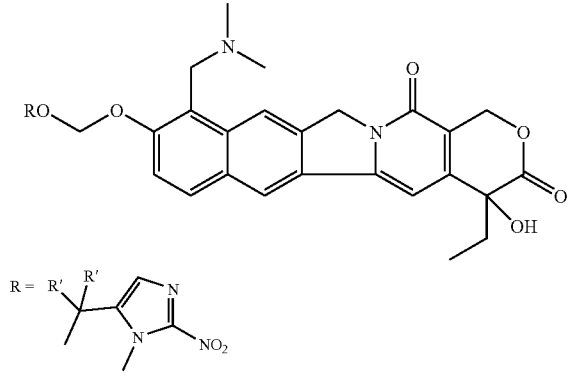

R = H or Me (with the provisio that at least on R' is H)

Example 19

Prodrugs of Taxanes

The following is a prophetic example of protected anti-neoplastic agents as described in this patent.

Protected anti-neoplastic agents that release paclitaxel, docetaxel, or another taxane can be prepared from paclitaxel (or docetaxel or another taxane) using synthetic methodology substantially similar to that described in Example 16 to prepare compounds similar in structure to the structure shown below.

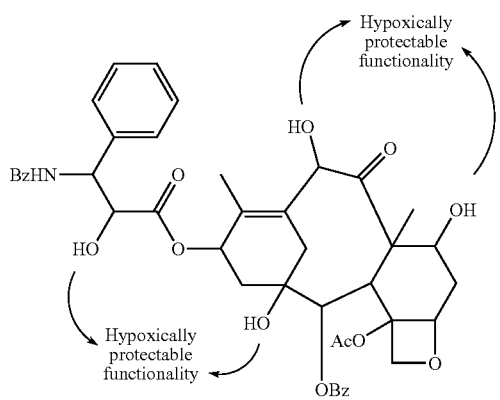

As indicated in the structure above, such protected anti-neoplastic agents can have one, two, three, or four hypoxia-activated moieties. In some versions, these hypoxia-activated moieties are selected from those shown below.

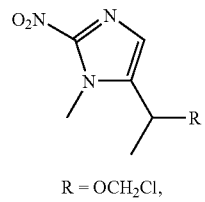

R = OCH$_2$Cl,

Example 21

Prodrugs of 5-FU

The following is a prophetic example of protected anti-neoplastic agents as described in this patent.

Protected anti-neoplastic agents that release 5-fluorouracil (5-FU) can be prepared from 5-FU using synthetic methodology substantially similar to that described in Example 16. One such prodrug has the structure shown below.

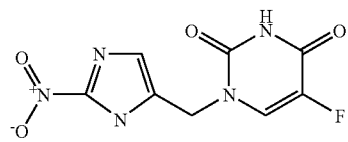

Another protected anti-neoplastic agent has two hypoxia-activated moieties attached, one as shown in the structure above, and the other to the other ring nitrogen.

Example 21

Prodrugs of Alkylating Agents

The following is a prophetic example of protected anti-neoplastic agents as described in this patent.

Protected anti-neoplastic agents that release an alkylating agent can be prepared from as shown in the scheme below using synthetic methodology substantially similar to that described in Example 16. A protected anti-neoplastic agents of cyclophosphamide is used to illustrate this aspect of the compounds and methods described herein. This protected anti-neoplastic agents can be synthesized in accordance with the methods described herein using the following illustrative synthetic method.

Synthesis

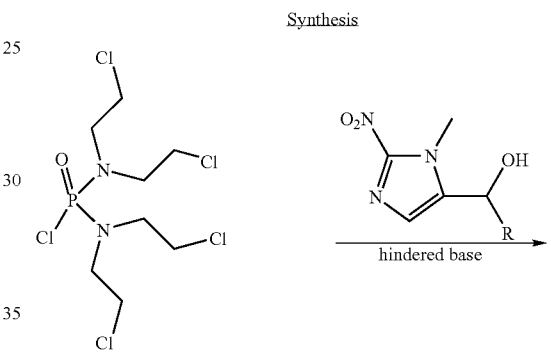

Example 22

Prodrugs of Hydroxyurea

The following is a prophetic example of protected anti-neoplastic agents as described in this patent.

Protected anti-neoplastic agents that release hydroxyurea (HU) can be prepared from hydroxyurea as shown in the scheme below using synthetic methodology substantially similar to that described in Example 16. HU (sold as Hydrea by Bristol-Myers Squibb) is an anti-leukemic drug with a mechanism of action ascribed to the inhibition of the DNA synthesizing enzyme ribonucleoside reductase. HU has also been shown to be effective against brain tumors (meningioma).

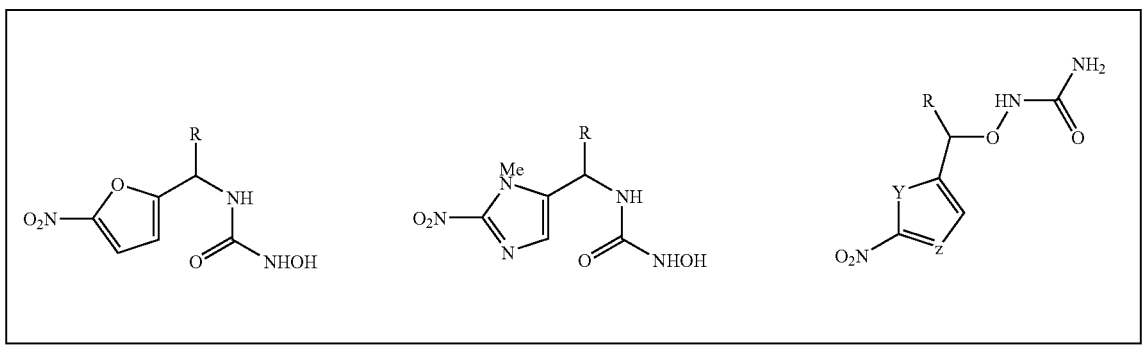

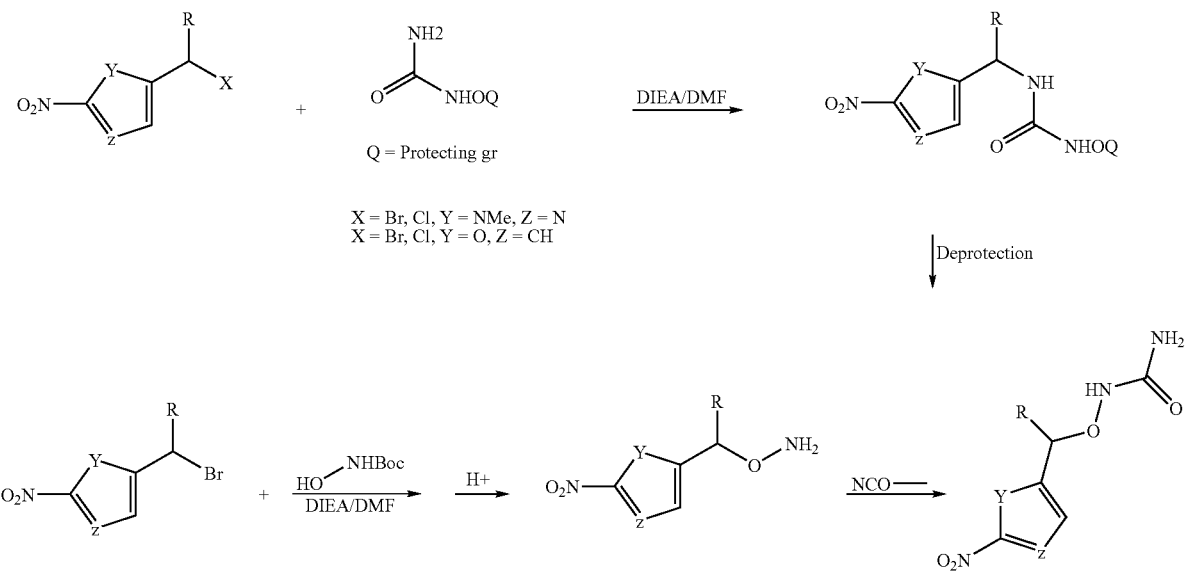

Example 23

Nitroimidazole-20-Camptothecin Prodrugs

The following is a prophetic example of protected anti-neoplastic agents as described in this patent.

A representative example of a method for preparing an illustrative camptothecin protected anti-neoplastic agents is shown below.

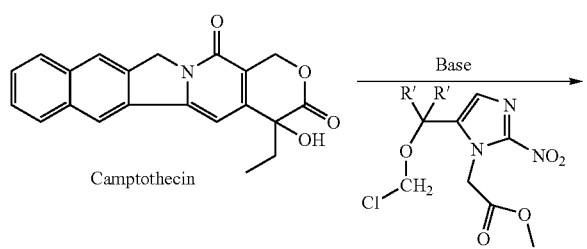

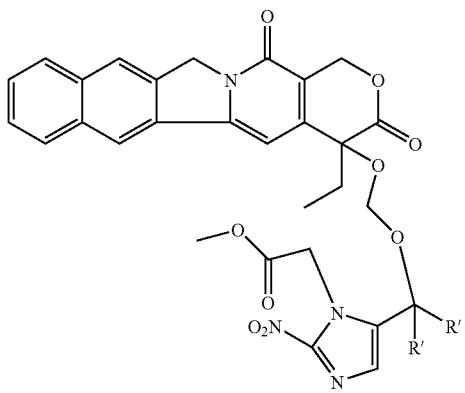

R' = H or Me,
(with proviso that one R' is H)

The N methylacetate moiety on the imidazole can be synthesized by demethylating the hydroxymethyl imidazole derivative with hydroiodic acid and realkylating it with methyl bromoacetate. Upon prodrug formation, the methoxy ester is removed, optionally with sodium hydroxide followed by acid treatment to restore the active lactone of camptothecin.

Alternatively, the camptothecin lactone can be hydrolyzed to the open form and the alcohol moiety derivatized with a chloromethyl nitroimidazole or chloromethoxymethyl nitroimidazole derivative. This nitroimidazole derivative need not bear a carboxylic acid group off of the 1 position on the imidazole but can be rendered stable to two electron reduction by DT diaphorase by having a sterically hindered alkyl group, as discussed above. This reaction can be carried out by the bis alkylation of the free carboxylic acid and the alcohol followed by basic hydrolysis of the ester, leaving a free acid for solubility and the nitroimidazole prodrug moiety masking the essential alcohol functionality. Prodrug release under hypoxic conditions in vivo will result in the release of the alcohol. Subsequent cyclization with the carboxylic acid under the acidic conditions of the tumor will generate an active camptothecin. Such analogs of camptothecin can be prepared analogously, using any of the numerous camptothecin analogs known in the art as the drug to protected to yield a protected anti-neoplastic agent.

Example 24

Nitroimidazole Prodrugs of Duocarmycin

The following is a prophetic example of protected anti-neoplastic agents as described in this patent.

Many duocarmycin analogs and their prodrugs are known (see U.S. Pat. No. 5,985,909, PCT patent publication No. US02/17210, and U.S. patent application publication No. 2003/0050331 A1). None of these analogs or prodrugs employ a nitroimidazole triggered to release the duocarmycin using a stable ether connection to the phenolic group of the duocarmycin. A representative example of a nitroimidazole duocarmycin protected anti-neoplastic agent is shown below, in which the phenolic oxygen is protected as an ether with the nitroimidazole as shown. The synthesis starts, in one version, with the free duocarmycin phenol and the nitroimidazole derivative bearing a bromomethyl or chloromethyl group as the precursor to the ether connection. $R_1$ can be H, methyl or lower alkyl, $R_2$ can be COOR, CN or $NO_2$, X can be Cl, Br, I or sulfonate, $R_3$ and $R_4$ can be as described in PCT/US02/17210. The $R_5$ group on the nitroimidazole can be methyl or a hindered alkyl as described above.

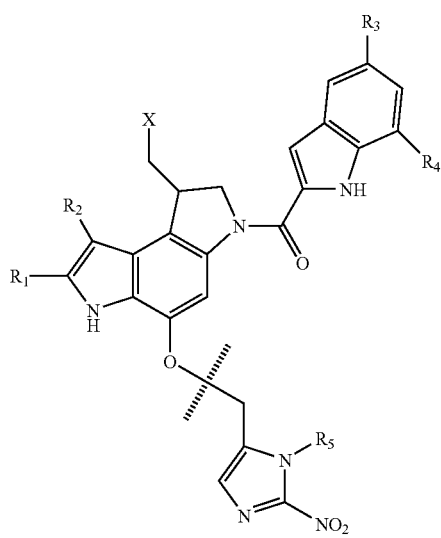

All references, patents and patent applications cited herein are incorporated herein by reference in their entirety to the same extent as though each reference, patent and patent application was incorporated by reference in their entirety individually.

What is claimed is:

1. A protected anti-neoplastic agent, in which the anti-neoplastic agent is an alkylating agent, and includes one or more protectable hydroxyl groups or amine groups, and wherein one or more of the protectable hydroxyl groups or amine groups is substituted with a group selected from Hyp-L- or Hyp-, wherein Hyp is a hypoxic activator having the formula

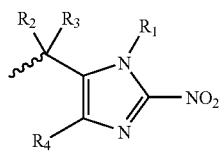

wherein $R_1$ is substituted or unsubstituted $C_1$-$C_6$ alkyl or substituted or unsubstituted $C_1$-$C_6$ alkoxy;
$R_2$ is hydrogen;
$R_3$ is —H or $C_1$-$C_6$ alkyl; and
$R_4$ is —H, substituted or unsubstituted $C_1$-$C_6$ alkyl, or substituted or unsubstituted $C_1$-$C_6$ alkoxy;
wherein the $R_1$ and $R_4$ substituted alkyl and substituted alkoxy are independently substituted with one or more heteroatom-containing groups selected from ether (—$OR^{20}$), amino (—$NH_2$), mono-substituted amino (—$NR^{20}H$), di-substituted amino (—$NR^{21}R^{22}$), cyclic $C_{1-5}$ alkylamino, imidazolyl, $C_{1-6}$ alkylpiperazinyl, morpholino, thiol (—SH), thioether —($SR^{20}$), tetrazole, carboxylic acid (—COOH), ester (—$COOR^{20}$), amide (—$CONH_2$), mono-substituted amide (—$CONHR^{20}$), disubstituted amide (—$CONR^{21}R^{22}$), N-connected amide (—$NH_2$—C(=O)—$R^{20}$), mono-substituted N-connected amide (—$NHR^{21}$—C(=O)—$R^{20}$), disubstituted N-connected amide (—$NR^{21}R^{22}$—S(=O)$_2$—$R^{20}$), N-connected sulfonamide (—$NH_2$—S(=O)$_2$—$R^{20}$), mono-substituted N-connected sulfonamide (—$NHR^{21}$—S(=O)$_2$—$R^{20}$), disubstituted N-connected sulfonamide (—$NR^{21}R^{22}$—S(=O)$_2$—$R^{20}$), sulphoxy (—S(=O)$_2$OH), sulphonate (S(=O)$_2$$OR^{20}$), sulphonyl (S(=O)$_2$$R^{20}$), sulphixy (S(=O)OH), sulphinate (S(=O)$OR^{20}$), sulphinyl (S(=O)$R^{20}$), phosphonooxy (OP(=O)(OH)$_2$), phosphate (OP(=O)($OR^{20}$)$_2$), and sulfonamide (—S(=O)$_2$$NH_2$, —S(=O)$_2$$NHR^{21}$, or —S(=O)$_2$$NR^{21}R^{22}$), where $R^{20}$, $R^{21}$, and $R^{22}$ are independently selected from a $C_1$-$C_6$ alkyl group; and
L is a linking group of the formula

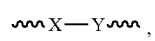

where X is selected from

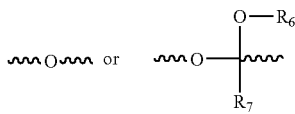

wherein $R_6$ is unsubstituted alkyl or alkyl substituted with one or more heteroatom containing groups;

$R_7$ is hydrogen, unsubstituted alkyl or alkyl substituted with one or more heteroatom containing groups; and Y is a spacer group selected from a substituted or unsubstituted —$(CH_2)_n$— chain with n=1-4; a substituted or unsubstituted —$(CH_2)_n$— chain with n=1-4 in which one of the carbon backbone chain atoms is substituted by a heteroatom containing group; or a delayed release group comprising an aromatic group.

2. The protected anti-neoplastic agent of claim 1, wherein $R_6$ is unsubstituted C1-C3 alkyl or C1-C3 alkyl substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano;

R7 is hydrogen, unsubstituted C1-C3 alkyl, or C1-C3 alkyl substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; and the spacer group Y is an unsubstituted —$(CH_2)_n$— chain with n=1-4, or a —$(CH_2)_n$— chain with n=1-4 substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano; or the spacer group Y is the delayed release group and has the formula

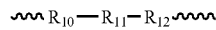

where R10 is a bond; R11 is an unsubstituted or substituted aryl or substituted or unsubstituted heteroaryl group; and R12 has the formula —$(CR^{40}R^{41})$—$R^{42}$— or —$(CR^{40}R^{41})$—$CR^{43}$=$CR^{44}$—$R^{42}$—, where $R^{42}$ is a bond or —OC(=O)—, and $R^{40}$, $R^{41}$, $R^{42}$, and $R^{43}$ are independently selected from —H, unsubstituted $C_1$-$C_{10}$ alkyl, and $C_1$-$C_{10}$ alkyl substituted with one or more heteroatom containing groups selected from hydroxyl, ether, thiol, thioether, sulfinic ester, sulfoxide, sulfone, sulfonic acid, sulfonic acid ester, sulfenamide, sulfonamide, carboxylic acid, carboxylic acid salt, ester, amide, aldehydo, keto, amino, halo, and cyano.

3. A method for treating cancer comprising administering to a subject a therapeutically effective amount of a protected anti-neoplastic agent according to claim 1, wherein the cancer is selected from the group consisting of colon cancer, prostate cancer, lung cancer, non-small cell lung cancer, liver cancer, skin cancer, sarcomas, pancreatic cancer, breast cancer, head and neck cancer, and myeloma.

4. A protected anti-neoplastic agent of formula Hyp-L-N or Hyp-N, wherein Hyp is a hypoxic activator moiety of formula

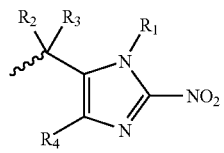

wherein $R_1$ is unsubstituted $C_1$-$C_6$ alkyl, $C_1$-$C_6$ alkyl substituted with one or more heteroatom-containing groups, unsubstituted $C_1$-$C_6$ alkoxy, or $C_1$-$C_6$ alkoxy substituted with one or more heteroatom-containing groups;

$R_2$ is hydrogen;

$R_3$ is hydrogen or $C_1$-$C_6$ alkyl; and $R_4$ is hydrogen, unsubstituted $C_1$-$C_6$ alkyl, $C_1$-$C_6$ alkyl substituted with one or more heteroatom-containing groups, unsubstituted $C_1$-$C_6$ alkoxy, or $C_1$-$C_6$ alkoxy substituted with one or more heteroatom-containing groups;

L is a linking group of the formula

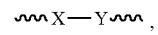

wherein X is selected from

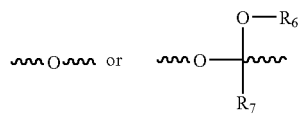

wherein $R_6$ is unsubstituted alkyl or alkyl substituted with one or more heteroatom containing groups;

$R_7$ is hydrogen, unsubstituted alkyl or alkyl substituted with one or more heteroatom containing groups; and Y is a spacer group selected from a substituted or unsubstituted —$(CH_2)_n$— chain with n=1-4; a substituted or unsubstituted —$(CH_2)_p$-HAC-$(CH_2)_q$— chain wherein each p and q independently is 1-3 and p+q is less than or equal to 3 and HAC is a heteroatom containing group; and a delayed release group comprising an aromatic group; and N is an anti-neoplastic alkylating agent.

5. The protected anti-neoplastic agent of claim 4 wherein Hyp is of the formula

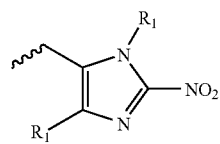

wherein $R_1$ and $R_4$ are each independently hydrogen or alkyl selected from methyl, ethyl, n-propyl, n-butyl, n-pentyl, t-butyl, cyclohexyl, cyclopentyl, and isopropyl, wherein the alkyl is optionally substituted with one or more heteroatom-containing groups; with the proviso that $R_1$ is not hydrogen.

6. The protected anti-neoplastic agent of claim 5 wherein the alkylating agent is selected from the group consisting of cyclophosphamide, ifosfamide, melphalan, chlorambucil, thiotepa.

7. The protected anti-neoplastic agent of claim 4 of formula

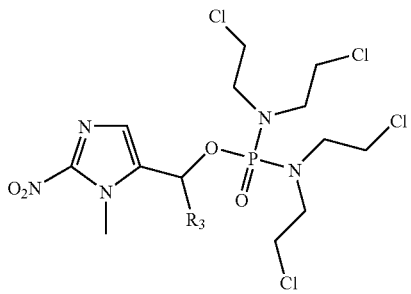

wherein $R_3$ is hydrogen or $C_1$-$C_6$ alkyl.

8. The protected anti-neoplastic agent of claim 2, wherein the alkylating agent is selected from the group consisting of cyclophosphamide, ifosfamide, melphalan, chlorambucil, thiotepa.

9. The protected anti-neoplastic agent of claim 1, wherein the one or more protectable hydroxyl groups or amine groups is substituted with Hyp-.

10. The protected anti-neoplastic agent of claim 1, wherein only one of the one or more protectable hydroxyl groups or amine groups is substituted with Hyp- or Hyp-L-.

11. The protected anti-neoplastic agent of claim 10, wherein the one protectable hydroxyl group or one protectable amine group is substituted with Hyp-.

12. The protected anti-neoplastic agent of claim 11, wherein a hydroxyl group is substituted with Hyp-.

13. The method of claim 3, wherein the one or more protectable hydroxyl groups or amine groups of the anti-neoplastic agent is substituted with Hyp-.

14. The method of claim 3, wherein only one of the one or more protectable hydroxyl groups or amine groups is substituted with Hyp- or Hyp-L-.

15. The method of claim 14, wherein the one protectable hydroxyl group or one protectable amine group is substituted with Hyp-.

16. The method of claim 15, wherein a protectable hydroxyl group of the anti-neoplastic is substituted with Hyp-.

17. The protected anti-neoplastic agent of claim 4 of formula Hyp-N.

18. The protected anti-neoplastic agent of claim 5 of formula Hyp-N.

* * * * *

UNITED STATES PATENT AND TRADEMARK OFFICE
CERTIFICATE OF CORRECTION

PATENT NO. : 7,550,496 B2  Page 1 of 1
APPLICATION NO. : 10/549545
DATED : June 23, 2009
INVENTOR(S) : Matteucci et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (78) days Delete the phrase "by 78 days" and insert -- by 147 days --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,550,496 B2 | Page 1 of 1 |
| APPLICATION NO. | : 10/549545 | |
| DATED | : June 23, 2009 | |
| INVENTOR(S) | : Matteucci et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 415 days.

Signed and Sealed this
Twenty-first Day of February, 2012

David J. Kappos
*Director of the United States Patent and Trademark Office*